(12) United States Patent
Chari et al.

(10) Patent No.: US 9,090,629 B2
(45) Date of Patent: Jul. 28, 2015

(54) CYTOTOXIC AGENTS COMPRISING NEW ANSAMITOCIN DERIVATIVES

(75) Inventors: Ravi V. J. Chari, Newton, MA (US); Wayne C. Widdison, Belmont, MA (US); Sharon D. Wilhelm, Arlington, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 13/883,344

(22) PCT Filed: Nov. 3, 2011

(86) PCT No.: PCT/US2011/059131
§ 371 (c)(1),
(2), (4) Date: Aug. 21, 2013

(87) PCT Pub. No.: WO2012/061590
PCT Pub. Date: May 10, 2012

(65) Prior Publication Data
US 2013/0323268 A1    Dec. 5, 2013

Related U.S. Application Data

(60) Provisional application No. 61/409,831, filed on Nov. 3, 2010.

(51) Int. Cl.
| | | |
|---|---|---|
| *A61K 39/00* | (2006.01) | |
| *C07D 498/16* | (2006.01) | |
| *A61K 47/48* | (2006.01) | |
| *A61K 45/06* | (2006.01) | |

(52) U.S. Cl.
CPC ............... *C07D 498/16* (2013.01); *A61K 45/06* (2013.01); *A61K 47/48215* (2013.01); *A61K 47/48384* (2013.01); *A61K 47/48561* (2013.01)

(58) Field of Classification Search
CPC ....................................................... A61K 39/00
USPC .......... 424/143.1, 130.1, 133.1, 141.1, 178.1; 530/387.1, 388.1, 388.22; 514/2
See application file for complete search history.

(56) References Cited

U.S. PATENT DOCUMENTS

| | | | |
|---|---|---|---|
| 4,331,598 A | 5/1982 | Hasegawa et al. | |
| 7,754,681 B2 | 7/2010 | Feng | |
| 2010/0129314 A1 | 5/2010 | Singh et al. | |

FOREIGN PATENT DOCUMENTS

| | | |
|---|---|---|
| WO | WO-2004/103272 A2 | 12/2004 |
| WO | WO-2006-034488 A2 | 3/2006 |
| WO | WO-2009-134976 A1 | 11/2009 |

*Primary Examiner* — Bruck Kifle
(74) *Attorney, Agent, or Firm* — McCarter & English, LLP; Steven G. Davis; Yu Lu

(57) ABSTRACT

New ansamitocin derivatives bearing a linking group are disclosed. Also disclosed are methods for the synthesis of these new ansamitocin derivatives and methods for their linkage to cell-binding agents. The ansamitocin derivative-cell-binding agent conjugates are useful as therapeutic agents, which are delivered specifically to target cells and are cytotoxic. These conjugates display vastly improved therapeutic efficacy in animal tumor models compared to the previously described agents.

11 Claims, 33 Drawing Sheets

FIG. 1.

Linkable Maytansinoids (May = maytansinoid)

Y' = $(CR_7R_8)_l(CR_9=CR_{10})_p(C\equiv C)_qA_o(CR_5R_6)_mD_u(CR_{11}=CR_{12})_r(C\equiv C)_sB_t(CR_3R_4)_nCR_1R_2SZ$ FIG. 2. Structures of Ansamitocins and Maytansine
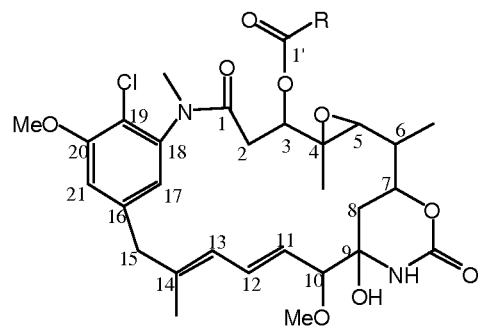
Ansamitocin P1:  R = -CH$_3$
Ansamitocin P2:  R = -CH$_2$CH$_3$
Ansamitocin P3:  R = -CH(CH$_3$)$_2$
Ansamitocin P3': R = -CH$_2$CH$_2$CH$_3$
Ansamitocin P4:  R = -CH$_2$CH(CH$_3$)$_2$
Ansamitocin P4': R = -CH$_2$CH$_2$CH$_2$CH$_3$
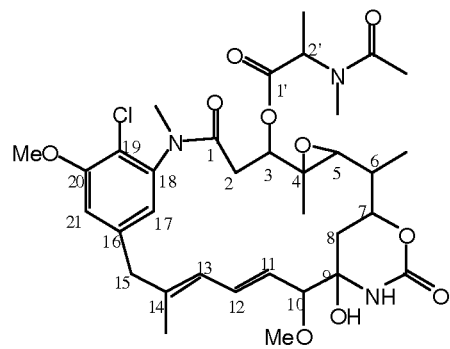
Maytansine FIG. 3. In Vitro Potency of Ansamitocins and Maytansine
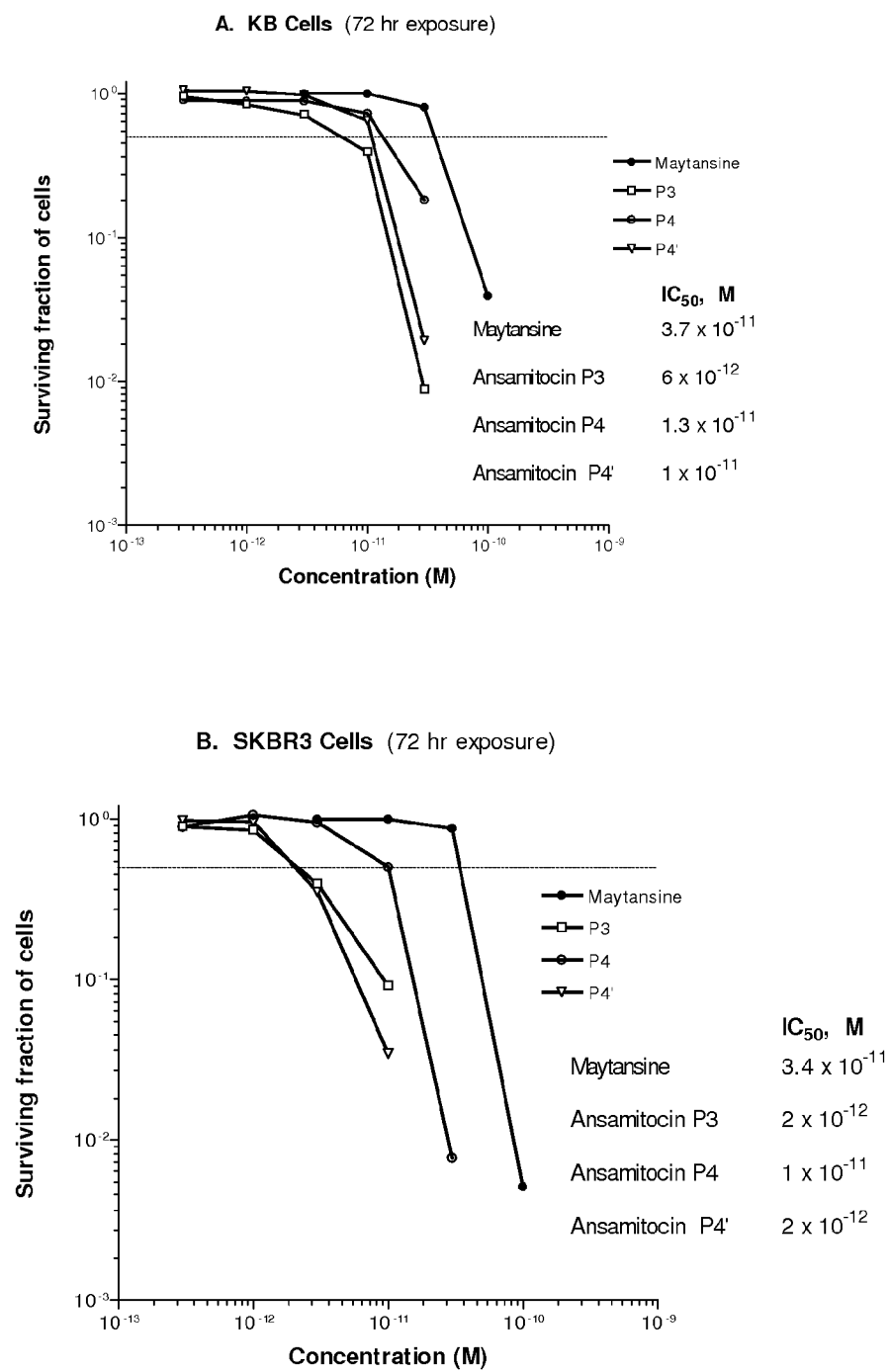

FIG. 4. Synthesis of side chains

FIG. 5. Synthesis of thiol-containing ansamitocin derivatives
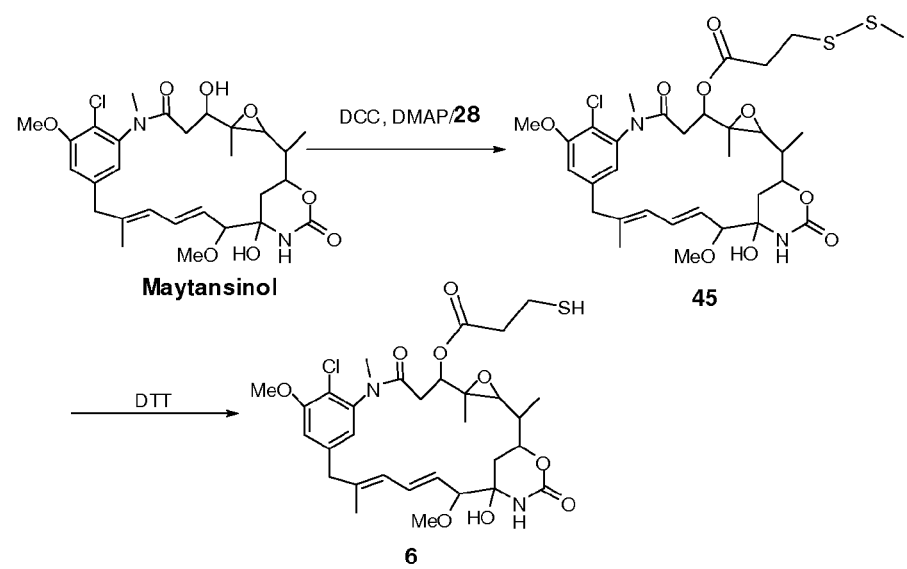

FIG. 6. Synthesis of thiol-containing ansamitocin derivatives bearing aromatic or heterocyclic side chain FIG. 7A. Synthesis of a thiol-containing pegylated ansamitocin derivative
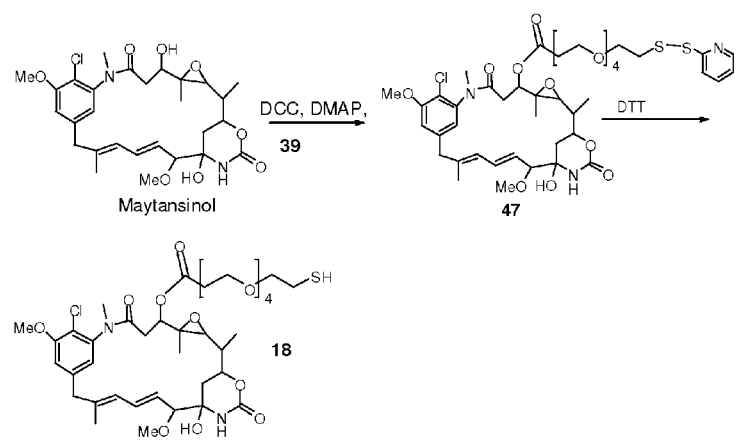
FIG. 7B. Synthesis of a thiol reactive pegylated ansamitocin derivative
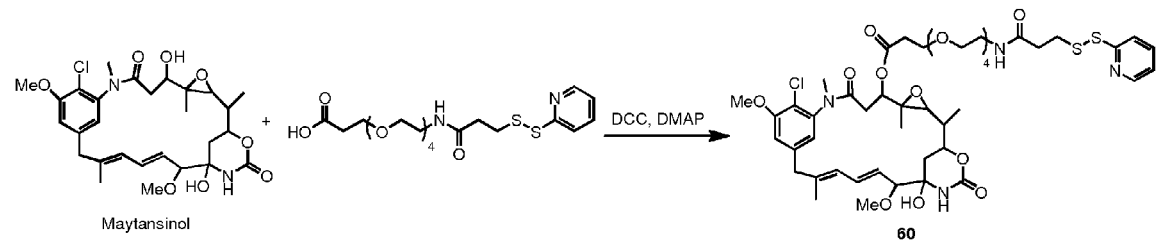

FIG. 8. Synthesis of an ansamitocin derivative bearing a peptidase labile linker
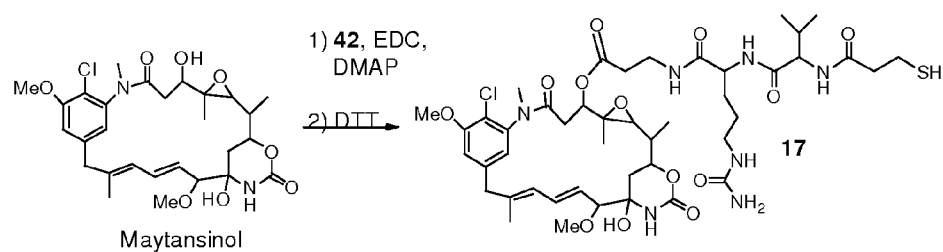
FIG. 9. Synthesis of ansamitocin derivatives bearing a carbonyl group
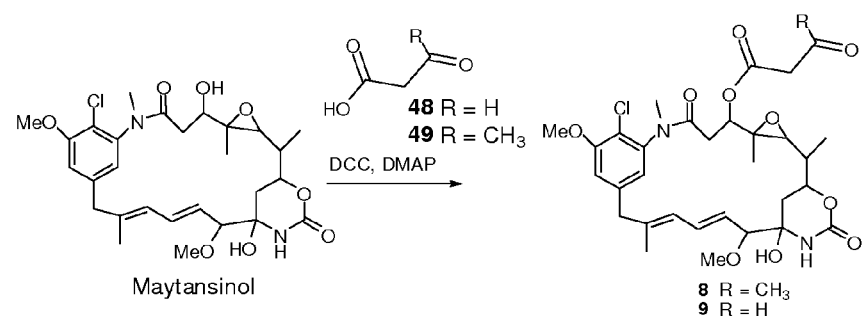

FIG. 10A. Synthesis of ansamitocin derivatives bearing an amino group
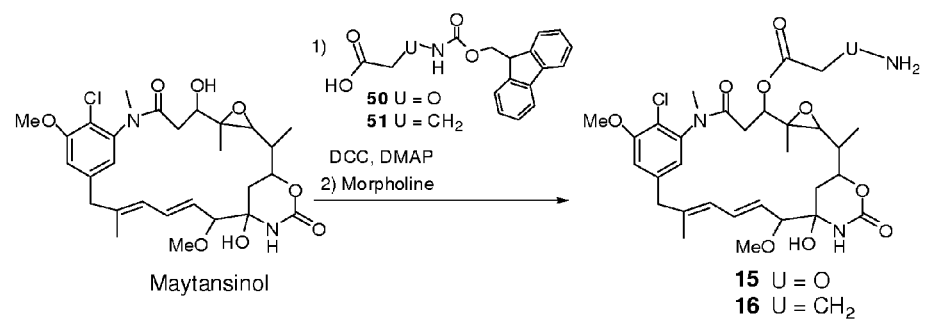
FIG. 10B. Synthesis of ansamitocin derivative bearing a dimethylamino group
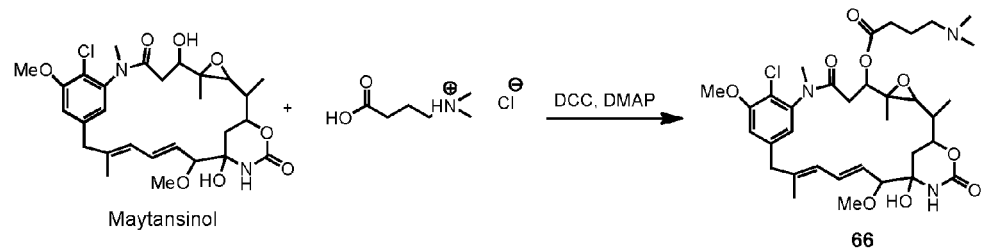

FIG. 11. Synthesis of ansamitocin derivatives bearing an N-hydroxysuccinimidyl ester group
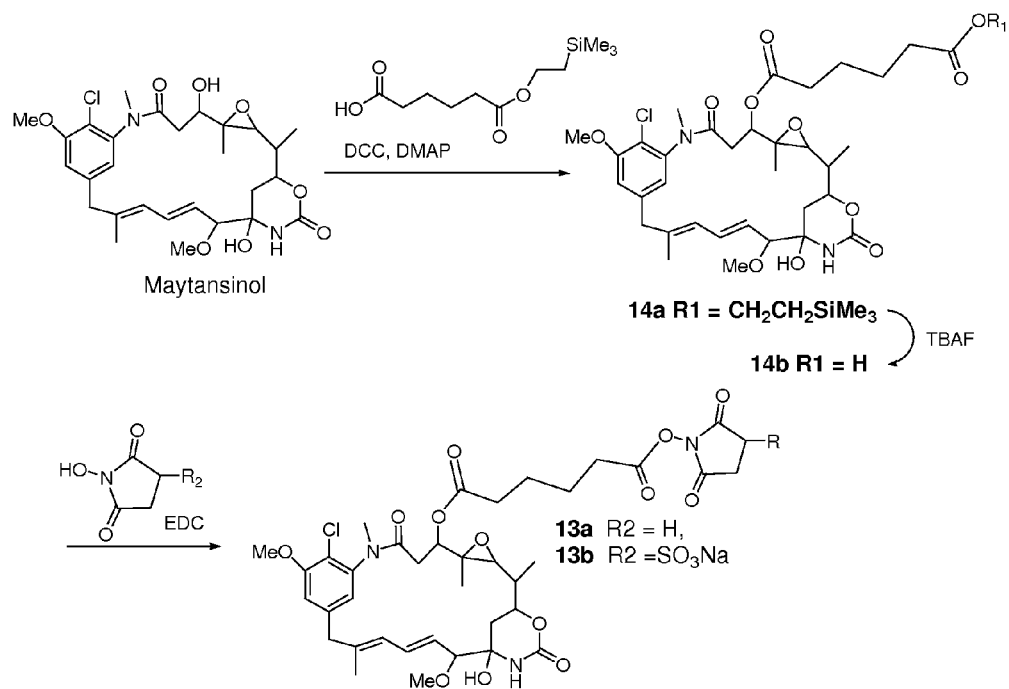

FIG. 12A. Synthesis of an ansamitocin derivative bearing an ether group
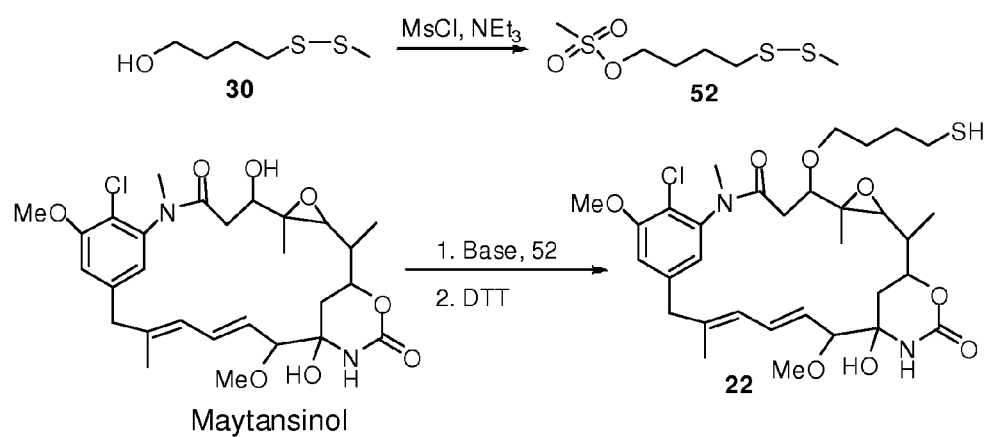
FIG. 12B. Synthesis of ansamitocin derivatives bearing a carbamate or carbonate group
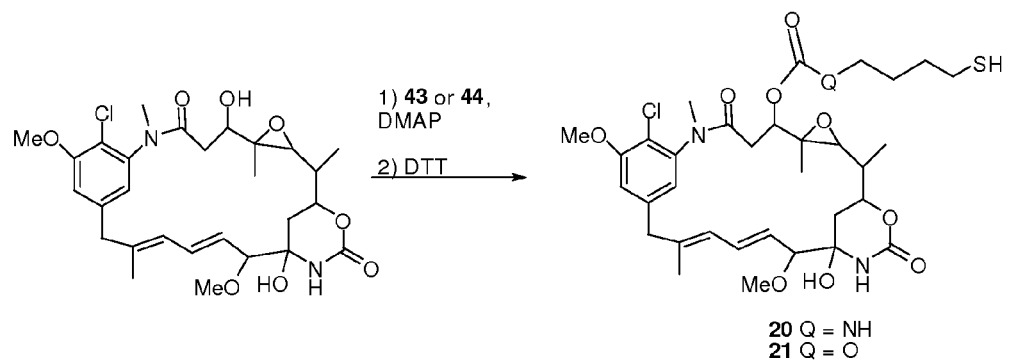

FIG. 13A. Synthesis of thiol-containing ansamitocin
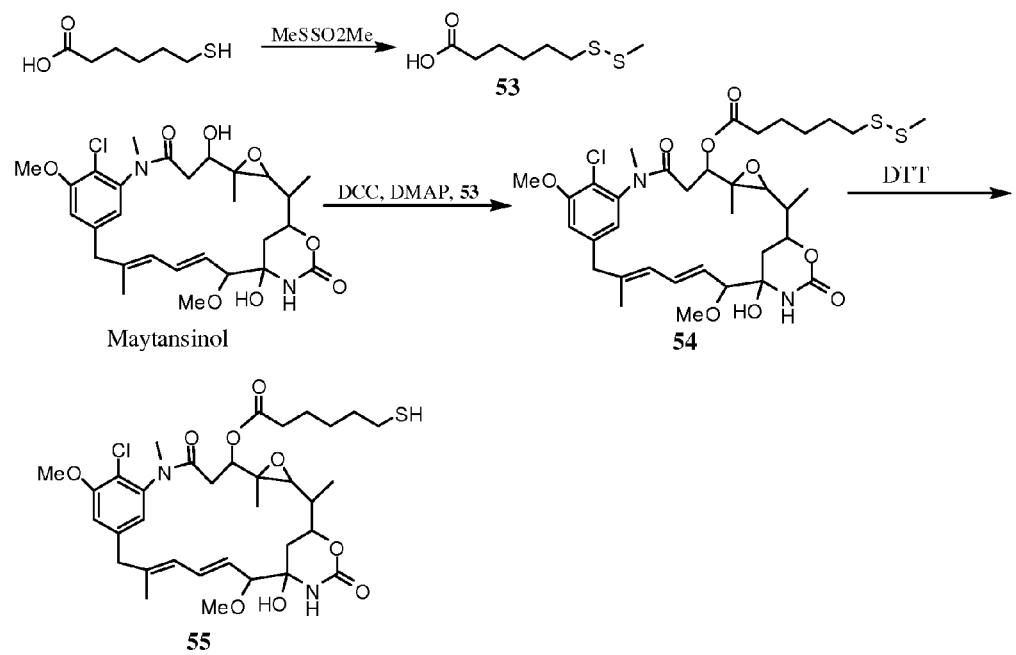

FIG. 13B. Synthesis of thiol-containing ansamitocin
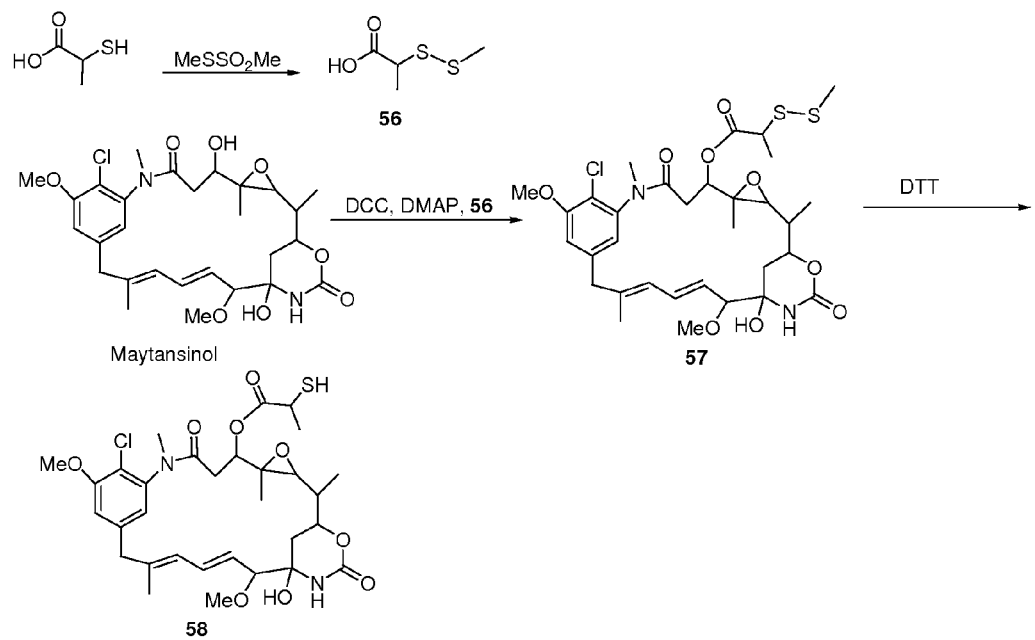

FIG. 13C. Synthesis of thiol-containing ansamitocin
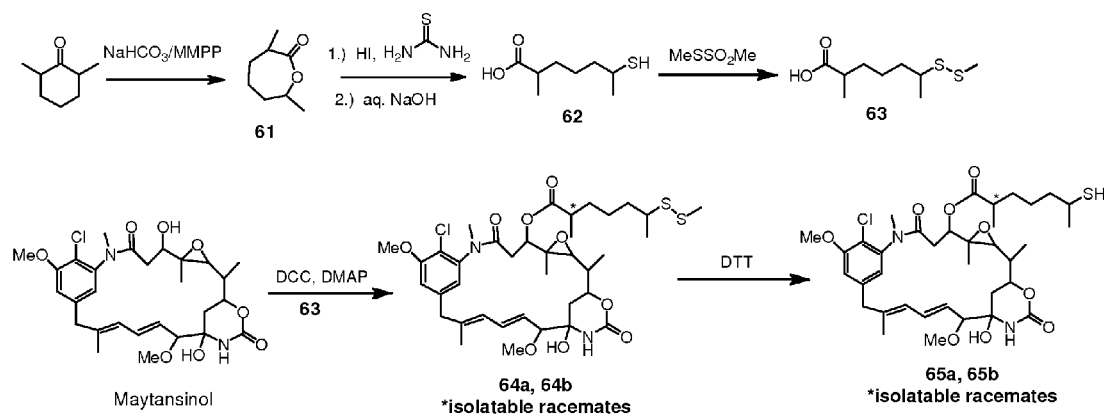

FIG. 14. Conjugation procedure for a disulfide-linked conjugate
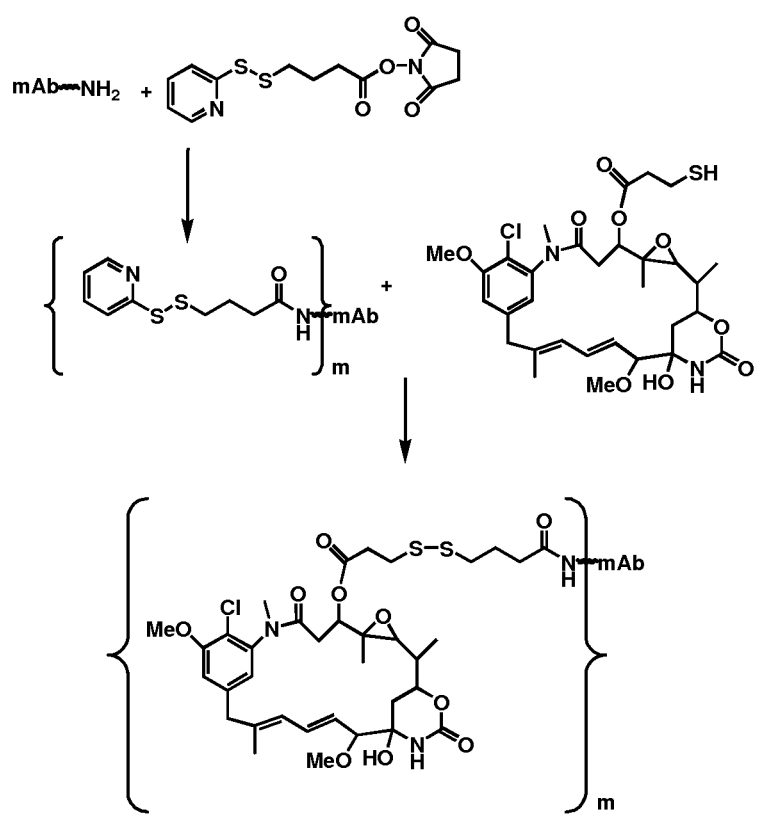

FIG. 15. Conjugation procedure for a thiosuccinimidyl-linked conjugate
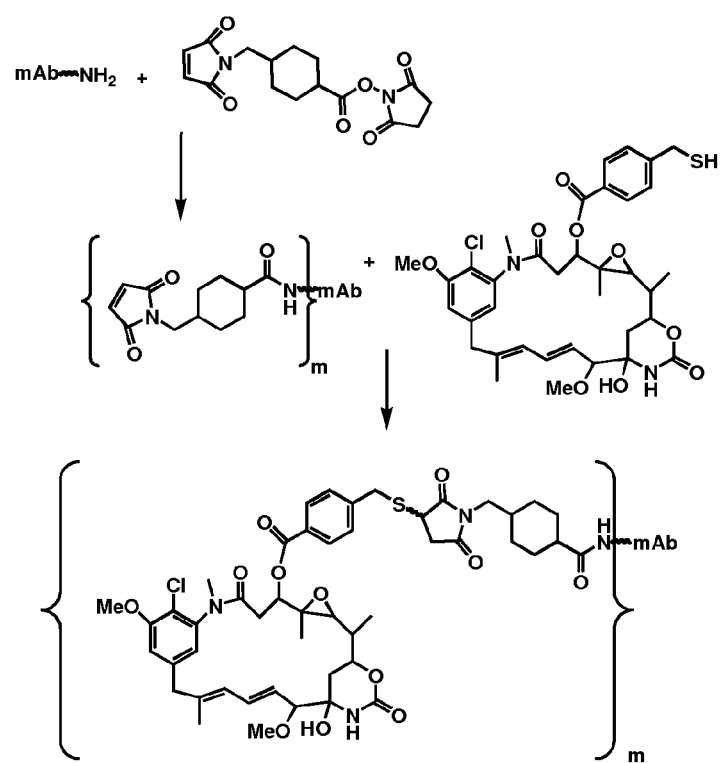

FIG. 16. Conjugation procedure for a thioacetamidyl-linked conjugate
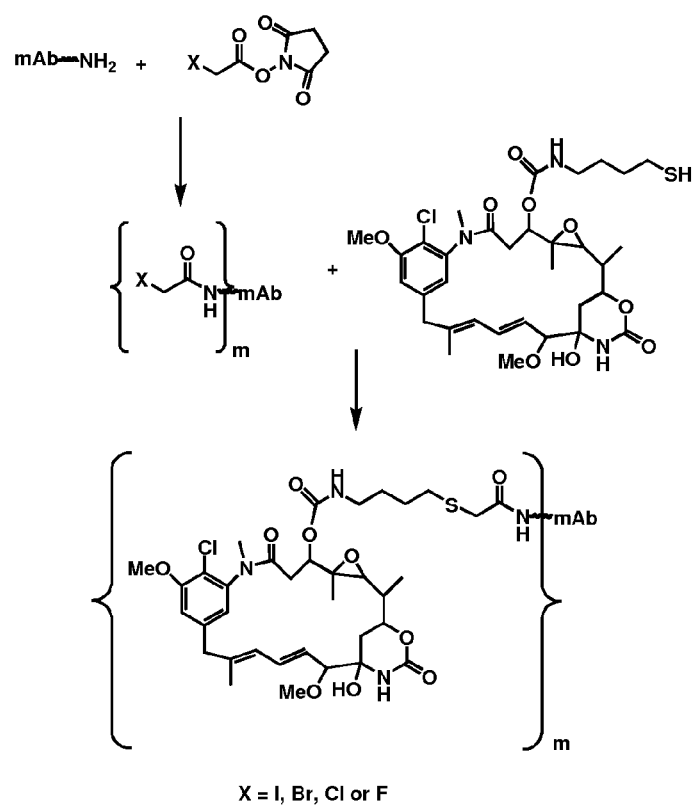

FIG. 17. Conjugation procedure for a peptidase-labile conjugate
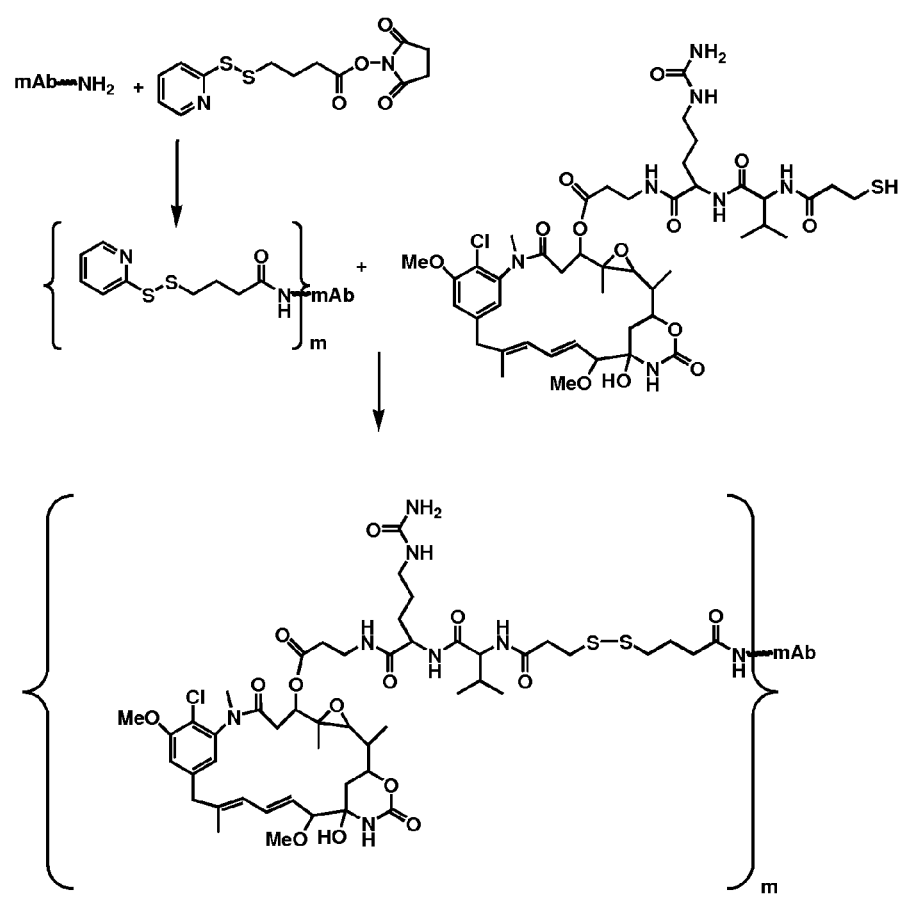

FIG. 18. Conjugation procedure for a peptidase-labile thiosuccinimidyl-linked conjugate
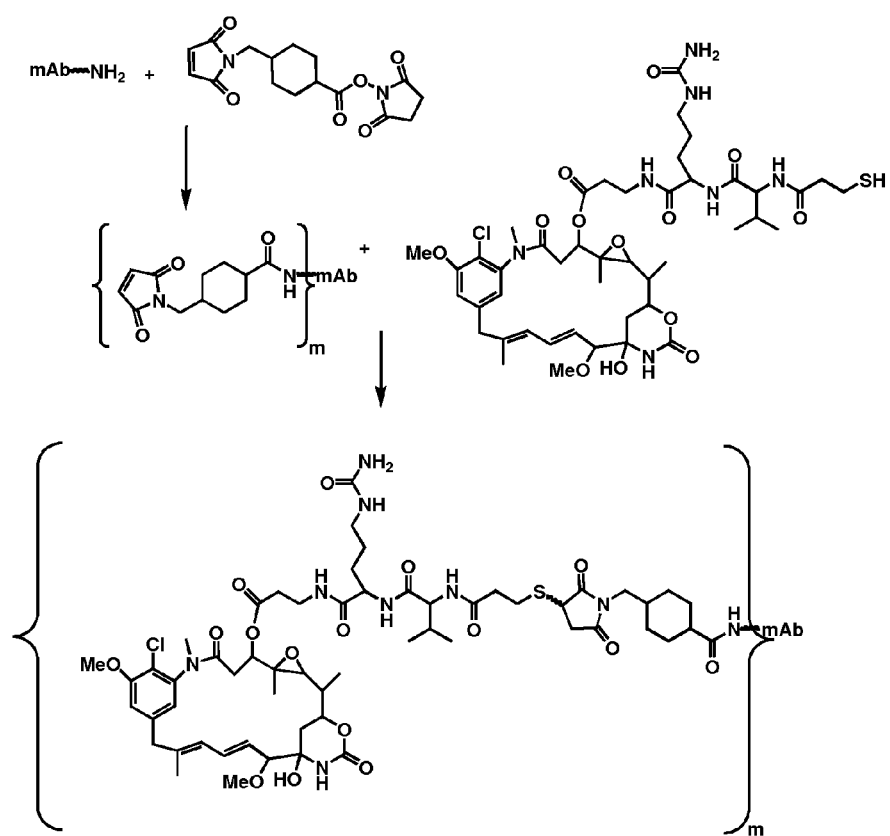

FIG. 19. Conjugation procedure for a peptidase-labile thioacetamidyl-linked conjugate
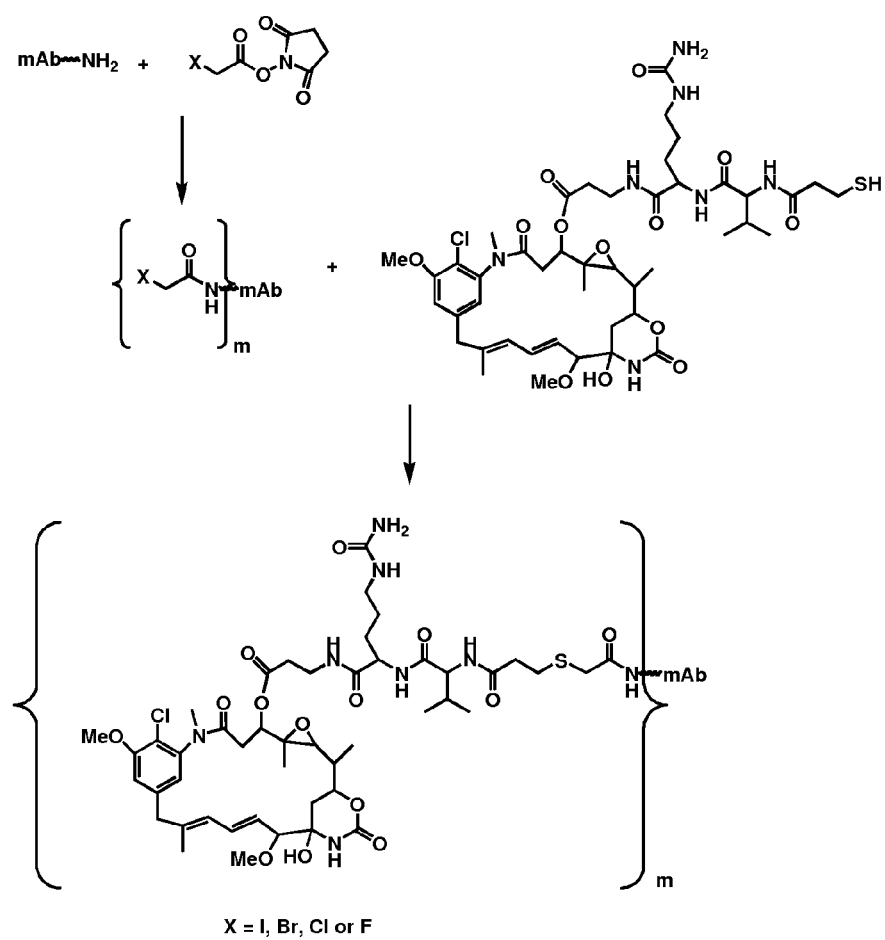

FIG. 20. Conjugation procedure for an amide-linked conjugate
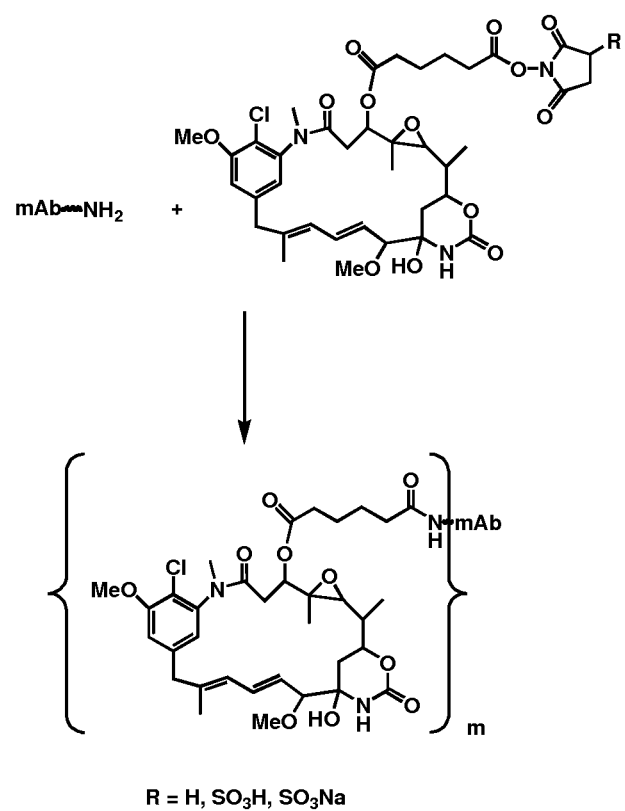
R = H, SO₃H, SO₃Na FIG. 21. Conjugation procedure for a hydrazone-linked conjugate
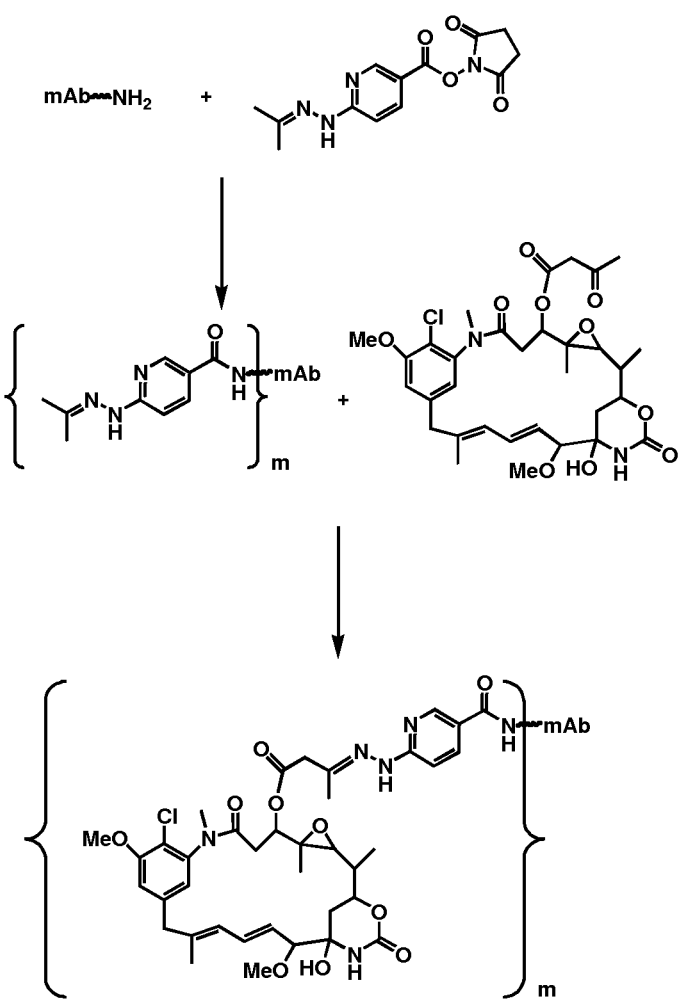

FIG. 22. Conjugation procedure for a hydrazone-linked conjugate
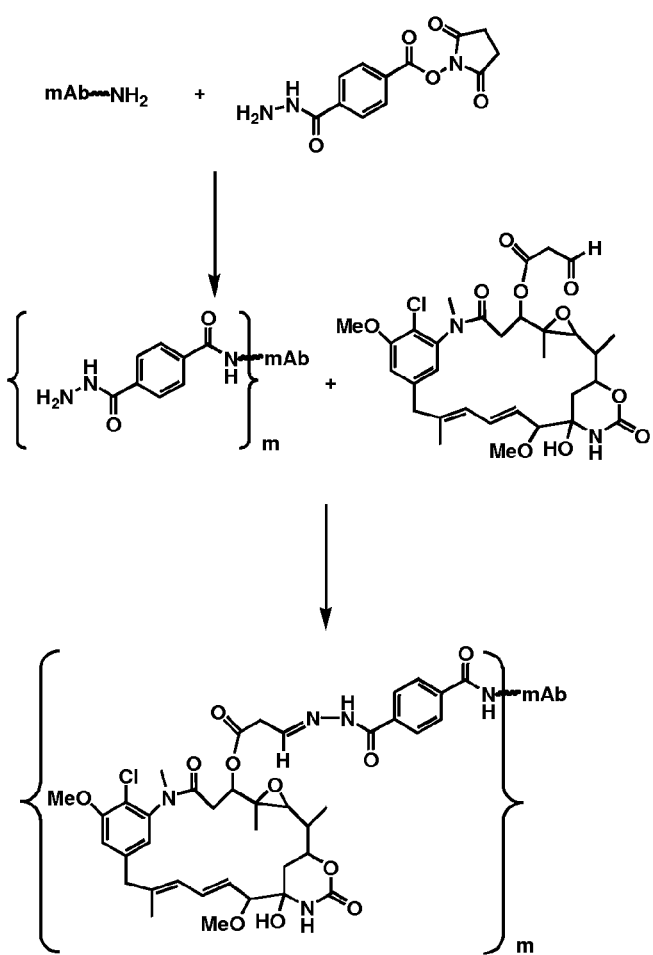

FIG. 23. Conjugation procedure for a hydrazone-linked conjugate
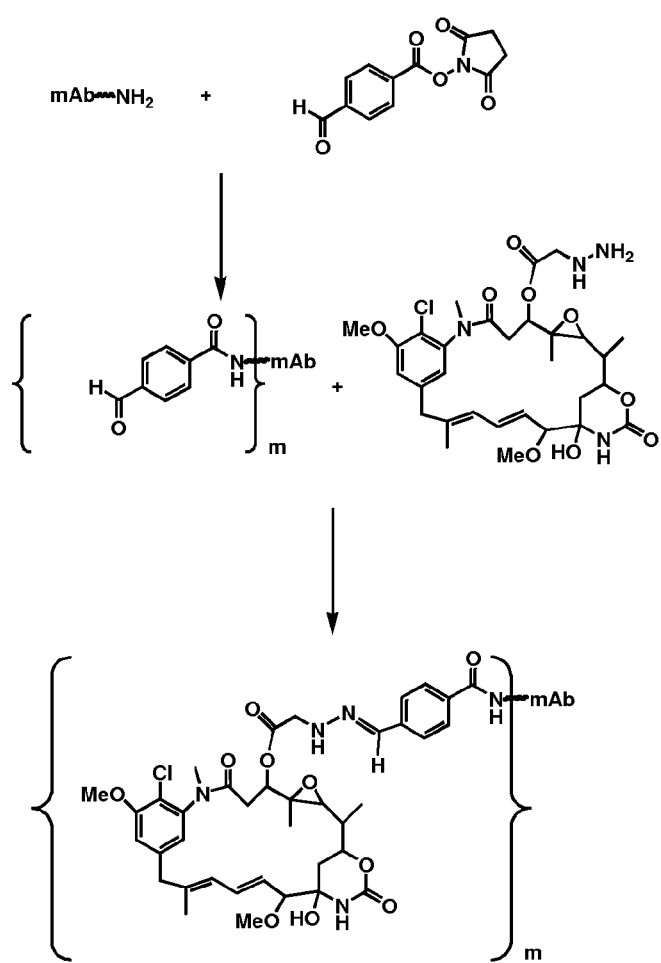

FIG. 24. Conjugation procedure for an amide-linked conjugate

PLP: pyridoxal 5' phosphate

EDC: 1-Ethyl-3-[3-dimethylaminopropyl]carbodiimide hydrochloride
NHS: N-hydroxysuccinimide FIG. 25. Conjugation procedure for disulfide-linked conjugates
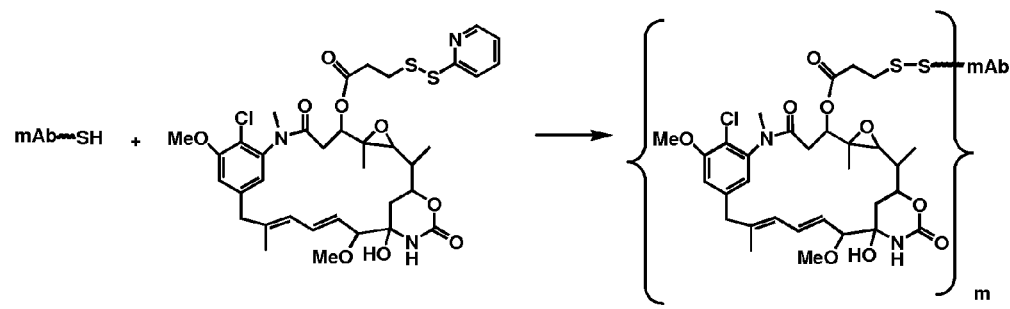

FIG. 26. Conjugation procedure using a thioether link
A.
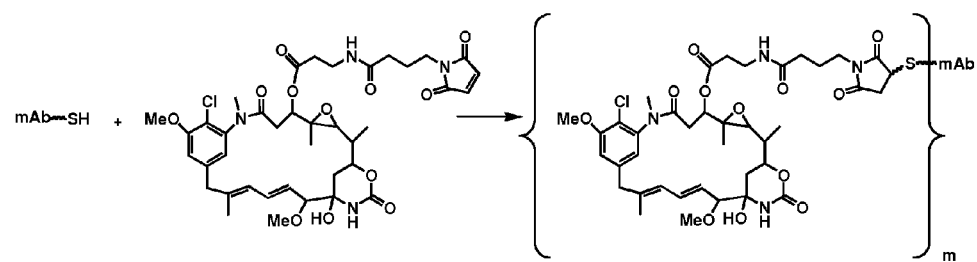
B.
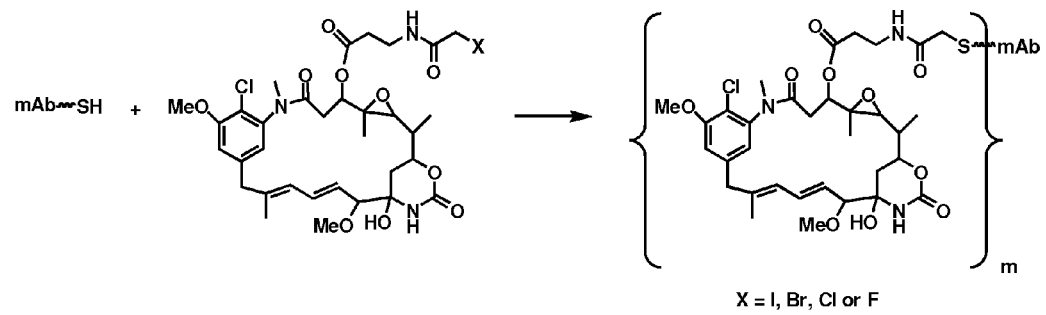
X = I, Br, Cl or F FIG. 26. Conjugation procedure using a thioether link - Continued
C.
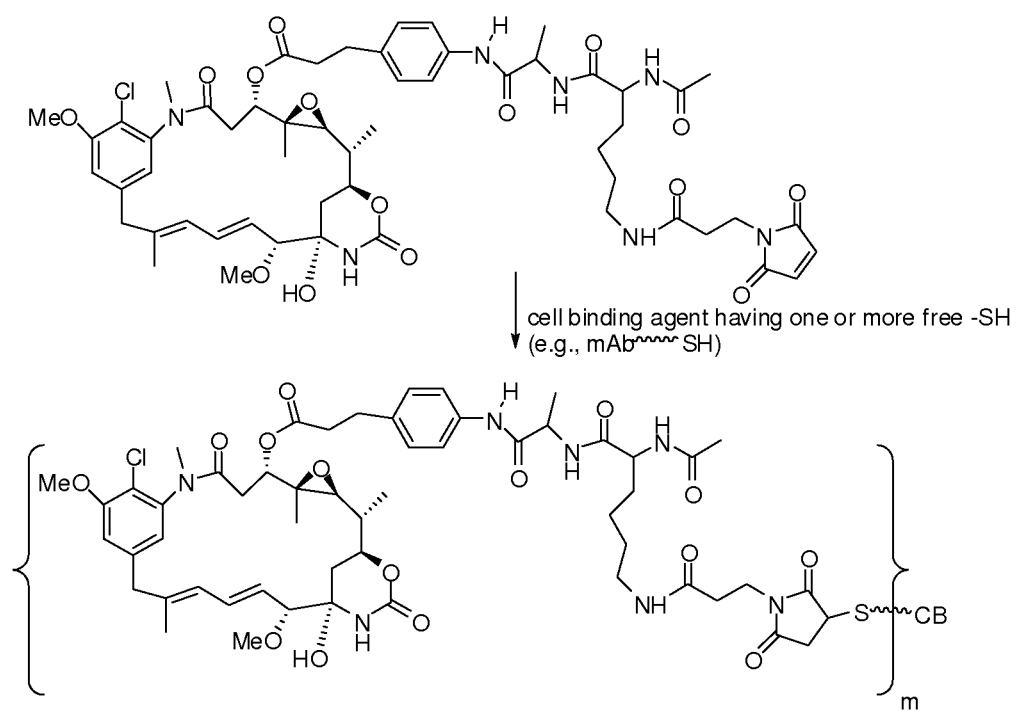

FIG. 27. Conjugation scheme for an amide-linked conjugate
A.
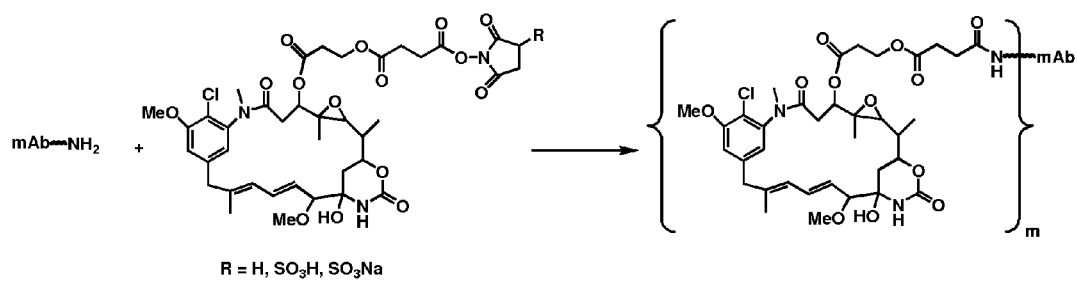
R = H, SO₃H, SO₃Na
B.
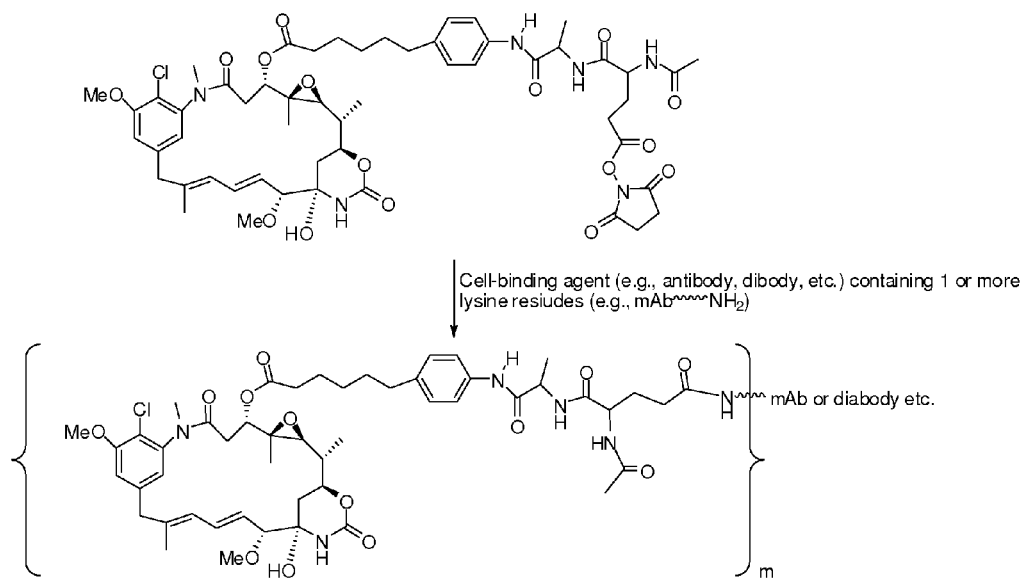

FIG. 28. In vitro activity of prepared ansamitocin derivatives against the KB cell line (96 hour ex FIG. 29. *In vitro* activity of prepared ansamitocin derivatives against the COLO 205 cell line (96 hour exposure)
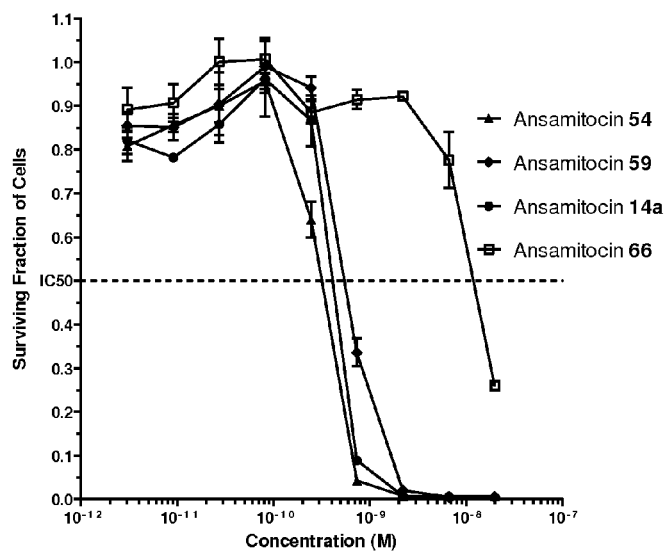
FIG. 30. *In vitro* activity of prepared ansamitocin derivatives against the COLO 205-MDR cell line (96 hour exposure)
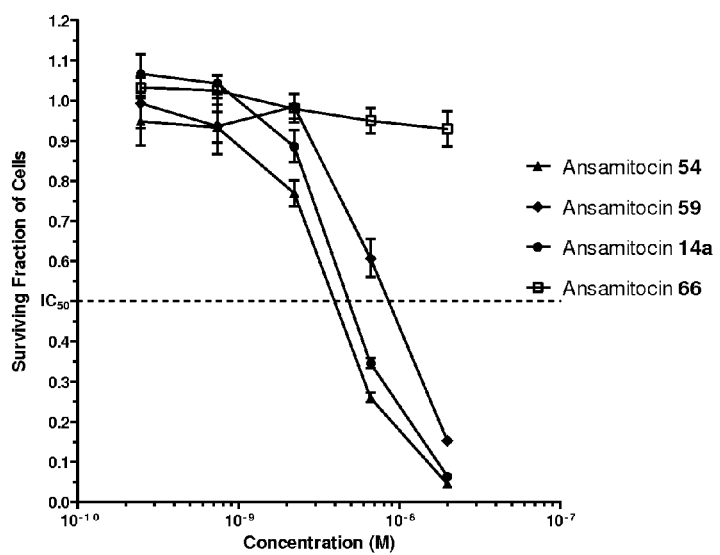

FIG. 31. *In vitro* activity of conjugates prepared with linkable ansamitocin derivatives and the thiol-bearing maytansinoid, DM1, against COLO 205 cells
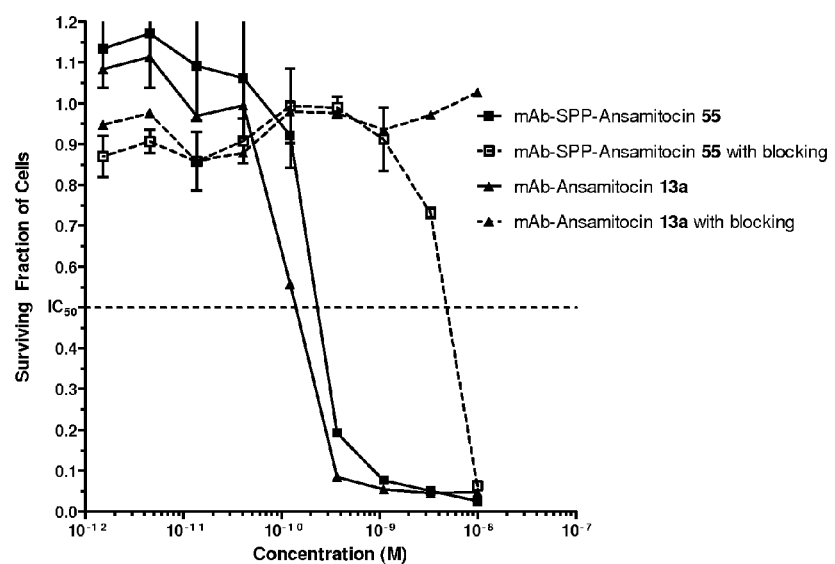

CYTOTOXIC AGENTS COMPRISING NEW ANSAMITOCIN DERIVATIVES

RELATED APPLICATIONS

This application claims the benefit of U.S. Provisional Application Ser. No. 61/409,831, filed Nov. 3, 2010, the entire teachings of which are incorporated herein by reference.

FIELD OF THE INVENTION

The present invention relates to a method for preparing cytotoxic conjugates comprising ansamitocin derivatives and cell-binding agents. These conjugates have therapeutic use as they are delivered to a specific cell population in a targeted fashion. The present invention also relates to a method for preparing ansamitocin derivatives having a linker moiety, which may be used in the preparation of cytotoxic conjugates. The present invention further relates to novel ansamitocin derivatives.

BACKGROUND OF THE INVENTION

Antibody conjugates of cytotoxic drugs are being developed as target-specific therapeutic agents. Antibodies against various cancer cell-surface antigens have been conjugated with different cytotoxic agents (see Chari 1998, *Adv. Drug Delivery Revs.*, 31, p 89-104; Chari, 2008, *Acc. Chem. Res.*, 41, p 98-107; Ducry & Stump, 2010, *Bioconjugate Chem.*, 21, p 5-13; Senter, 2009, *Curr Opinions in Chem. Biol.*, 13, p 235-244; Ojima. et al., 2002, *J. Med. Chem.* 45, 5620-5623; Hamann, P. R. et al., 2002, *Bioconjug Chem.* 13, 47-58; Bross, P. F. et al., 2001 *Clin Cancer Res.* 7, 1490-6; DiJoseph, J. F. et al., 2004, *Blood*, 103:1807-1814; Doronina, S. O., et al., 2003, *Nat. Biotechnol.* 21, 778-784; Doronina, S. O., et al., 2006, *Bioconjug Chem.* 17, 114-24).

The cytotoxic compounds used in antibody-drug conjugates inhibit various essential cellular targets, such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; 7,276,497; 7,301,019; 7,303,749; 7,368,565; 7,473,796; 7,585,857; 7,598,290; 7,495,114; 7,601,354, U.S. Patent Application Nos. 20100092495, 20100129314, 20090274713, 20090076263, 20080171865) and DNA (calicheamicin, doxorubicin, CC-1065 analogues: U.S. Pat. Nos. 5,475,092; 5,585,499; 5,846,545; 6,534,660; 6,756,397; 6,630,579; 7,388,026; 7,655,660; 7,655,661). In these conjugates, the cytotoxic moiety and the antibody are linked together either via a cleavable linker, such as a disulfide bond, acid-labile bond, peptidase-labile bond, or esterase-labile bond, or via a non-cleavable linker, such as a thioether bond or an amide bond. Antibody conjugates with some of these cytotoxic drugs are actively being investigated in the clinic for cancer therapy (Richart, A. D., and Tolcher, A. W., 2007, *Nature Clinical Practice*, 4, 245-255; Krop et al., 2010, *J. Clin. Oncol.*, 28, p 2698-2704).

A wide array of linker technologies has been employed for the preparation of such immunoconjugates, and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (*Biochem. Biophys. Res. Commun.* 102:1048-1054 (1981)). Yang and Reisfeld used the same technique to conjugate daunorubicin to an anti-melanoma antibody (*J. Natl. Canc. Inst.* 80:1154-1159 (1988)). Dillman et al. used an acid-labile linker in a similar fashion to prepare conjugates of daunorubicin with an anti-T cell antibody (*Cancer Res.* 48:6097-6102 (1988)).

An alternative approach, explored by Trouet et al. involved linking daunorubicin to an antibody via a peptide spacer arm (*Proc. Natl. Acad. Sci.* 79:626-629 (1982)). This was done under the premise that free drug could be released from such a conjugate by the action of lysosomal peptidases.

Maytansinoids are highly cytotoxic drugs. Maytansine was first isolated by Kupchan et al. from the east African shrub *Maytenus serrata* and shown to be 100 to 1000-fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al. *J. Med. Chem.* 21:31-37 (1978); Higashide et al. *Nature* 270:721-722 (1977); Kawai et al. *Chem. Pharm. Bull.* 32:3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters of maytansinol can be classified into two groups:
(a) C-3 esters with simple carboxylic acids (U.S. Pat. Nos. 4,248,870; 4,265,814; 4,308,268; 4,308,269; 4,309,428; 4,317,821; 4,322,348; and 4,331,598 and *Chem. Pharm. Bull.* 1984, 12:3441), and
(b) C-3 esters with derivatives of N-methyl-L-alanine (U.S. Pat. Nos. 4,137,230; 4,260,608; 5,208,020; and *Chem. Pharm. Bull.* 1984, 12:3441).

Esters of group (b) bearing an acylated N-methylalanine ester were found to be much more cytotoxic than the ansamitocin esters of group (a). For example, Kupchan et al. (*J. Med. Chem.*, 21; 31 (1978) reported that ansamitocin analogues (simple C3 esters of maytansinol) such as a propionyl ester, bromoacetyl ester, crotonyl ester and trifluoroacetyl ester were 34 to 1640-fold less potent ($IC_{50}$=0.00021–0.01 micrograms/mL) towards cancer cells than esters such as maytansine that bear an acylated N-methyl-L-alanine ester at C3 ($IC_{50}$=0.0000061 micrograms/mL). Of the six simple ansamitocin esters tested in this study only 2 of them had comparable potency to the N-methylalanine containing compound maytansine. In contrast, N-acyl-N-methyl-L-alanyl esters of maytansinol were highly potent regardless of the nature of the acyl group. Other modified ansamitocins have been reported by Kawai et al. (*Chem. Pharm. Bull.*, 32; 3441, 1984). Most of these compounds were reported to have antimicrobial activity at 1 to 4 micrograms/mL. Cell killing activity towards cancer cells in vitro was not reported.

Maytansine is an N-acetyl-N-methyl-L-alanyl ester of maytansinol. It is a highly potent mitotic inhibitor. Treatment of L1210 cells in vivo with maytansine has been reported to result in 67% of the cells accumulating in mitosis. Untreated control cells were reported to demonstrate a mitotic index ranging from between 3.2 to 5.8% (Sieber et al. 43 *Compara-* tive Leukemia Research 1975, Bibl. Haemat. 495-500 (1976)). Experiments with sea urchin eggs and clam eggs have suggested that maytansine inhibits mitosis by interfering with the formation of microtubules through the inhibition of the polymerization of the microtubule protein, tubulin (Remillard et al. *Science* 189:1002-1005 (1975)).

In vitro, P388, L1210, and LY5178 murine leukemic cell suspensions have been found to be inhibited by maytansine at doses of $10^{-3}$ to $10^{-1}$ μg/μl, with the P388 line being the most sensitive. Maytansine has also been shown to be an active inhibitor of in vitro growth of human nasopharyngeal carcinoma cells, and the human acute lymphoblastic leukemia line CEM was reported inhibited by concentrations as low as $10^{-7}$ mg/ml (Wolpert-DeFillippes et al. *Biochem. Pharmacol.* 24:1735-1738 (1975)).

In vivo, maytansine has also been shown to be active. Tumor growth in the P388 lymphocytic leukemia system was shown to be inhibited over a 50 to 100-fold dosage range, which suggested a high therapeutic index; also significant inhibitory activity could be demonstrated with the L1210 mouse leukemia system, the human Lewis lung carcinoma system and the human B-16 melanocarcinoma system (Kupchan, *Fed. Proc.* 33:2288-2295 (1974)).

Based on its high potency, analogues of maytansine bearing various acyl side chains on the N-methylalanyl moiety suitable for linking to cell binding agents have been described (see for example U.S. Pat. Nos. 5,208,020; 5,416,064; 7,473,796; 7,368,565; 7,301,019; 7,276,497; 6,716,821; 6,441,163; U.S. Patent Application Nos. 20100129314; 20100092495; 20090274713; 20090076263; 20080171865; 20080171856; 20070270585; 20070269447; 20070264266; and 20060167245; Chari et al., *Cancer Res.*, 52: 127-131 (1992); Liu et al., *Proc. Natl. Acad. Sci.*, 93: 8618-8623 (1996); and Widdison et al., *J. Med. Chem.*, 49; 4392, 2006). In these conjugates, the cell-binding agent is linked via disulfide bonds to the maytansinoids such as DM1 [$N^{2'}$-deacetyl-N-$^{2'}$(3-mercapto-1-oxopropyl)-maytansine, CAS Number: 139504-50-0, FIG. 1] or DM4 [$N^{2'}$-deacetyl-N-$^{2'}$(4-mercapto-4-methyl-1-oxopentyl)-maytansine, CAS Number: 796073-69-3].

In the above patents, the maytansinoid drugs used for linkage to cell binding agents bear an acylated N-methyl alanine or a N-methyl cysteine-containing ester side chain (see FIG. 1). The N-methyl alanine or N-methyl cysteine containing side chain has to be of the L configuration to get high potency, with the D-isomer being up to 100-fold less potent (see Widdison et al., *J. Med. Chem.*, 49; 4392, 2006).

SUMMARY OF THE INVENTION

The present invention is based on the unexpected findings that, contrary to previous reports, ansamitocins bearing different simple C3 esters (propionyl, isobutyl, isopentanoyl, pentanoyl), are highly potent and even more potent than the N-methylalanine containing ester maytansine (see FIGS. 2 and 3). For example, the ansamitocin bearing a C3 propionyl ester was reported to be about 34.4-fold less potent than maytansine towards KB cells (Kupchan et al. *J. Med. Chem.* 21:31-37, 1978). However, herein, the same ansamitocin bearing a C3 propionyl ester was found to be 1.3-fold more potent than maytansine towards the KB cell line. Similar results demonstrating the higher potency of ansamitocins compared to maytansine were also observed with another cell line SK-Br-3 (see FIG. 3). Thus, ansamitocins possess sufficient potency for targeted delivery using cell binding agents.

Accordingly, the present invention describes new ansamitocin derivatives bearing a functional group that can be used for linkage to cell binding agents.

In a first embodiment the invention relates to a cell binding agent conjugate comprising a cell binding agent chemically linked to a derivatized maytansinol or maytansinol analog residue represented by the following formula (I):

MayO-A-    (I);

or a pharmaceutically acceptable salt or solvate thereof, wherein: MayO is a residue of maytansinol or maytansinol analog represented by MayOH; A is an optional group selected from C=O, C(=O)NR', and C(=O)O, R' is selected from H, substituted or unsubstituted linear, branched, or cyclic alkyl, alkenyl or alkynyl, and substituted or unsubstituted aryl, provided that the conjugate does not comprise a N-methylalanine or N-methylcysteine moiety represented by the following formula:

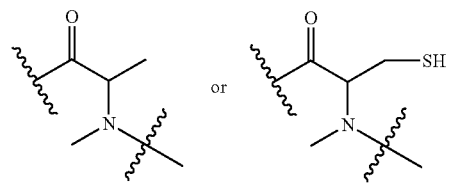

directly connected to MayO—.

In a second embodiment the invention relates to a cell binding agent conjugate comprising a derivatized maytansinol or maytansinol analog residue represented by the following formula (II):

MayO-A-Y-    (II);

a pharmaceutically acceptable salt or solvate thereof, wherein MayO and A are as described in formula (I) and Y is an optional group selected from a substituted or unsubstituted linear, branched, or cyclic alkyl, alkenyl or alkynyl, a substituted or unsubstituted aryl, a substituted or unsubstituted heterocyclic group, a substituted or unsubstituted arylalkyl, a substituted or unsubstituted heterocyclylalkyl group, an aziridine group, and an epoxy group, wherein each of the alkyl, alkenyl, alkynyl, arylalkyl, heterocyclylalkyl groups is optionally interrupted by one or more group selected from a polyethylene glycol unit $(OCH_2CH_2)_n$, an aziridine group, an epoxy group, an amino group, an amido group, an ester group, an aryl group and a heterocyclic group, an amino acid and a peptide, wherein: n is an integer from 1 to 200;

In a third embodiment the invention relates to a cell binding agent conjugate represented by formula (III):

(MayO-A-Y-L')$_m$-CB    (III);

or a pharmaceutically acceptable salt or solvate thereof, wherein: MayO, A and Y are as described in the first and second embodiments, L' is a linker; m is an integer from 1 to 20, and CB represents a cell binding agent.

In a fourth embodiment the invention relates to a cell binding agent conjugate represented by formula (IV):

MayO-A-Y-L'-CB    (IV);

or a pharmaceutically acceptable salt or solvate thereof; wherein: MayO, A, L' and CB are as defined in the first second and third embodiments; Y is an optional group and selected from a substituted or unsubstituted linear, branched, or cyclic alkyl, alkenyl or alkynyl, a substituted or unsubstituted aryl, a substituted or unsubstituted heterocyclic group, each group bearing an optional polyethylene glycol unit $(OCH_2CH_2)_n$, wherein: n is an integer from 1 to 200, and a peptide.

In a fifth embodiment the invention relates to a cell binding agent conjugate represented by formula (V):

$(MayO-A-Y-M'-BFCG)_m-CB$ (V);

or a pharmaceutically acceptable salt or solvate thereof, wherein: MayO, A, Y, m and CB are as defined in the first, second, third and fourth embodiments; BFCG is absent or the residue of a bifunctional crosslinking reagent comprising two linking groups, wherein one of the linking groups has reacted with M' and the other linking group has reacted with the cell binding agent; M' is the residue of a linking group that together with one of the reacted linking groups of BFCG forms a thioether, a disulfide, a thioester, an amide, an imine, a —O-imine or a hydrazone moiety; and BFCG is linked to the CB through a thioether, a disulfide, a thioester, an amide, an imine, a —O-imine or a hydrazone moiety.

In a sixth embodiment the invention relates to a compound comprising a derivatized maytansinol or maytansinol analog residue and a linking group that can form a chemical bond to a cell binding agent or a bifunctional crosslinking reagent, wherein the derivatized maytansinol or maytansinol analog residue is represented by formula (VI):

MayO-A- (VI);

or a pharmaceutically acceptable salt or solvate thereof, wherein: MayO is a residue of maytansinol or maytansinol analog represented by MayOH; A is an optional group selected from C=O, C(=O)NR', and C(=O)O; and R' is selected from H, substituted or unsubstituted linear, branched, or cyclic alkyl, alkenyl or alkynyl, and substituted or unsubstituted aryl; provided the compound does not comprise a N-methyl alanine or N-methylcysteine moiety represented by the following formula:

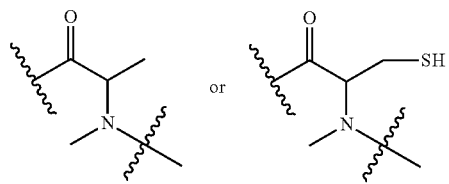

directly connected to MayO—.

In a seventh embodiment the invention relates to a compound comprising a derivatized maytansinol or maytansinol analog residue wherein the derivatized maytansinol or maytansinol analog is represented by the following formula (VII):

MayO-A-Y- (VII);

wherein: MayO and A are as described in the sixth embodiment; and Y is an optional group selected from a substituted or unsubstituted linear, branched, or cyclic alkyl, alkenyl or alkynyl, a substituted or unsubstituted aryl, a substituted or unsubstituted heterocyclic group, a substituted or unsubstituted arylalkyl, a substituted or unsubstituted heterocyclylalkyl group, an aziridine group and an epoxy group, wherein each of the alkyl, alkenyl, alkynyl, arylalkyl and heterocyclylalkyl groups is optionally interrupted by one or more group selected from a polyethylene glycol unit $(OCH_2CH_2)_n$, an aziridine group, an epoxy group, an amino group, an amido group, an ester group, an aryl group and a heterocyclic group an amino acid and a peptide wherein: n is an integer from 1 to 200.

In an eighth embodiment the invention relates to a compound of formula (VIII):

MayO-A-Y-L (VIII);

or a pharmaceutically acceptable salt or solvate thereof, wherein: MayO, A and Y are as defined in the sixth and seventh embodiments; and L is a linking group that can form a chemical bond to a cell binding agent or a bifunctional crosslinking reagent.

In a ninth embodiment the invention relates to a compound, represented by formula (IX):

MayO-A-Y-L (IX);

wherein: MayO, A and L are as defined in the sixth, seventh and eighth embodiments; and Y is an optional group selected from a substituted or unsubstituted linear, branched, or cyclic alkyl, alkenyl or alkynyl, a substituted or unsubstituted aryl, a substituted or unsubstituted heterocyclic group, each bearing an optional polyethylene glycol unit $(OCH_2CH_2)_n$, wherein n is an integer from 1 to 200, and a peptide; and L is a functional group can that form a chemical bond to a cell binding agent via a disulfide bond, thioether bond, peptide bond, amide bond, ester bond or a hydrazone bond, or pharmaceutically acceptable salts or solvates of the compound, provided that when A is C=O, Y together with A is not N-methylalanine or N-methylcysteine moiety.

In a tenth embodiment the invention relates to a compound comprising a bifunctional crosslinking reagent linked to a derivatized maytansinol or maytansinol analog residue represented by the formula (X):

MayO-A- (X);

or a pharmaceutically acceptable salt or solvate thereof, wherein: MayO is a residue of maytansinol or maytansinol analog represented by MayOH; A is an optional group selected from C=O, C(=O)NR', and C(=O)O; R' is selected from H, substituted or unsubstituted linear, branched, or cyclic alkyl, alkenyl or alkynyl, and substituted or unsubstituted aryl; provided that the compound does not comprise a N-methylalanine or N-methylcysteine moiety represented by the following formula:

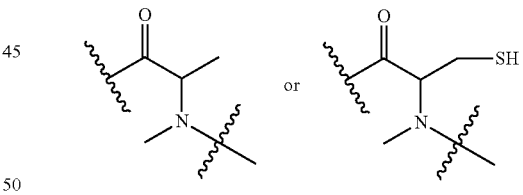

directly connected to MayO—.

In an eleventh embodiment the invention relates to a compound comprising a bifunctional crosslinking reagent linked to a derivatized maytansinol or maytansinol analog residue represented by the formula (XI):

MayO-A-Y- (XI);

wherein: MayO and A are as defined in the tenth embodiment; and Y is an optional group selected from a substituted or unsubstituted linear, branched, or cyclic alkyl, alkenyl or alkynyl, a substituted or unsubstituted aryl, a substituted or unsubstituted heterocyclic group, a substituted or unsubstituted arylalkyl, a substituted or unsubstituted heterocyclylalkyl group, an aziridine group, and an epoxy group, wherein each of the alkyl, alkenyl, alkynyl, arylalkyl and heterocyclylalkyl group is optionally interrupted by one or more group selected from a polyethylene glycol unit $(OCH_2CH_2)_n$, an aziridine group, an epoxy group, an amino group, an amido group, an ester group, an aryl group and a heterocyclic group, an amino acid and a peptide, wherein: n is an integer from 1 to 200.

In a twelfth embodiment the invention relates to a compound comprising a bifunctional crosslinking reagent linked to a derivatized maytansinol or maytansinol analog residue wherein the compound is represented by formula (XII):

MayO-A-Y-M'-BFCG'-Z'    (XII);

or pharmaceutically acceptable salt or solvate thereof, wherein: MayO, A and Y are as defined in the tenth and eleventh embodiments; and BFCG'-Z' is the residue of a bifunctional crosslinking reagent comprising two linking groups, wherein one of the linking groups is represented by Z' and the other has reacted with M'; Z' is a linking group that can be linked to a cell binding agent via a thioether, a disulfide, a thioester, an amide, a thioester, an imine, a —O-imine- or a hydrozone moiety; M' is the residue of a linking group that together with one of the reacted group of BFCG' forms a thioether, a disulfide, a thioester, an amide, an imine, a —O-imine or a hydrazone moiety.

In a thirteenth embodiment the invention relates to methods of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal comprising administering to said mammal a therapeutically effective amount of the conjugate of formulae I-V and, optionally, a chemotherapeutic agent.

In fourteenth embodiment the invention relates to pharmaceutical compositions of the cell binding agent conjugates of formulae I-V and a pharmaceutically acceptable carrier, additive or diluent thereof.

BRIEF DESCRIPTION OF THE FIGURES

FIG. 1 shows the structures of maytansinol and previously described maytansinoids. In Y', l, m, n, o, p, q, r, s, t and u are each independently 0 or an integer of from 1 to 5, provided that at least two of l, m, n, o, p, q, r, s, t and u are not zero at any one time; and Z is H, SR or —COR, wherein R is linear alkyl or alkenyl having from 1 to 10 carbon atoms, branched or cyclic alkyl or alkenyl having from 3 to 10 carbon atoms, unsubstituted or substituted aryl group or substituted or unsubstituted heterocyclic group. In the linkable maytansinoids, Z and $Z_1$ have the same definition as Z for Y'.

FIG. 2 shows the structures of ansamitocins and maytansine.

FIG. 3 shows the in vitro cytotoxicity of maytansine compared with ansamitocins with different ester groups towards A) KB cells and B) SK-Br-3 cells.

FIG. 5 shows the synthesis of disulfide and thiol-containing ansamitocin derivatives.

FIG. 7 shows the synthesis of a disulfide and a thiol-containing pegylated ansamitocin derivative.

FIG. 8 shows the synthesis of an ansamitocin derivative bearing a peptidase labile linker.

FIG. 9 shows the synthesis of ansamitocin derivatives bearing a carbonyl group.

FIG. 10 shows the synthesis of ansamitocin derivatives bearing an amino group.

FIG. 11 shows the synthesis of ansamitocin derivatives bearing an N-hydroxysuccinimidyl ester group.

FIG. 12 shows the synthesis of ansamitocin derivatives bearing an ether group, a carbamate group or a carbonate group.

FIG. 13 shows the synthesis of thiol-containing ansamitocins.

FIG. 14 shows a conjugation procedure for a disulfide-linked conjugate prepared with compounds of the present invention.

FIG. 15 shows a conjugation procedure for a thiosuccinimidyl-linked conjugate prepared with compounds of the present invention.

FIG. 16 shows a conjugation procedure for a thioacetamidyl-linked conjugate prepared with compounds of the present invention.

FIG. 17 shows a conjugation procedure for a peptidase-labile conjugate prepared with compounds of the present invention.

FIG. 18 shows a conjugation procedure for a peptidase-labile thiosuccinimidyl-linked conjugate prepared with compounds of the present invention.

FIG. 19 shows a conjugation procedure for a peptidase-labile thioacetamidyl-linked conjugate prepared with compounds of the present invention.

FIG. 20 shows a conjugation procedure for an amide-linked conjugate prepared with compounds of the present invention.

FIG. 21 shows a conjugation procedure for a hydrazone-linked conjugate prepared with compounds of the present invention.

FIG. 22 shows a conjugation procedure for a hydrazone-linked conjugate prepared with compounds of the present invention.

FIG. 23 shows a conjugation procedure for a hydrazone-linked conjugate prepared with compounds of the present invention.

FIG. 25 shows a conjugation procedure for a disulfide-linked conjugate prepared with compounds of the present invention.

FIG. 26 shows conjugation procedures for a thioether-linked conjugate prepared with compounds of the present invention.

FIG. 27 shows a conjugation procedure for an amide-linked conjugate prepared with compounds of the present invention.

FIG. 28 shows in-vitro activity of prepared ansamitocin derivatives against the KB cell line (96 hour exposure).

FIG. 29. shows in-vitro activity of prepared ansamitocin derivatives against the COLO 205 cell line (96 hour exposure).

FIG. 30. shows in-vitro activity of prepared ansamitocin derivatives against the COLO 205-MDR cell line (96 hour exposure).

FIG. 31. shows in-vitro activity of conjugates prepared with linkable ansamitocin derivatives and the thiol-bearing maytansinoid, DM1, against COLO 205 cells.

DETAILED DESCRIPTION OF THE INVENTION

Figure 4A:
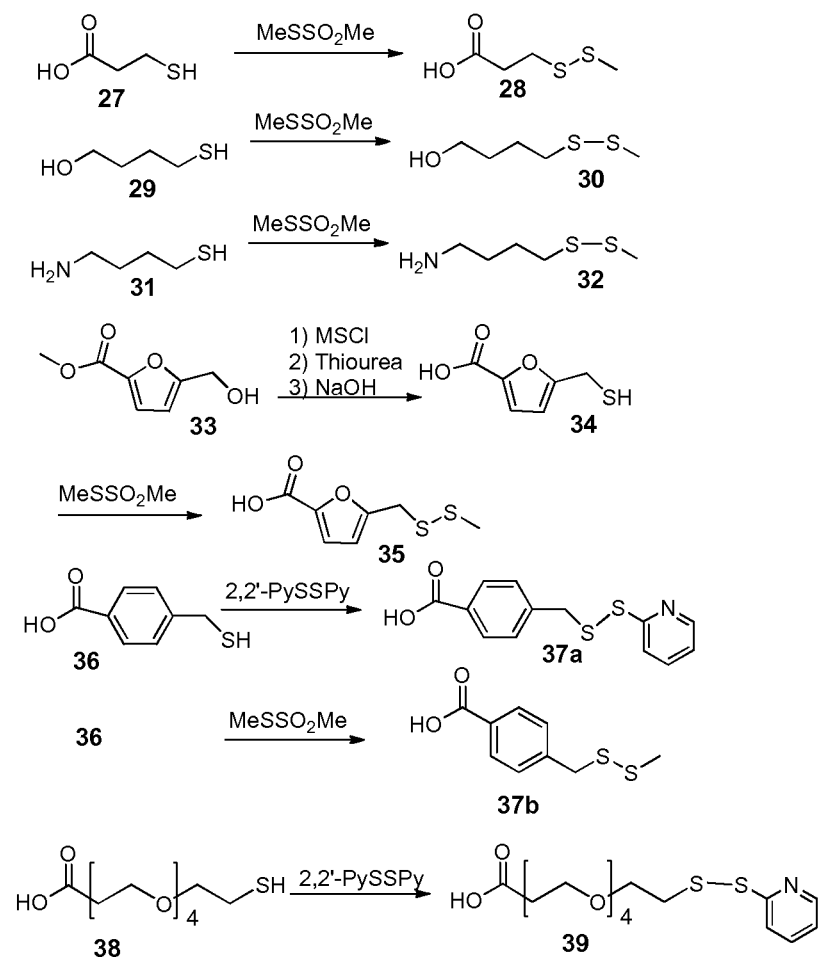
FIG. 4 shows the synthesis of side chains.

This invention discloses new ansamitocin derivatives bearing a functional group that allows for linkage to a cell binding agent. In addition, this invention discloses the preparation of conjugates of these novel ansamitocin derivatives with cell-binding agents.

Another aspect of the invention is a pharmaceutical composition comprising an effective amount of any of the above-described ansamitocin derivative-cell-binding agent conjugates, a pharmaceutically acceptable salt or solvate thereof and a pharmaceutically acceptable carrier, diluent or excipient.

The above-described pharmaceutical composition comprising an ansamitocin derivative, may further comprise an antibody.

An even further aspect of the invention is a method of inducing cell death in selected cell populations comprising contacting target cells or tissue containing target cells with an effective amount of any of the above-described ansamitocin derivative-cell-binding agents, salts or solvates thereof.

The art reveals that it is extremely difficult to modify existing drugs without diminishing their cytotoxic potential. The disclosed invention overcomes this problem by teaching a method of synthesizing new ansamitocin derivatives bearing a functional group. The disclosed novel ansamitocin derivatives preserve, and in some cases even enhance, the cytotoxic potency of the previously described ansamitocins.

The ansamitocin derivative-cell-binding agent conjugates permit the full measure of the cytotoxic action of the ansamitocin derivatives to be applied in a targeted fashion against unwanted cells only, thereby avoiding side effects due to damage to non-targeted healthy cells. Thus, the invention provides useful agents, and novel methods for making the same, for the elimination of diseased or abnormal cells that are to be killed or lysed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

Ansamitocin precursors that can be used in the present invention, to produce the ansamitocin derivatives that are capable of being linked to a cell-binding agent, are well known in the art and can be isolated from natural sources according to known methods or prepared synthetically according to known methods (see U.S. Pat. Nos. 6,790,954; 7,192,750; 7,432,088).

Examples of suitable ansamitocin precursors include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamitocin P2);

(2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−C-19-dechloro (U.S. Pat. No. 4,294,757) (prepared by acylation using acyl chlorides).

Specific examples of suitable analogues of maytansinol having modifications of other positions include:

(1) C9-SH (U.S. Pat. No. 4,424,219) (prepared by the reaction of maytansinol with $H_2S$ or $P_2S_5$);

(2) C14-alkoxymethyl (demethoxy/$CH_2OR$) (U.S. Pat. No. 4,331,598);

(3) C14-hydroxymethyl or acyloxymethyl ($CH_2OH$ or $CH_2OAc$) (U.S. Pat. No. 4,450,254) (prepared from *Nocardia*);

(4) C15-hydroxy/acyloxy (U.S. Pat. No. 4,364,866) (prepared by the conversion of maytansinol by *Streptomyces*);

(5) C15-methoxy (U.S. Pat. Nos. 4,313,946 and 4,315,929) (isolated from *Trewia nudiflora*);

(6) C18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

Many positions on maytansinol can serve as the position to chemically link the linking moiety. For example, the C-3 position having a hydroxyl group, the C-14 position modified with hydroxymethyl, the C-15 position modified with hydroxy and the C-20 position having a hydroxy group are all useful. However the C-3 and C-20 positions is preferred and the C-3 position of maytansinol is especially preferred.

The synthesis of esters of maytansinol having a linking moiety is described below in terms of some exemplary linking moieties at the C-3 position, one of skill in the art will understand that linking moieties with other chemical bonds, as described above, can also be used with the present invention, as can other ansamitocins and other linking positions, as described above.

In the structural formulas described herein (for example, formulas I-XII in the first to twelfth embodiments), alternate values for the variables are provided below.

In a first (1) alternative embodiment, Y in structural formulas II-V, VII-IX, XI and XII is an optional group selected from $C_{1-6}$alkyl, $C_{2-6}$alkenyl, $C_{2-6}$alkynyl, halo$C_{1-6}$alkyl, $C_{1-6}$alkyl having a halogen and a hydroxyl group on two adjacent carbon atoms,

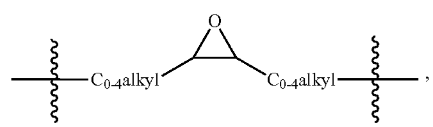

,

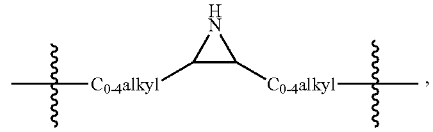

,

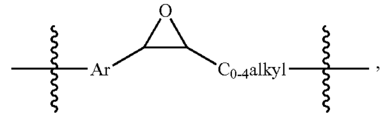

,

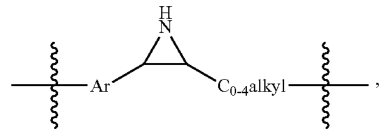

,

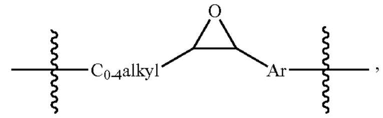

,

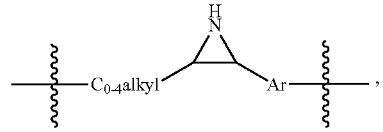

, —$C_{2-}$ alkenyl-Ar—, —Ar—$C_{2-6}$alkenyl-, —$C_{2-6}$alkynyl-Ar—, —Ar—$C_{2-6}$alkynyl-, —$C_{1-6}$alkyl-Ar— having a halogen and a hydroxyl group on two adjacent carbon atoms of the $C_{1-6}$alkyl and —Ar—$C_{1-6}$alkyl having a halogen and a hydroxyl group on two adjacent carbon atoms, wherein Ar is an optionally substituted aryl or an optionally substituted heterocyclyl and the alkenyl, alkynyl, alkyl in the groups represented by Y are optionally substituted.

In a second (2) alternative embodiment, Ar in the first alternative embodiment is a phenyl group optionally substituted with $C_{1-4}$alkyl, $C_{1-4}$alkoxy, hydroxy$C_{1-4}$alkyl, halo$C_{1-4}$alkyl, —OH, —OC(=O)—$C_{1-4}$alkyl, —OC(=O)—$C_{1-4}$alkyl-NR$^a$R$^b$, —$C_{1-4}$alkyl-COOH, —NR$^a$R$^b$, —$C_{1-4}$alkyl-NR$^a$R$^b$, —NO$_2$ and halogen, wherein R$^a$ and R$^b$ are each independently H, $C_{1-4}$alkyl or an amino protecting group or R$^a$ and R$^b$ together with the nitrogen atom forms a heterocyclic ring having one or more heteroatoms.

In a third (3) alternative embodiment -A-Y— in structural formulas II-V, VII-IX, XI and XII is represented by one of the following formula:

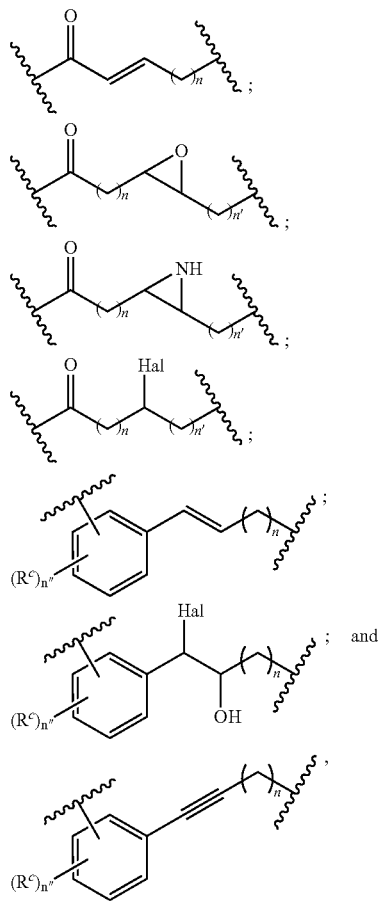

wherein n and n' are each independently 0, 1, 2 or 3; n" is 1, 2 or 3 and R$^c$ for each occurrence is H, $C_{1-4}$alkyl, $C_{1-4}$alkoxy, hydroxy$C_{1-4}$alkyl, halo$C_{1-4}$alkyl, —OH, —OC(=O)—$C_{1-4}$alkyl, —OC(=O)—$C_{1-4}$alkyl-NR$^a$R$^b$, —$C_{1-4}$alkyl-COOH, —NO$_2$ and halogen, wherein R$^a$ and R$^b$ are each independently H, $C_{1-4}$alkyl, amino$C_{1-4}$alkyl or an amino protecting group or R$^a$ and R$^b$ together with the nitrogen atom forms a heterocyclic ring having one or more heteroatoms.

In a fourth (4) alternative embodiment R$^a$ and R$^b$ in the second and third alternative embodiments together with the nitrogen atom forms an optionally substituted piperazinyl, an optionally substituted protected piperazinyl or an optionally substituted 4-piperidinopiperidinyl (e.g.,

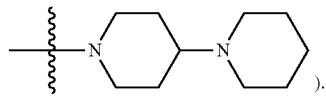).

In a fifth (5) alternative embodiment n" is 1 or 2 and R$^c$ is H, methyl, ethyl, halogen, —CF$_3$, —NO$_2$, —OMe, —CO$_2$Me, —OH, —CH$_2$OH, —CH$_2$OC(O)CH$_2$NH$_2$, —CH$_2$OC(O)(C(CH$_3$)$_2$)CH$_2$NH$_2$, —CH$_2$NH$_2$, —CH$_2$N(CH$_3$)$_2$, —CH$_2$COOH, and —CH$_2$-piperizinyl in alternative embodiments 2-4.

In a sixth (6) alternative embodiment Y in structural formulas II-V, VII-IX, XI and XII is represented by the formula (IA):

$$—[Ar']_j—(C_{1-10}alkyl)- \qquad (IA);$$

wherein: Ar' is an optionally substituted aryl, an optionally substituted heterocyclyl, an optionally substituted $C_{1-4}$alkylaryl, or an optionally substituted $C_{1-4}$alkylheterocyclyl; and j is 0 or 1.

In a seventh (7) alternative embodiment Y in structural formulas II-V, VII-IX, XI and XII is represented by formula (IIA):

$$—[Ar'']_{0-1}—(CR^1R^2)_x—B—W-D-(CR^1R^2)_w— \qquad (IIA);$$

wherein: Ar" is phenyl, —CH$_2$-phenyl, heterocyclyl, or —CH$_2$-heterocyclyl, optionally substituted with one to four groups selected from, alkyl, alkoxyl, halo, haloalkyl, alkoxyhaloalkyl, nitrile and nitro; each R$^1$ and R$^2$ is independently hydrogen or $C_{1-4}$alkyl; B is NR", O or absent; W is an amino acid or a peptide comprising 2 to 8 amino acids, (OCH$_2$CH$_2$)$_n$ or absent; D is CO, NR" or absent; R" is selected from H, substituted or unsubstituted linear, branched, or cyclic alkyl, alkenyl or alkynyl, and substituted or unsubstituted aryl; x is an integer from 1 to 10; w is 0 or an integer from 1 to 10; and n is an integer from 1 to 200.

In an eighth (8) alternative embodiment R" in structural formula IIA is H or $C_{1-4}$alkyl.

In a ninth (9) alternative embodiment Y in structural formulas II-V, VII-IX, XI and XII and alternative embodiments 1-8 is —(CR$^1$R$^2$)$_x$—, x is an integer from 1 to 6.

In a tenth (10) alternative embodiment each R$^1$ and R$^2$ in structural formulas II-XII and alternative embodiments 1-9 are independently hydrogen or methyl.

In an eleventh (11) alternative embodiment Y in structural formulas II-V, VII-IX, XI and XII is represented by one of the following formula:

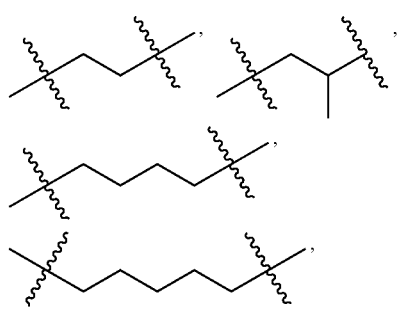

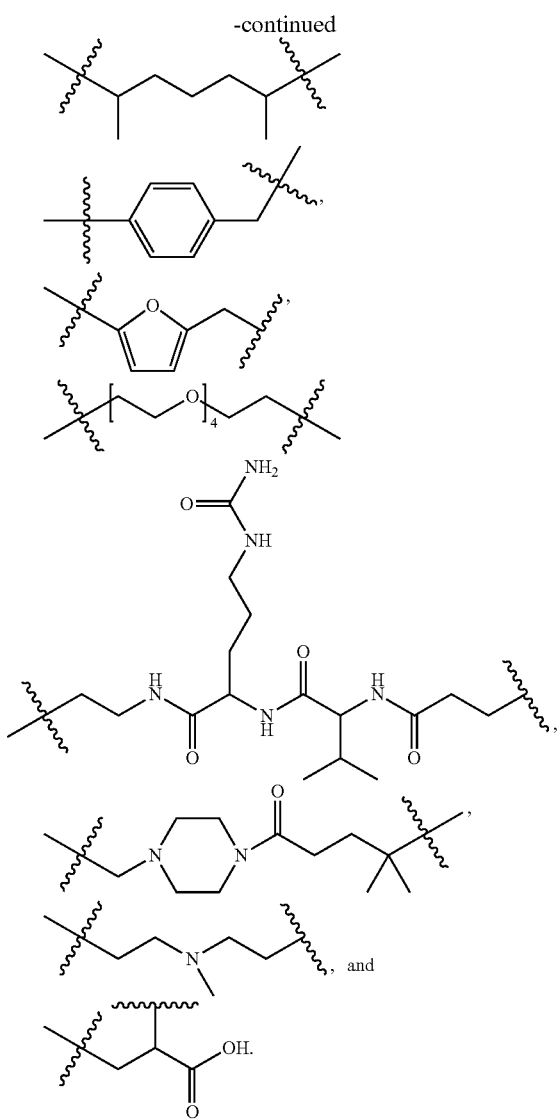

In a twelfth (12) alternative embodiment R' in formulas I-XII and alternative embodiments 1-11 is H or $C_{1-4}$alkyl.

In a thirteenth (13) alternative embodiment MayO in formulas I-XII and alternative embodiments 1-12 is represented by the formula:

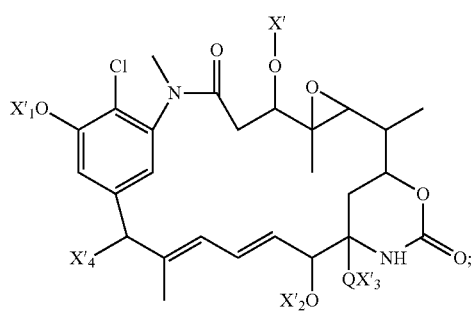

wherein: $X'_4 = X'_5$ or $OX'_5$, and $X'$, $X'_1$, $X'_2$, $X'_3$, and $X'_5$ are the same or different and are selected from R, C(=O)R, C(=O)NR$_2$ or C(=O)OR, wherein: each R is independently selected from H, substituted or unsubstituted linear, branched, or cyclic alkyl, alkenyl or alkynyl, and substituted or unsubstituted aryl; Q is selected from O or S; provided that at least one of $X'$, $X'_1$, $X'_2$, $X'_3$, $X'_5$ represents a covalent bond between MayO and A or AY.

In a fourteenth (14) alternative embodiment R in the thirteenth alternative embodiment is independently H or $C_{1-4}$alkyl.

In a fifteenth (15) alternative embodiment MayO in formulas I-XII and alternative embodiments 1-14 is represented by the formulae:

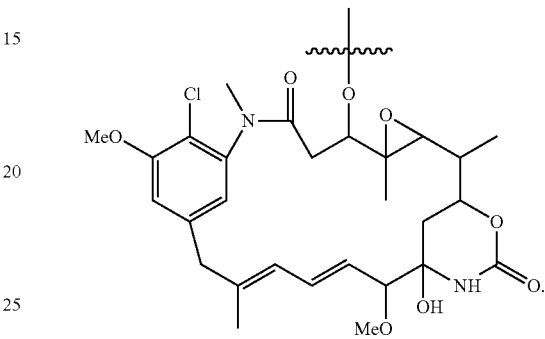

In a sixteenth (16) alternative embodiment BFCG in formula V comprises a moiety M" connected to M' and a moiety Z connected to CB, wherein M" and Z are each independently selected from the group consisting of —C(=O)—, —C(=O)—NR$^e$—, —C(=O)—O—, —O—C(=O)—, —C(=NH)—, —C(=NH)—NR$^e$—, —S—, —NH—NR$^e$—,

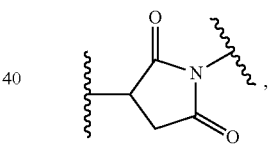

—C(=NR$^e$)—, =NNR$^e$—, —CH$_2$—C(=O)—, and —CH$_2$—C(=O)—NR$^e$—, wherein R$^e$ is H, an alkyl, an alkenyl or an alkylnyl and the rest of the variables are as described in alternative embodiments 1-15.

In a seventeenth (17) alternative embodiment M" and Z in the sixteenth alternative embodiment are each independently selected from the group consisting of —C(=O)—,

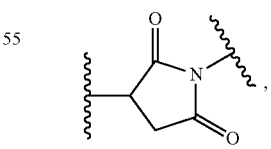

—S—, —CH$_2$—C(=O)—, —CH$_2$—C(=O)—NH— and —O—C(=O)—, and the rest of the variables are as described in alternative embodiments 1-15.

In an eighteenth (18) alternative embodiment M'-M" in the sixteenth alternative embodiment is represented by a structural formula selected from:

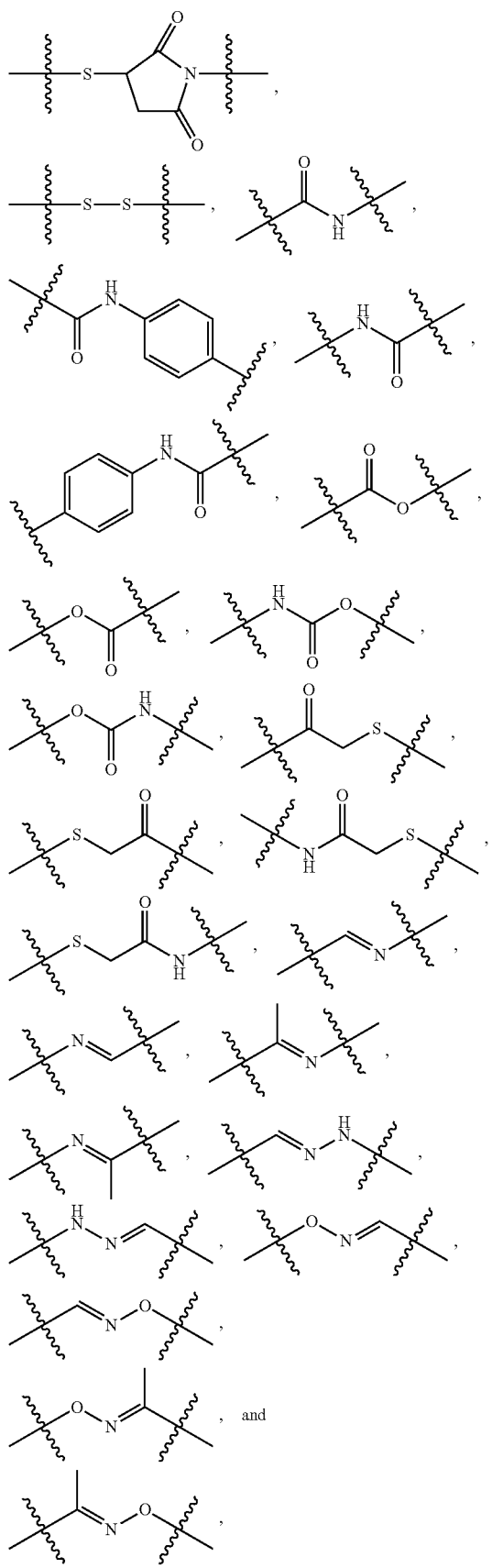

and the remainder of the variables are as described in alternative embodiments 1-17.

In a nineteenth (19) alternative embodiment —BFCG- in formula V is represented by formula (IIIA):

$$-M''-(CR^3R^4)_{y'}-[Cy]_{0\ or\ 1}-C(O)— \qquad (IIIA);$$

or a pharmaceutically acceptable salt or solvate thereof, wherein: M'' is

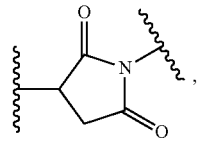 [SMILES: *C1CC(=O)N(*)C1=O]

each $R^3$ and $R^4$ is independently hydrogen, methyl or $—SO_3^-M^+$, wherein: $M^+$ is $H^+$ or a pharmaceutically acceptable cation; Cy is a cycloalkyl or a phenyl optionally substituted with one to four groups selected from, alkyl, alkoxyl, halo, haloalkyl, alkoxy haloalkyl, nitrile and nitro; and y is 0 or an integer from 1 to 10 and the remainder of the variables are as described in alternative embodiments 1-18.

In a twentieth (20) alternative embodiment BFCG in formula V is

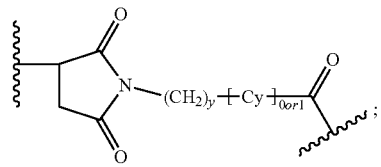

and M' is —S— and the remainder of the variables are as described in alternative embodiments 1-19 and the rest of the variables are as described in alternative embodiments 1-19.

In a twenty-first (21) alternative embodiment BFCG in formula V is:

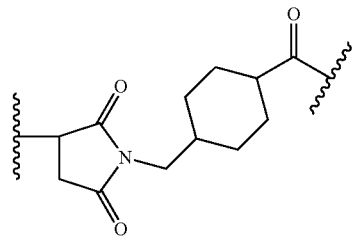 [SMILES: *C(=O)C1CCC(CN2C(=O)CC(*)C2=O)CC1]

and the remainder of the variables are as described in alternative embodiments 1-20.

In a twenty-second (22) alternative embodiment —BFCG- of formula V is represented by formula (IVA):

$$—S—(CR^3R^4)_{y'}—C(O)— \qquad (IVA);$$

wherein: each $R^3$ and $R^4$ is independently hydrogen, methyl or $—SO_3^-M^+$, wherein: $M^+$ is $H^+$ or a pharmaceutically acceptable cation y' is an integer from 1 to 10 and the remainder of the variables are as described in alternative embodiments 1-18.

In a twenty-third (23) alternative embodiment the invention relates to a cell binding agent conjugate wherein BFCG comprises a self-immolative moiety and the rest of the variables are as described in alternative embodiments 1-22.

In a twenty-fourth (24) alternative embodiment BFCG in formula V is represented by the following formula:

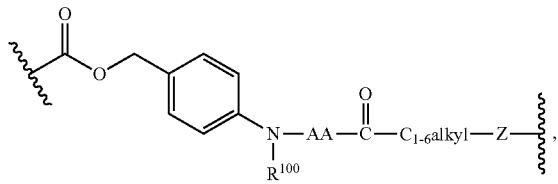

wherein AA is an amino acid or a peptide comprising 2 to 8 amino acids, $R^{100}$ is H or an alkyl, and the rest of the variables are as described in alternative embodiments 1-18. Alternatively, BFCG in formula V is represented by the following formula:

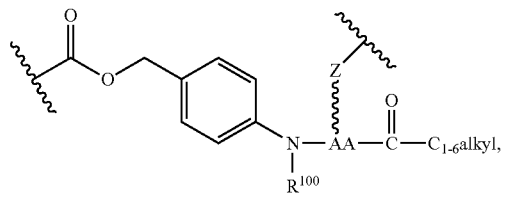

wherein AA is an amino acid or a peptide comprising 2 to 8 amino acids, wherein one of the amino acid side chain having a linking moiety Z described herein (e.g., —NH—, —C(=O)—) that is covalently linked to a cell-binding agent and $R^{100}$ is H or an alkyl. In another alternative, BFCG in formula V is -AA-(C=O)$_{0-1}$—C$_{0-6}$alkyl-Z—, wherein AA is an amino acid or a peptide comprising 2 to 8 amino acids and Z is a linking group; or BFCG in formula V is

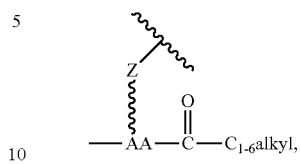

wherein AA is an amino acid or a peptide comprising 2 to 8 amino acids, wherein one of the amino acid side chain having a linking moiety Z described herein (e.g., —NH—, —C(=O)—) that is covalently linked to a cell-binding agent.

In a twenty-fifth alternative (25) embodiment AA in alternative embodiment 24 is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Gly-Gly-Gly (SEQ ID NO:4), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, and D-Arg-D-Arg and the rest of the variables are as described in alternative embodiments 1-18.

In a twenty-sixth (26) alternative embodiment AA in alternative embodiments 24-25 is Gly-Gly-Gly, Val-Cit, Phe-Lys or Val-Lys and the rest of the variables are as described in alternative embodiments 1-18.

In a twenty-seventh (27) alternative embodiment BFCG in formula V is selected from:

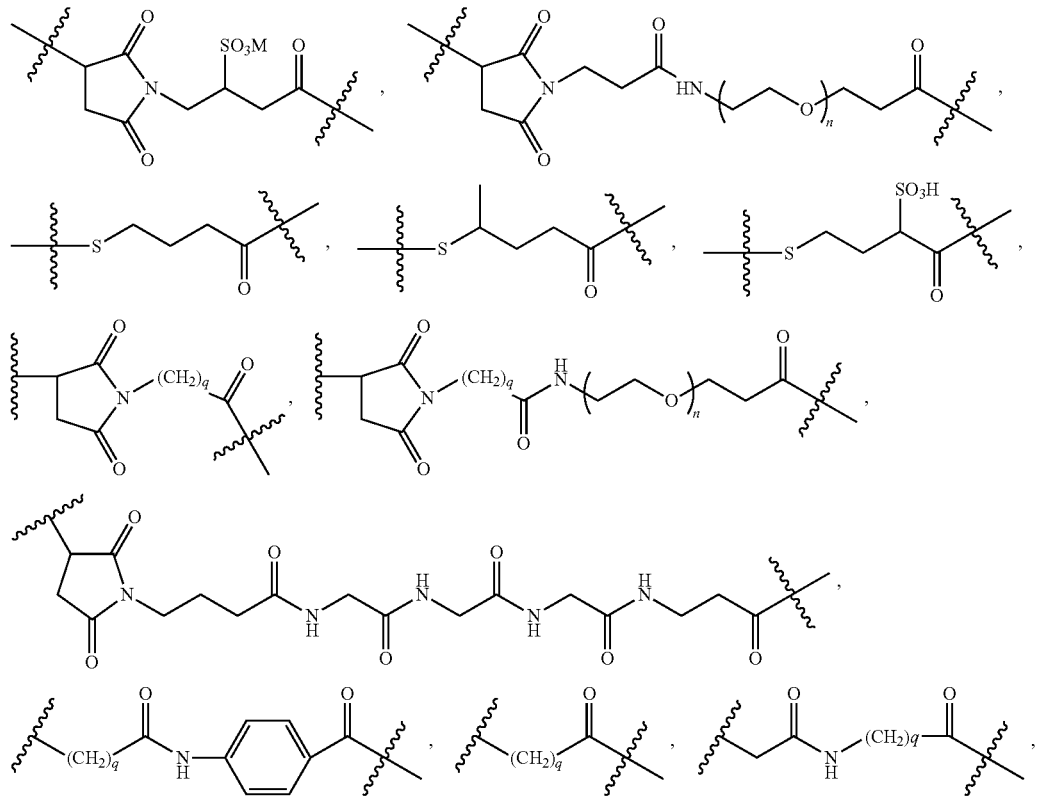

-continued

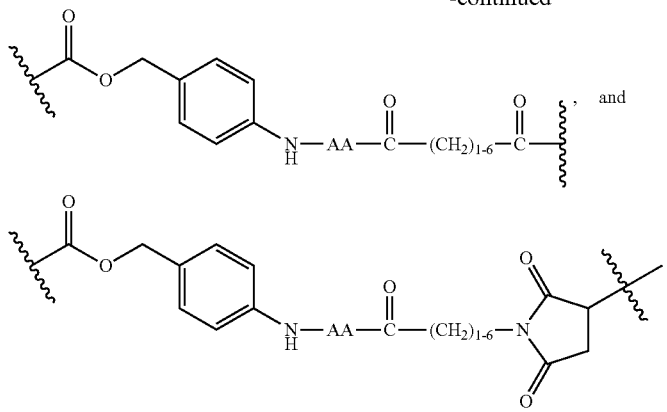

wherein: AA is Val-Cit, Phe-Lys or Val-Lys, q is an integer from 1 to 5; n is an integer from 1 to 20; and M is $H^+$ or a pharmaceutically acceptable cation and the rest of the variables are as described in alternative embodiments 1-18.

In a twenty-eighth (28) alternative embodiment the cell-binding agent in formulas III-V binds to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, STEAP, TENB2, MUC16, IRTA1, IRTA2, IRTA3, IRTA4, IRTA5, c-MET, 5T4, or Her-2 antigens; Her-3 antigens or cells expressing insulin growth factor receptor, epidermal growth factor receptor, and folate receptor and the rest of the variables are as described in alternative embodiments 1-27.

In a twenty-ninth (29) alternative embodiment the cell-binding agent of formulas III-V is an antibody, a single chain antibody, an antibody fragment that specifically binds to the target cell, a monoclonal antibody, a single chain monoclonal antibody, or a monoclonal antibody fragment that specifically binds the a target cell, a chimeric antibody, a chimeric antibody fragment that specifically binds to the target cell, a domain antibody, a domain antibody fragment that specifically binds to the target cell, a diabody, a nanobody, a probody, a Darpin, a lymphokine, a hormone, a vitamin, a growth factor, a colony stimulating factor, or a nutrient-transport molecule and the rest of the variables are as described in alternative embodiments 1-27.

In a thirtieth (30) alternative embodiment the antibody in alternative embodiment 29 is a resurfaced antibody, a resurfaced single chain antibody, or a resurfaced antibody fragment and the rest of the variables are as described in alternative embodiments 1-27.

In a thirty-first (31) alternative embodiment the antibody in alternative embodiment 29 is a monoclonal antibody, a single chain monoclonal antibody, or a monoclonal antibody fragment thereof and the rest of the variables are as described in alternative embodiments 1-27.

In a thirty-second (32) alternative embodiment the antibody in alternative embodiment 29 is a humanized antibody, a humanized single chain antibody, or a humanized antibody fragment and the rest of the variables are as described in alternative embodiments 1-27.

In a thirty-third (33) alternative embodiment the cell binding agent conjugate of formulas I-V and exemplary embodiments 1-32 is formulated as a pharmaceutical composition with a pharmaceutically acceptable carrier.

In a thirty-fourth (34) alternative embodiment the compound formulas VI-IX is represented by the structural formulae 2-5:

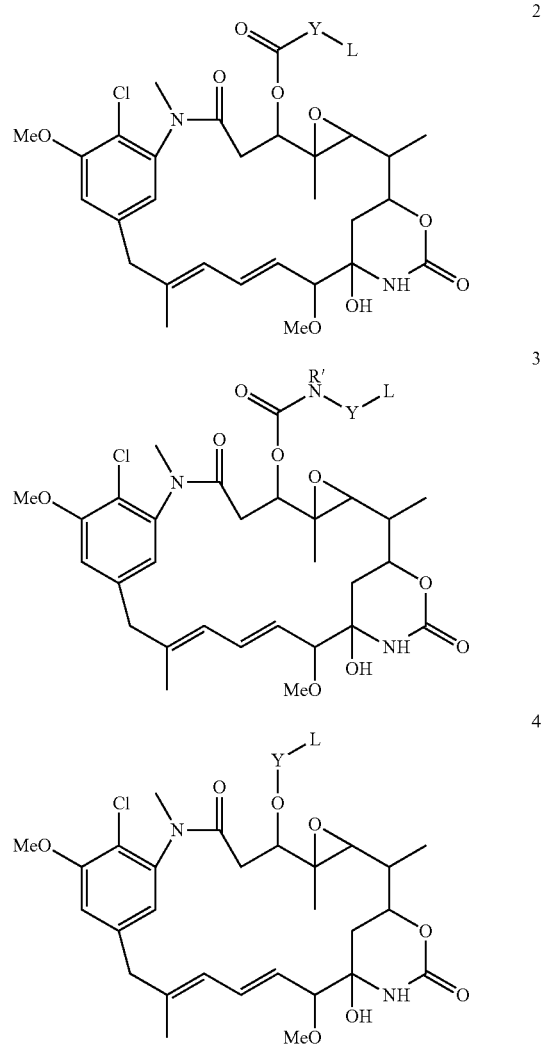

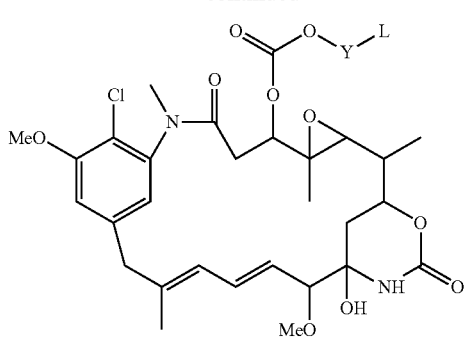

wherein, R' is selected from H, substituted or unsubstituted linear, branched, or cyclic alkyl, alkenyl or alkynyl and substituted or unsubstituted aryl; Y is an optional group selected from a substituted or unsubstituted linear, branched, or cyclic alkyl, alkenyl or alkynyl, a substituted or unsubstituted aryl, a substituted or unsubstituted heterocyclic group, each bearing an optional polyethylene glycol unit $(OCH_2CH_2)_n$, wherein n is an integer from 1 to 200, and a peptide; L is a functional group that forms a link to a cell binding agent via a disulfide bond, thioether bond, peptide bond, amide bond, ester bond or a hydrazone bond, or pharmaceutically acceptable salts or solvates of the ansamitocin derivatives and the rest of the variables are as defined in alternative embodiments 1-15.

In a thirty-fifth (35) alternative embodiment L in formulas VIII-IX and alternative embodiment 34 is represented by a structural formula selected from a maleimide, a haloacetamido, —SH, —SSR$^d$, —CH$_2$SH, —CH(Me)SH, —C(Me)$_2$SH, —NHR$^f$, —CH$_2$NHR$^f$, —NR$^f$NH$_2$, —COOH, and —COE, wherein COE represents a reactive ester, R$^d$ is an optionally substituted phenyl or an optionally substituted pyridyl and R$^f$ is H or an alkyl and the rest of the variables are as defined in alternative embodiments 1-15.

In a thirty-sixth (36) alternative embodiment the reactive ester represented by —COE in alternative embodiment 35 is selected from N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester, and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl) and the rest of the variables are as defined in alternative embodiments 1-15.

In a thirty-seventh (37) alternative embodiment the compound of formulas VI-IX and exemplary embodiments 34-36 is represented by any one of compounds 6 to 26, or a pharmaceutically acceptable salt or solvate thereof:

6

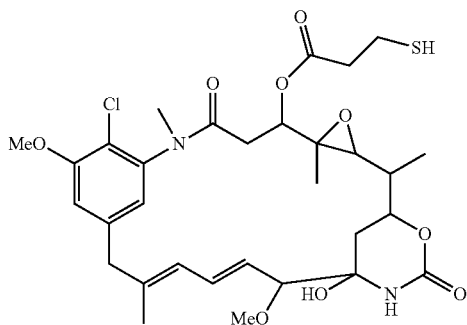

7

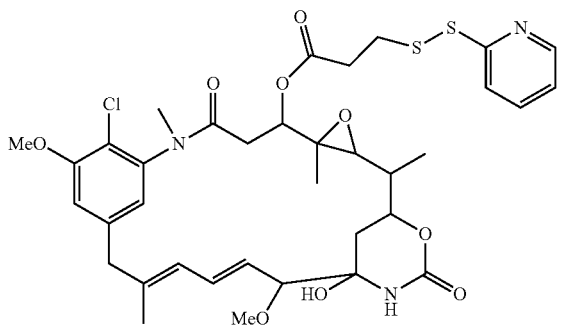

8

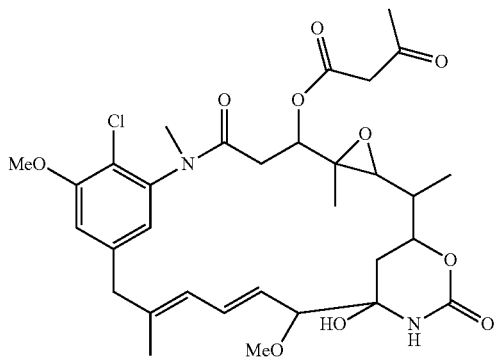

9

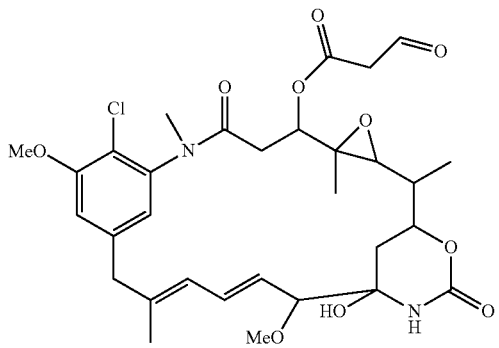

10
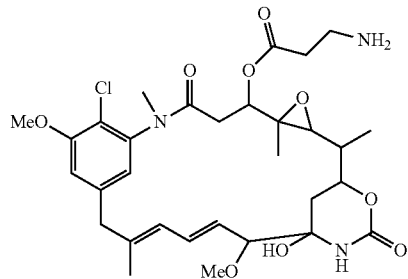
13
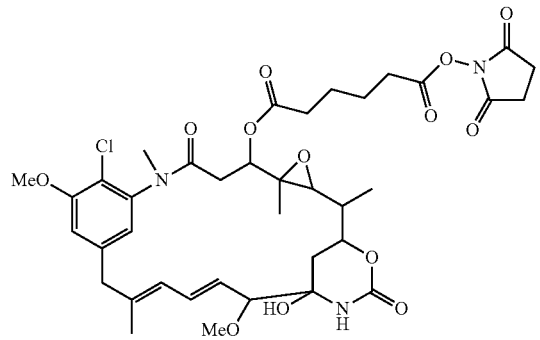
14
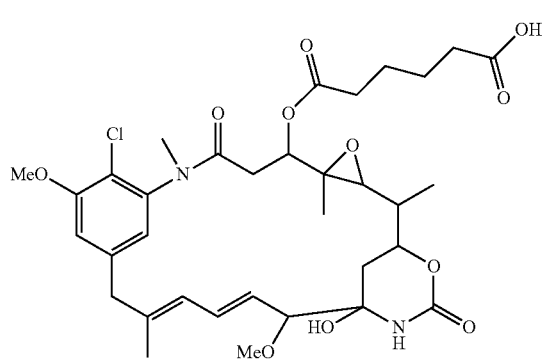
15
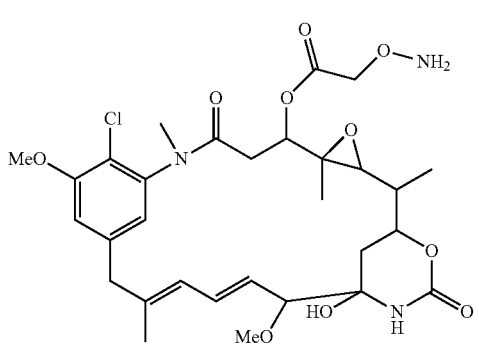
16
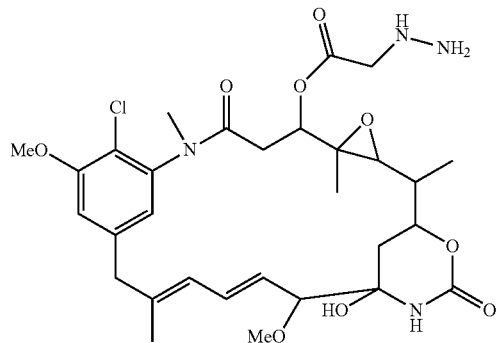
17
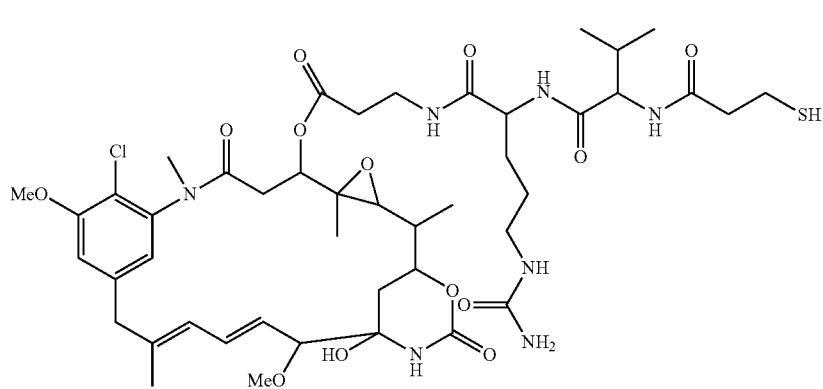

-continued
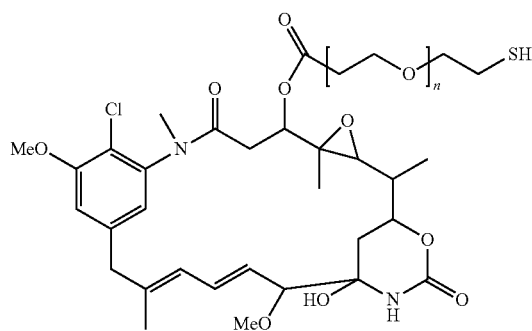
18
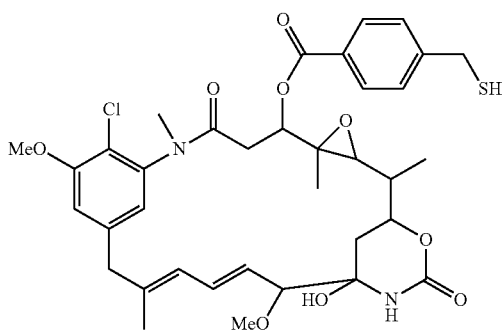
19
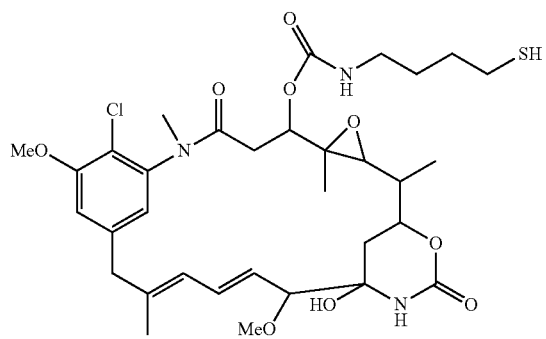
20
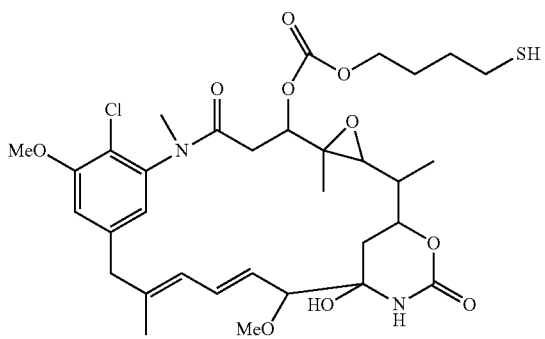
21
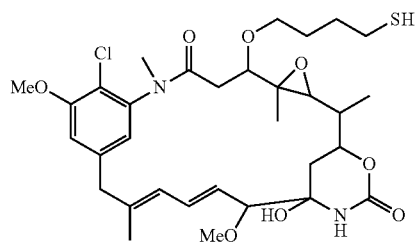
22
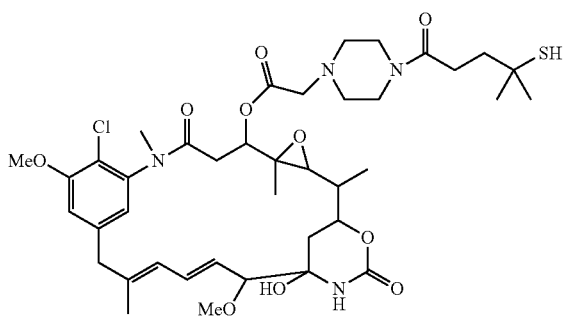
23
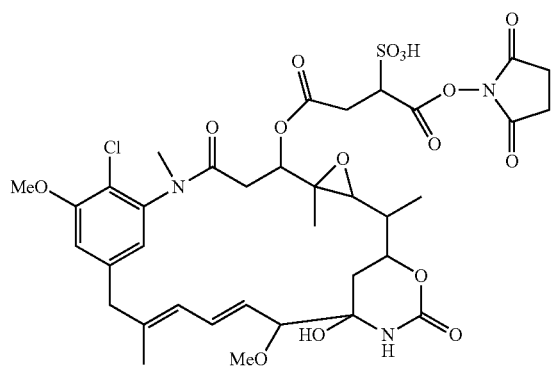
24
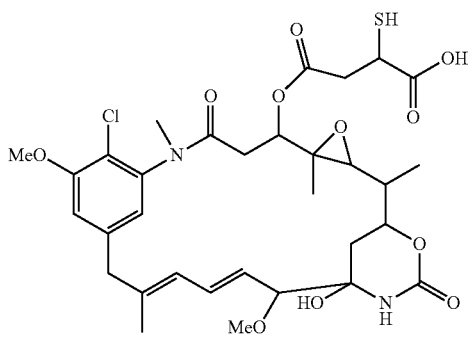
25

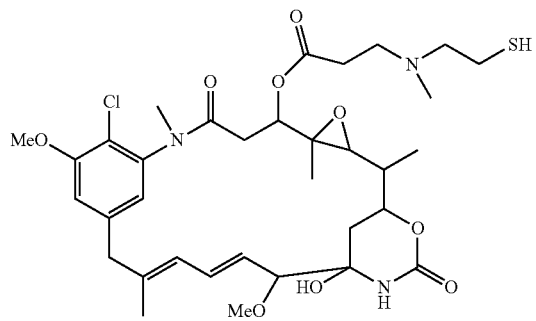
26
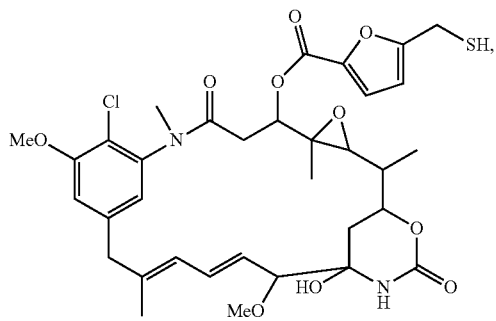
46
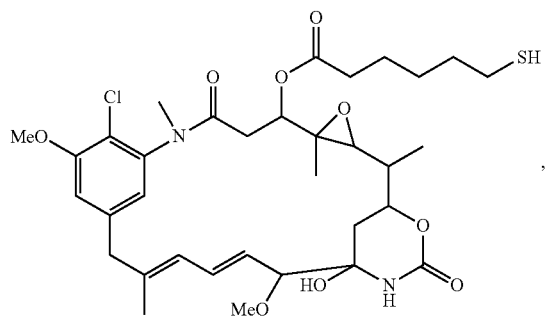
55
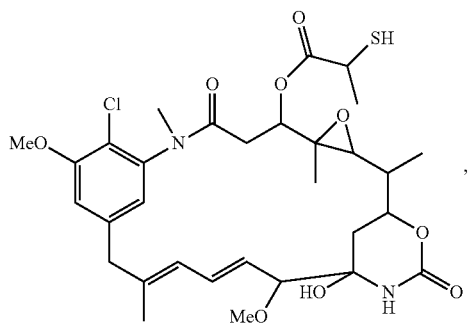
58
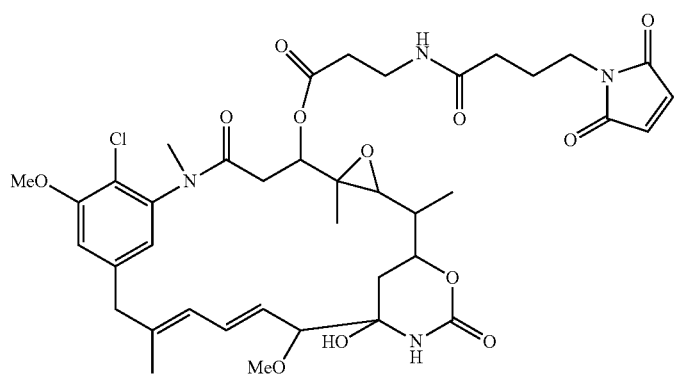
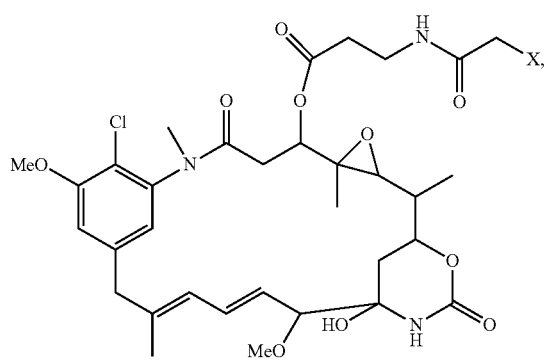
X = I, Br, Cl or F -continued
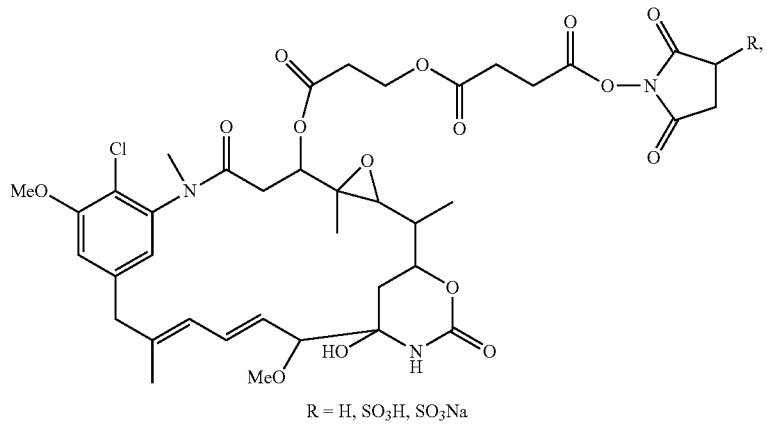
R = H, SO₃H, SO₃Na
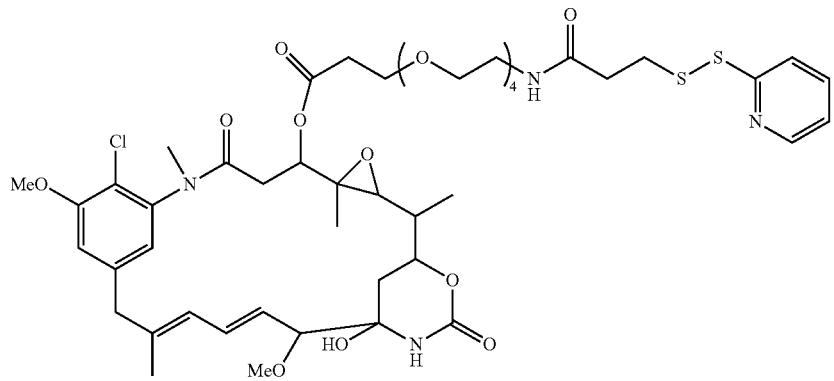
60
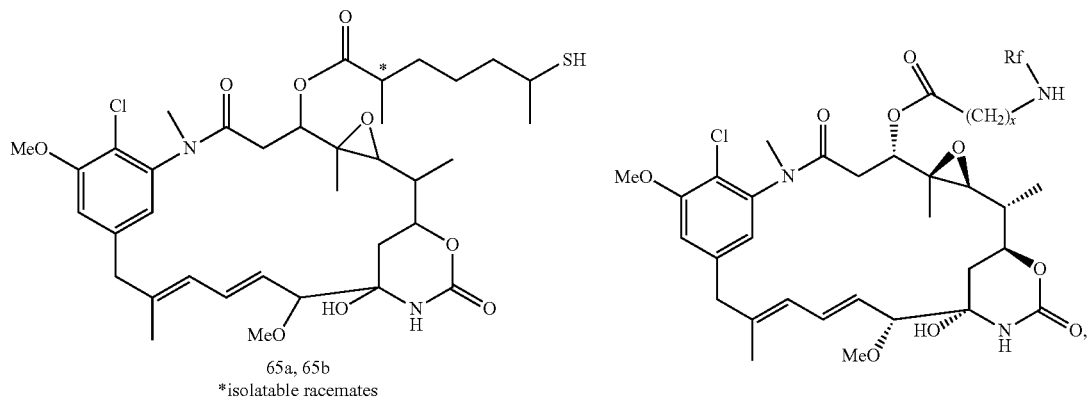
65a, 65b
*isolatable racemates
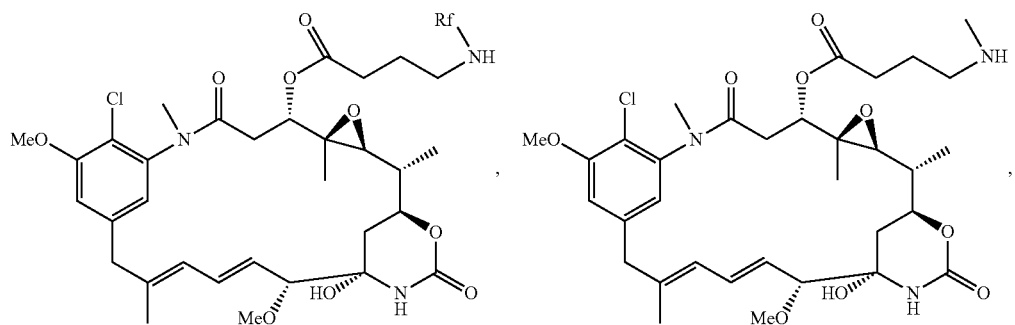

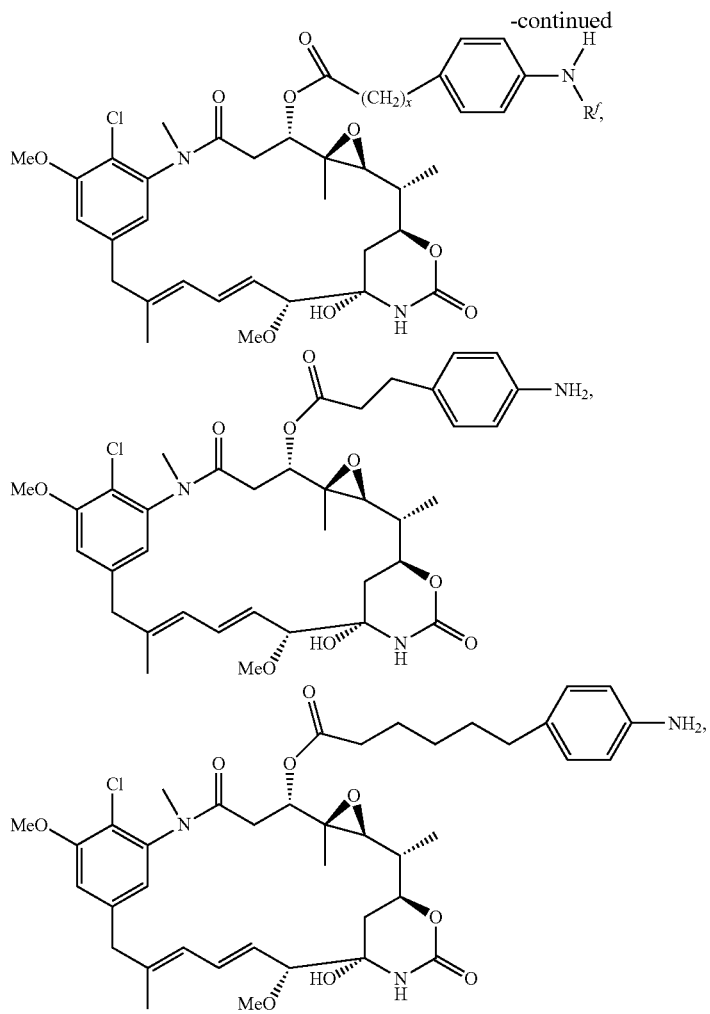

wherein x is an integer from 1 to 6; and $R^f$ is H or an alkyl.

In a thirty-eighth (38) alternative embodiment BFCG' in formula XII comprises a linking group M" connected to M', wherein M" is independently selected from the group consisting of —C(=O)—, —C(=O)—NR$^e$—, —C(=O)—O—, —O—C(=O)—, —C(=NH)—, —C(=NH)—NR$^e$—, —S—, —NR$^e$—, —NH—NR$^e$—,

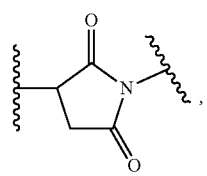 [SMILES: *C1CC(=O)N(*)C1=O]

—C(=NR$^e$)—, =NNR$^e$—, —CH$_2$—C(=O)—, and —CH$_2$—C(=O)—NR$^e$—, wherein R$^e$ is H, an alkyl, an alkenyl or an alkylnyl and the rest of the variables are as defined in alternative embodiments 1-15.

In a thirty-ninth (39) alternative embodiment M" in alternative embodiment 38 is selected from the group consisting of —C(=O)—,

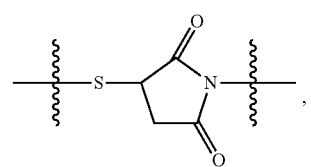

—S—, —CH$_2$—C(=O)—, —CH$_2$—C(=O)—NH— and —O—C(=O)— and the rest of the variables are as defined in alternative embodiments 1-15.

In a fortieth (40) alternative embodiment M'-M" in alternative embodiments 38 is represented by a structural formula selected from:

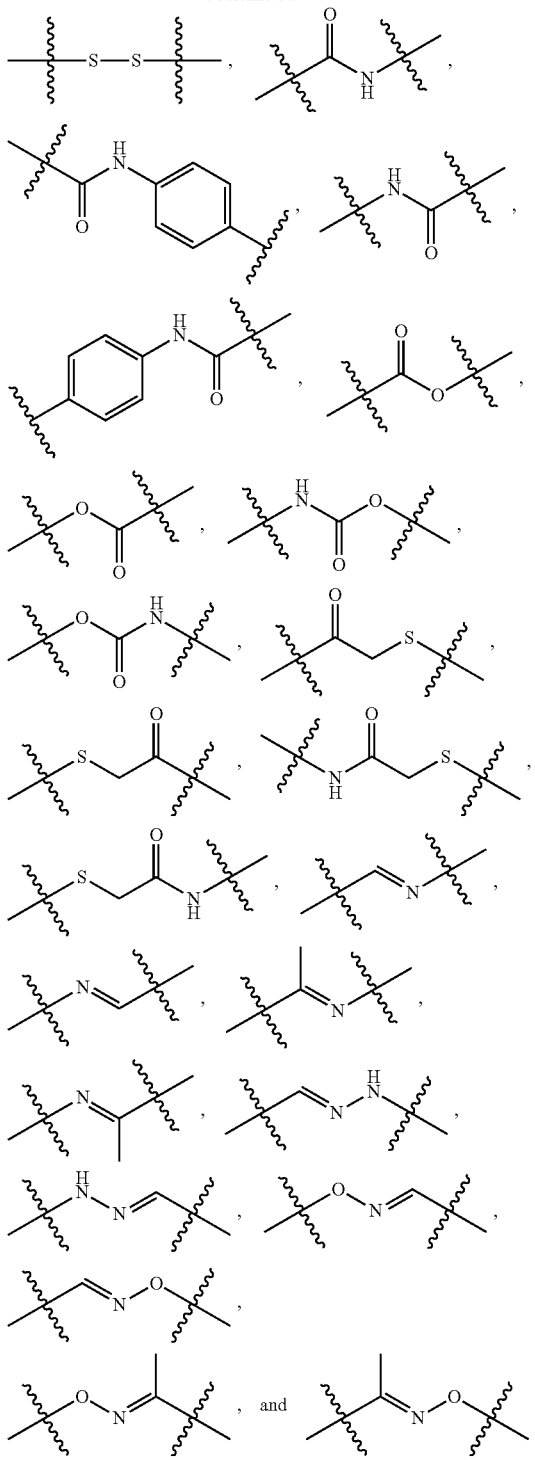

and the rest of the variables are as defined in alternative embodiments 1-15.

In a forty-first (41) alternative embodiment BFCG' in formula XII is represented by formula (IIIC):

$$-M''-(CR^3R^4)_{y'}-[Cy]_{0\ or\ 1}- \qquad (IIIC);$$

or a pharmaceutically acceptable salt or solvate thereof, wherein M'' is,

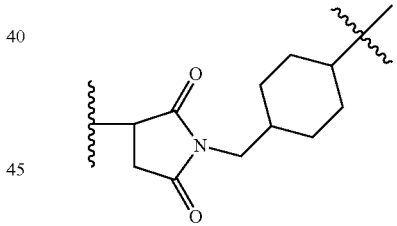

each $R^3$ and $R^4$ is independently hydrogen, methyl or $-SO_3^-$ $M^+$, wherein $M^+$ is a $H^+$ or a pharmaceutically acceptable cation; Cy is a cycloalkyl or phenyl optionally substituted with one to four groups selected from, alkyl, alkoxyl, halo, haloalkyl, alkoxy haloalkyl, nitrile and nitro; and y is 0 or an integer from 1 to 10 and the rest of the variables are as defined in alternative embodiments 1-15.

In a forty-second (42) alternative embodiment BFCG' in formula XII and alternative embodiment 38-41 is and M' is —S— and the rest of the variables are as defined in alternative embodiments 1-15.

In a forty-third (43) alternative embodiment BFCG' in formula XIII and alternative embodiments 38-42 is and the rest of the variables are as defined in alternative embodiments 1-15.

In a forty-fourth (44) alternative embodiment —BFCG'- in formula XII is represented by formula (IVC):

$$-S'''-(CR^3R^4)_{y'}, \qquad (IVC);$$

wherein: each $R^3$ and $R^4$ is independently hydrogen, methyl or $-SO_3^-M^+$, wherein: $M^+$ is $H^+$ or a pharmaceutically acceptable cation y' is an integer from 1 to 10 and the rest of the variables are as defined in alternative embodiments 1-15.

In a forty-fifth (45) alternative embodiment BFCG' in formula XII comprises a self-immolative moiety and the rest of the variables are as defined in alternative embodiments 1-15.

In a forty-sixth (46) alternative embodiment the BFCG' in formula XII is represented by the following formula:

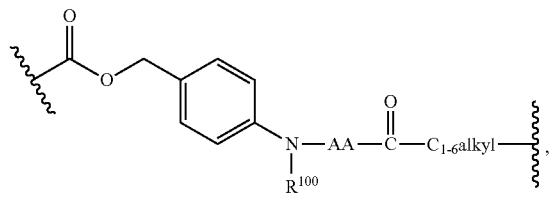

wherein AA is an amino acid or a peptide comprising 2 to 8 amino acids, $R^{100}$ is H or an alkyl, and the rest of the variables are as defined in alternative embodiments 1-15. Alternatively, BFCG'-Z' in formula XII is represented by the following formula:

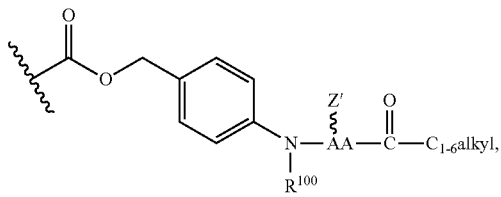

wherein AA is an amino acid or a peptide comprising 2 to 8 amino acids, wherein one of the amino acid side chain having a linking group Z' described above (e.g., —NH$_2$, —COOH or —COE) that can be covalently linked to a cell-binding agent and $R^{100}$ is H or an alkyl. In another alternative, BFCG' in formula V is -AA-(C=O)$_{0-1}$—C$_{0-6}$alkyl-, wherein AA is an amino acid or a peptide comprising 2 to 8 amino acids; or BFCG'-Z' in formula V is $$-AA-\overset{Z'}{\underset{}{\vert}}-\overset{O}{\underset{}{C}}-C_{1-6}alkyl,$$

wherein AA is an amino acid or a peptide comprising 2 to 8 amino acids, wherein one of the amino acid side chain having a linking group Z' described above (e.g., —NH$_2$ or —COE) that can be covalently linked to a cell-binding agent.

In a forty-seventh (47) alternative embodiment AA in alternative embodiment 46 is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Gly-Gly-Gly (SEQ ID NO:4), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, and D-Arg-D-Arg and the rest of the variables are as defined in alternative embodiments 1-15.

In a forty-eighth (48) alternative embodiment AA in alternative embodiments 46-47 is Gly-Gly-Gly, Val-Cit, Phe-Lys or Val-Lys and the rest of the variables are as defined in alternative embodiments 1-15.

In a forty-ninth (49) alternative embodiment BFCG' in formula XII is selected from:

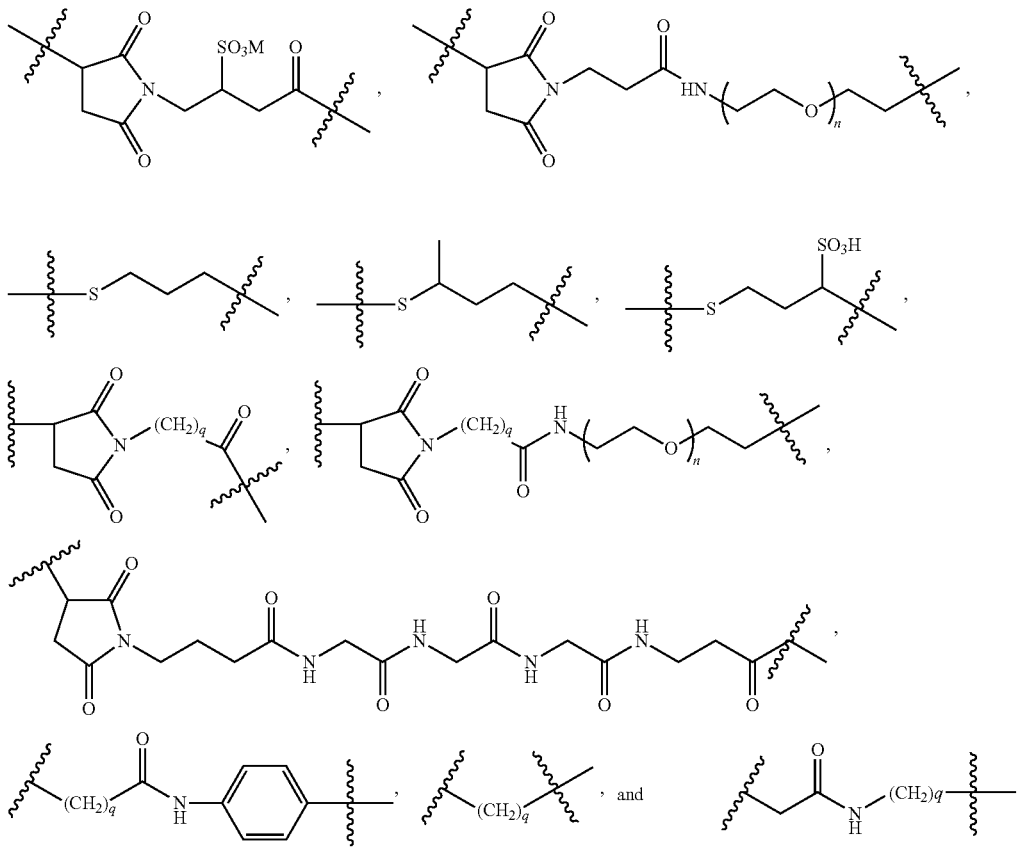

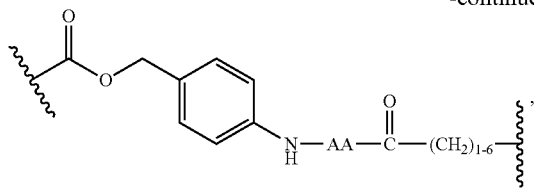

wherein: AA is Val-Cit, Phe-Lys or Val-Lys, q is an integer from 1 to 5; n is an integer from 1 to 20; and M is H⁺ or a pharmaceutically acceptable cation and the rest of the variables are as defined in alternative embodiments 1-15.

In an fiftieth (50) alternative embodiment Z' in formula XII is selected from the group consisting of a maleimide, a haloacetamido, —SH, —SSR$^d$, —CH$_2$SH, —CH(Me)SH, —C(Me)$_2$SH, —NHR$^c$, —CH$_2$NHR$^c$, —NR$^c$NH$_2$, —COOH, and —COE, wherein COE represents a reactive ester, R$^d$ is an optionally substituted phenyl or an optionally substituted pyridyl and R$^f$ is H or an alkyl and the rest of the variables are as defined in alternative embodiments 1-49.

In a fifty-first (51) alternative embodiment COE in alternative embodiment 50 is selected from N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5, 6-tetrafluorophenyl) ester, and pentafluorophenyl ester, and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl) and the rest of the variables are as defined in alternative embodiments 1-49.

In a fifty-second (52) alternative embodiment the chemotherapeutic agent of the thirteenth embodiment is administered to said mammal sequentially or consecutively.

In a fifty-third (53) alternative embodiment the method of the thirteenth embodiment and alternative embodiment 52 is for treating a condition selected from cancer, rheumatoid arthritis, multiple sclerosis, graft versus host disease (GVHD), transplant rejection, lupus, myositis, infection, and immune deficiency.

In a fifty-fourth (54) alternative embodiment the method of the thirteenth embodiment and alternative embodiment 52 is for treating cancer.

In a fifty-fifth (55) alternative embodiment the method of the thirteenth embodiment and alternative embodiment 52 and 54 is a method of treating cancer wherein the cancer is selected from breast cancer, colon cancer, brain cancer, prostate cancer, kidney cancer, pancreatic cancer, ovarian cancer, head and neck cancer, melanoma, colorectal cancer, gastric cancer, squamous cancer, small-cell lung cancer, non small-cell lung cancer, testicular cancer, Merkel cell carcinoma, glioblastoma, neuroblastoma, and cancers of lymphatic organs.

In another embodiment, MayO-A-Y-M'-BFCG in formula V is represented by the following formula:

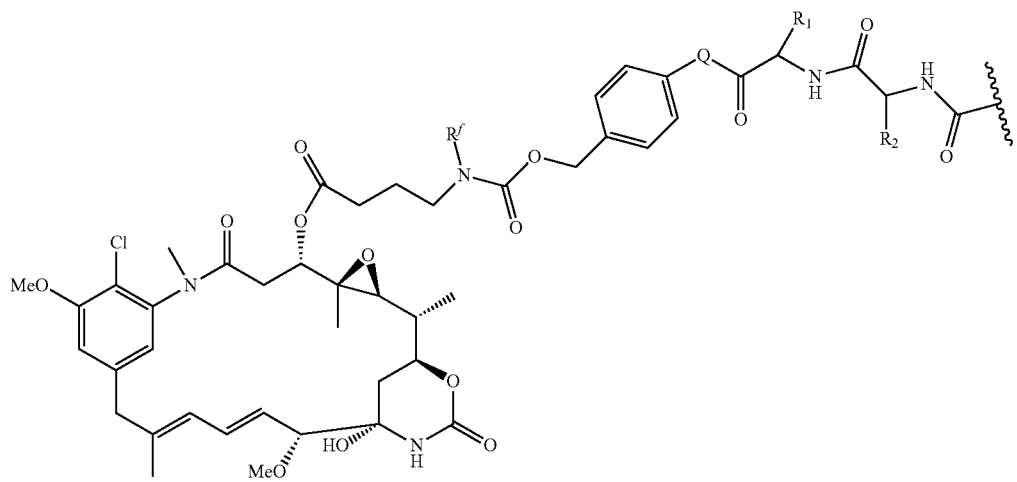

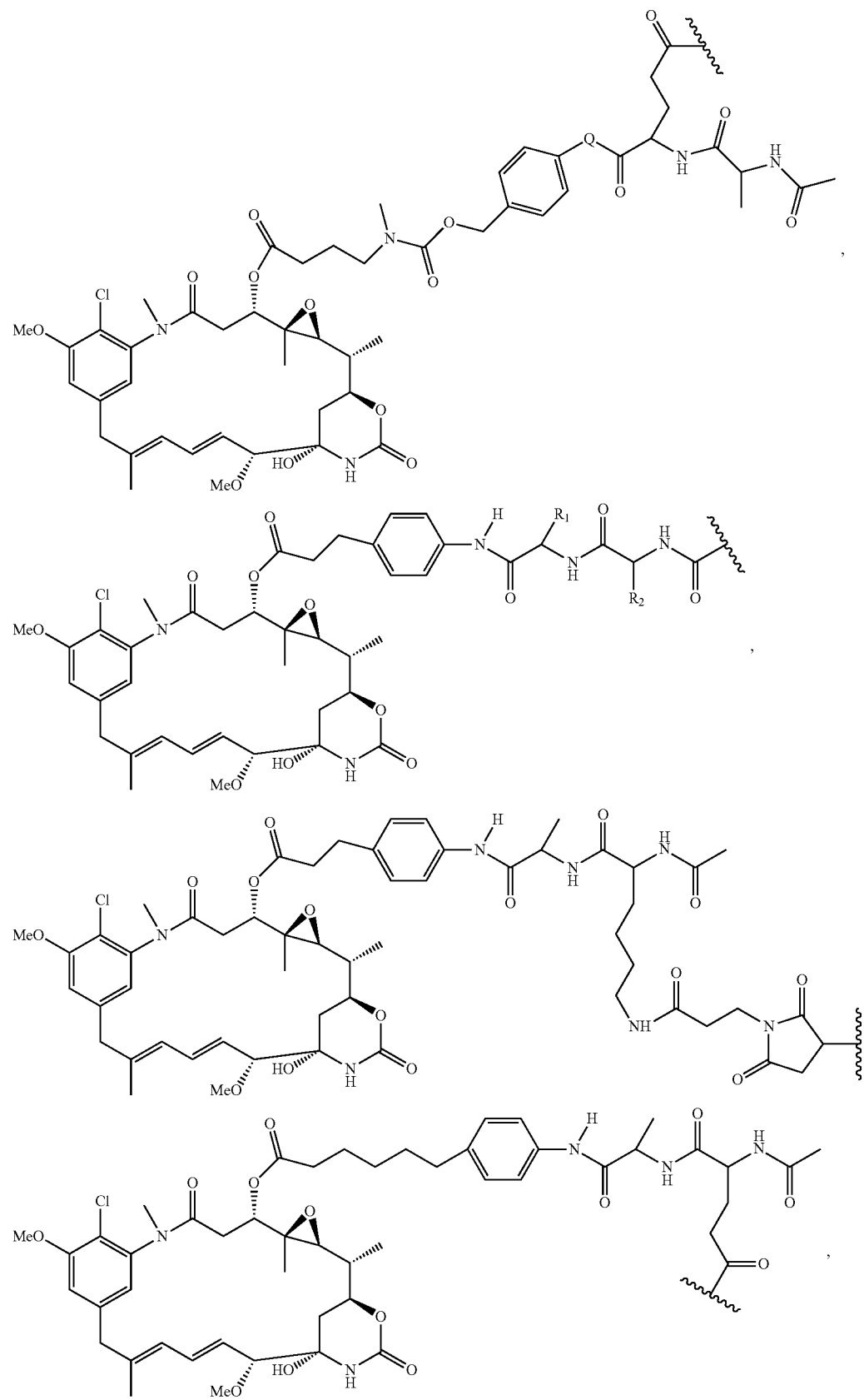

wherein $R^f$ is H or an alkyl; Q is —O— or —NR$^{100}$; R$^{100}$ is H or an alkyl; and $R_1$ and $R_2$ are each independently an amino acid side chain.

As used herein, a "bifunctional crosslinking reagent" refers to a reagent that possesses two reactive groups; one of which is capable of reacting with a cell-binding agent, while the other one is capable of reacting with the cytotoxic agent to link the cell-binding agent with the cytotoxic agent (for example, compounds of formula (VI)-(IX)), thereby forming a conjugate.

Any suitable bifunctional crosslinking reagent can be used in connection with the invention, so long as the linker reagent provides for retention of the therapeutic, e.g., cytotoxicity, and targeting characteristics of the cytotoxic agent and the cell-binding agent, respectively, without undue toxicity. Preferably, the linker molecule joins the cytotoxic agent to the cell-binding agent through chemical bonds (as described above), such that the cytotoxic agent and the cell-binding agent are chemically coupled (e.g., covalently bonded) to each other. The bifunctional crosslinking reagents that can be used for making the drug-linker compounds of the present invention also include those described in *Thermo Scientific Pierce Crosslinking Technical Handbook*, the entire teaching of which is incorporated herein by reference.

In one embodiment, the bifunctional crosslinking reagent comprises non-cleavable linkers. A non-cleavable linker is any chemical moiety that is capable of linking a cytotoxic agent (for example, compounds of formula (VI)-(IX)) to a cell-binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the cytotoxic agent or the cell-binding agent remains active.

Suitable crosslinking reagents that form non-cleavable linkers between a cytotoxic agent and the cell-binding agent are well known in the art. In one embodiment, the cytotoxic agent is linked to the cell-binding agent through a thioether bond. Examples of non-cleavable linkers include linkers having a maleimido- or haloacetyl-based moiety for reaction with the cytotoxic agent. Such bifunctional crosslinking reagents are well known in the art (see US Patent Application Publication Nos. 2010/0129314, 2009/0274713, 2008/0050310, 20050169933, 2009/0274713, 2010/0129314, and those available from Pierce Biotechnology Inc. P.O. Box 117, Rockland, Ill. 61105, USA) and include, but not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), α-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-((β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy) sulfosuccimido ester (sulfo-EMCS), N-κ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal. Preferably, the bifunctional crosslinking reagent is SMCC.

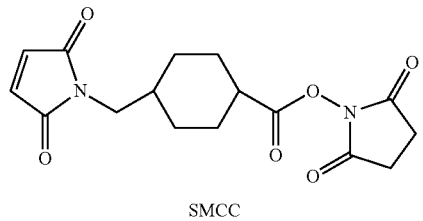

SMCC

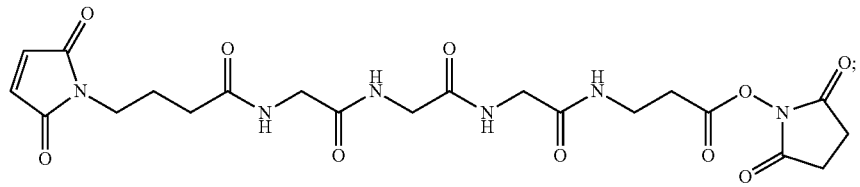

(CX1-1)

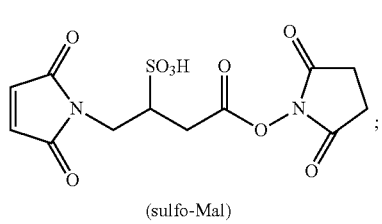

(sulfo-Mal)

n = 2 to 20 (e.g., 2, 4, 6, 8)

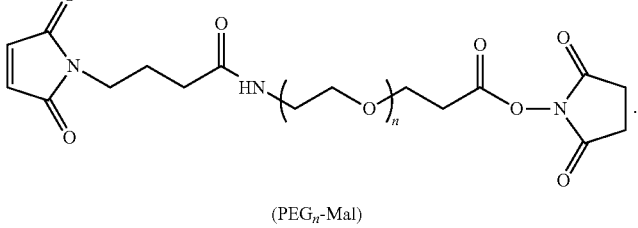

(PEG$_n$-Mal)

In one embodiment, the linking reagent is a cleavable linker. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., *Proc. Natl. Acad. Sci. USA,* 79: 626-629 (1982), and Umemoto et al., *Int. J. Cancer,* 43: 677-684 (1989)). In one embodiment, the cleavable linker is cleaved under mild conditions, i.e., conditions within a cell under which the activity of the cytotoxic agent is not affected.

In another embodiment, the cytotoxic agent is linked to a cell-binding agent through a disulfide bond. The linker molecule comprises a reactive chemical group that can react with the cell-binding agent. Preferred reactive chemical groups for reaction with the cell-binding agent are N-succinimidyl esters and N-sulfosuccinimidyl esters. Additionally the linker molecule comprises a reactive chemical group, preferably a dithiopyridyl group, that can react with the cytotoxic agent to form a disulfide bond. Bifunctional crosslinking reagents that enable the linkage of the cell-binding agent with the cytotoxic agent via disulfide bonds are known in the art and include, for example, N-succinimidyl 3-(2-pyridyldithio)propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and N-succinimidyl-4-(2-pyridyldithio)$_2$-sulfo butanoate (sulfo-SPDB) (see, e.g., U.S. Application Publication No. 2009/0274713). Other bifunctional crosslinking reagents that can be used to introduce disulfide groups are known in the art and are described in U.S. Pat. Nos. 6,913,748, 6,716,821 and US Patent Publications 2009/0274713 and 2010/0129314, all of which are incorporated herein in its entirety by reference.

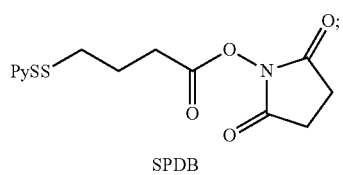

SPDB

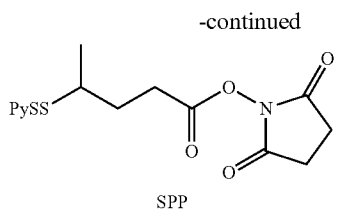

SPP

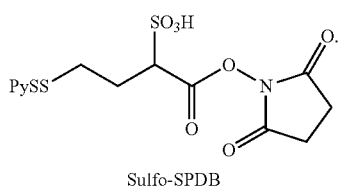

Sulfo-SPDB

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula (IX):

$$\text{HOOC—X}_l\text{—Y}_n\text{—Z}_m\text{—COOH} \qquad (IX),$$

wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent Application Publication No. 2005/0169933 A1.

In one embodiment BFCG'-Z' in formula VII is represented by the following structural formula:

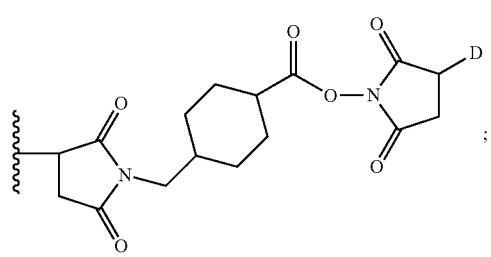
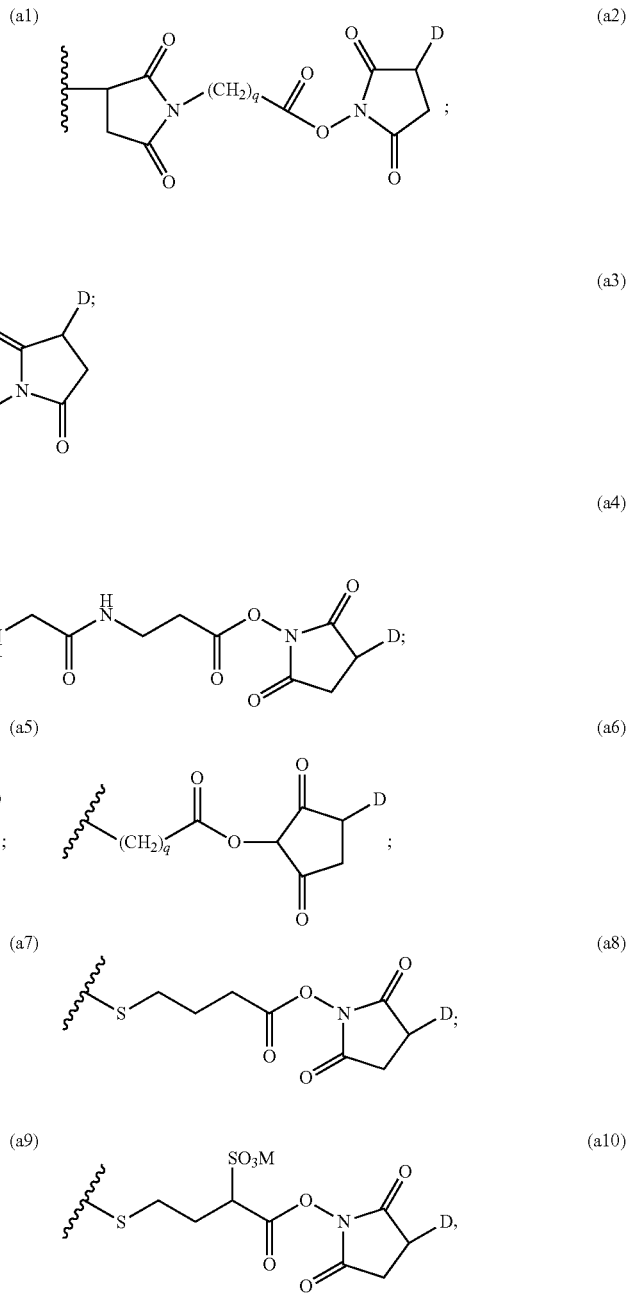

wherein: q is an integer from 1 to 5; n is an integer from 2 to 6; D is H or $SO_3M$; M is H or a cation, such as $Na^+$ or $K^+$. More preferably, BFCG'-Z' is represented by formula (a1), (a4), (a8), (a9) and (a10).

A "linking group" is a functional group on a compound that can react with a bifunctional crosslinking reagent, a compound comprising a derivatized maytansinol or maytansinol analog (for example, compounds of formula VI-IX) or a cell binding agent to form a chemical bond.

Two moieties, e.g., biologically active moieties such as a cell binding agent or a compound comprising a derivatized maytansinol or maytansinol analog (for example, compounds of formula VI-IX), or reactive moieties such as a linking group, are "linked" when connected by a chemical bond or other group such that biological activity and/or reactivity is substantially maintained. For example, MayO-A- and the cell binding agent are linked by Y-M'-BFCG in Structural Formula (III). A group that connects two such moieties is referred to herein as a "linker", which is Y-M'-BFCG in Stuctural Formula V.

A "residue" is the atoms remaining in a compound after a reactive functional group in the compound undergoes reaction with and binds to a second compound. Similarly, the atoms in the second compound remaining after the reaction are the residue of the second compound.

The term "self-immolative moiety" refers to a bifunctional chemical moiety that is capable of covalently linking two chemical moieties into a normally stable tripartate molecule. The self-immolative moiety is capable of spontaneously separating from the second moiety if the bond to the first moiety is cleaved. Sef-immolative moiety includes, but is not limited to those moieties described in U.S. Pat. Nos. 7,750,116 and 7,705,045 and US 2010/0062008. In one embodiment, the self-immolative moiety is p-aminobenzyloxycarbonyl (PABC). Alternatively, the self-immolative moiety is p-amiono-bis(hydroxymethyl)styrene (BHMS), having the structure p-NH-Ph-CH=C(CH$_2$O—)$_2$, including the carbonyl groups the structure is p-NH-Ph-CH=C(CH$_2$OCO—)$_2$.

The terms "interrupted" and "bearing" are used interchangeably herein. These terms mean that one or more methylene groups in the alkyl, alkenyl, alkynyl, arylalkyl and heterocyclylalkyl groups are replaced by the groups specified, such as a polyethylene unit, an aziridine group, an epoxy group, an amino group, an amido group, an ester group, an aryl group and an heterocyclyl group.

Linear or branched alkyls are saturated linear or branched-chain monovalent hydrocarbon radicals, preferably having from 1 to 10 carbon atoms. Examples of suitable linear alkyls include methyl, ethyl, propyl, butyl, pentyl, and hexyl. Examples of suitable branched alkyls include isopropyl, isobutyl, sec.-butyl, tert.-butyl, isopentyl, and 1-ethyl-propyl. Linear and branched alkyl groups may be substituted with one or more substituents, as described below.

Linear or branched alkenyls are linear or branched-chain monovalent hydrocarbon radicals preferably having from 2 to 10 carbon atoms with at least one site of unsaturation, i.e., a carbon-carbon, double bond, wherein the alkenyl radical includes radicals having "cis" and "trans" orientations, or alternatively, "E" and "Z" orientations. Examples of suitable linear alkenyls include ethylenyl or vinyl (—CH=CH$_2$), allyl (—CH$_2$CH=CH$_2$), propenyl, butenyl, pentenyl, hexenyl, pentadienyl and hexadienyl. Examples of suitable branched alkenyls include isobutenyl, isopentenyl and isohexenyl. Preferred alkenyl groups are vinyl, allyl and isobutenyl groups. Linear and branched alkenyl groups may be substituted with one or more substituents as described below.

Linear or branched alkynyls are linear or branched monovalent hydrocarbon radicals preferably having from 2 to 10 carbon atoms with at least one site of unsaturation, i.e., a carbon-carbon, triple bond. Examples of suitable alkynyls include ethynyl, propynyl, 1-butynyl, 2-butynyl, 1-pentynyl, 2-pentynyl, 3-pentynyl, hexynyl, and the like. Linear and branched alkynyl groups may be substituted with one or more substituents as described below.

Cyclic alkyls, cyclic alkenyls and cyclic alkynyls are monovalent non-aromatic, saturated or partially unsaturated rings, preferably having from 3 to 12 carbon atoms as monocyclic rings or from 7 to 12 carbon atoms as bicyclic rings. Examples of cyclic alkyls, alkenyls and alkynyls include cyclopropyl, cyclobutyl, cyclopentyl, cyclohexyl, cyclobutenyl, cyclopentenyl, cyclohexenyl, cyclohexadienyl, cyclobutynyl, cyclopentynyl and cyclohexynyl. Preferred cyclic alkyls, alkenyls and alkynyl groups include cyclopropyl, cyclopentyl, cyclohexyl, cyclopentenyl, cyclohexenyl, cyclohexadienyl and cyclohexynyl and cyclooctynyl. Cyclic alkyl, alkenyl and alkynyl groups may be substituted with one or more substituents as described below.

Preferred substituents for the alkyls, alkenyls and alkynyls represented by R and R' include one or more selected from a sulfonic acid group, a phosphonic acid, a carboxyl group, a carboxyl ester, such as a methyl or ethyl ester, and a primary, secondary, tertiary or quaternary amine. Preferred are methyl, ethyl, propyl and isopropyl groups. Preferred substituents for the alkyls, alkenyls and alkynyls represented by Y and Y' include one or more selected from halogen, alkoxy or aryloxy group, such as a methoxy, ethoxy or phenoxy group, a sulfide, such as S-methyl, S-ethyl and S-phenyl, a thioester, such as S-acetyl, a sulfoxide such as methyl or phenyl sulfoxide, a sulfone, such as methyl or phenyl sulfone, a sulfonamide, an aldehyde, an ketone, such as acetyl or benzoyl, an epoxide, such as ethylene oxide, an episulfide, an amide moiety, such as acetamido or benzamido, a primary, secondary, tertiary or quaternary amino or alkylamino or arylamino group, such as methylamino, dimethyl amino, diethylamino or triethylamino, a hydrazino, a sulfonic acid, a carboxyl group, a carboxy ester such as methyl or ethyl ester, a carboxamide, a ureido group, a phosphate group, a nitro group, an azido group, a cyano group, and a cyanate.

Aryl or aromatic groups are monovalent aromatic hydrocarbon radicals, preferably having from 6-18 carbon atoms. Aryls or aromatic groups include bicyclic radicals comprising an aromatic ring fused to a saturated, partially unsaturated ring, or aromatic carbocyclic or heterocyclic ring. Examples of unsubstituted aryls include phenyl, naphthyl and anthracenyl.

The aryls or aromatic groups may be substituted. The aryl or aromatic groups represented by R and R' are preferably substituted with at least one alkyl or alkenyl group containing from 1 to 4 carbon atoms, an alkoxy group such as methoxy or ethoxy, a halogen, a nitro group, a sulfonic acid group, a phosphonic acid, a carboxyl, a carboxy ester, such as methyl or ethyl ester, a primary, secondary, tertiary or quaternary amine or an alkoxy, such as methoxy or ethoxy. The aryl or aromatic groups represented by Y or Y' are preferably substituted with at least one halogen, alkoxy or aryloxy group, such as a methoxy, ethoxy or phenoxy group, a sulfide, such as S-methyl, S-ethyl and S-phenyl, a thioester, such as S-acetyl, a sulfoxide such as methyl or phenyl sulfoxide, a sulfone, such as methyl or phenyl sulfone, a sulfonamide, an aldehyde, an ketone such as acetyl or benzoyl, an epoxide, such as ethylene oxide, an episulfide, an amide moiety, such as acetamido or benzamido, a primary, secondary, tertiary or quaternary amino or alkylamino or arylamino group, such as methylamino, dimethyl amino, diethylamino or triethylamino, a hydrazino, a sulfonic acid, a carboxyl group, a carboxy ester such as methyl or ethyl ester, a carboxamide, a ureido group, a phosphate group, a nitro group, an azido group, a cyano group, or a cyanate. Preferred examples of substituted aryls or aromatic groups include nitrophenyl, dinitrophenyl, chlorophenyl, and methoxyphenyl, toluoyl, and aniline.

Heterocyclic group or heterocyclyl refers to a saturated, a partially unsaturated or aromatic carbocyclic radical, preferably having from 3 to 18 ring atoms in which at least one ring atom is a heteroatom selected from nitrogen, oxygen, phosphorus, and sulfur, where one or more ring atoms is optionally substituted independently with one or more substituents described below. A heterocyclic group may be a monocyclic group, preferably having from 3 to 7 ring members (2 to 6 carbon atoms and 1 to 4 heteroatoms selected from N, O, P, and S) or a bicyclic group, preferably having from 7 to 10 ring members (4 to 9 carbon atoms and 1 to 6 heteroatoms selected from N, O, P, and S). Heterocyclic groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Heterocyclic groups most preferably are cyclic compounds having 3 to 10-membered ring systems, containing one or two heteroatoms selected from N, O or S. Examples of heterocyclic groups include pyrrolidinyl, tetrahydrofuranyl, dihydrofuranyl, tetrahydrothienyl, tetrahydropyranyl, dihydropyranyl, piperidino, morpholino, piperazinyl, oxetanyl, thietanyl, pyrrolinyl, indolinyl, 2H-pyranyl, 4H-pyranyl, dioxanyl, pyrazolinyl, dithianyl, piperidinopiperidinyl, heterocylic aromatic groups such as, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl and benzofuranyl. In one embodiment, the heterocyclyl group is an optionally substituted piperazinyl group or an optionally substituted piperidinopiperidinyl (e.g., 4-piperidinopiperidinyl) group.

The heterocyclic groups may be optionally substituted with one or more substituents selected from alkyl or alkenyl containing from 1 to 4 carbon atoms, or alkoxy, such as methoxy or ethoxy, or with a halogen, a sulfide, such as S-methyl, S-ethyl and S-phenyl, a thioester, such as S-acetyl, a sulfoxide such as methyl or phenyl sulfoxide, a sulfone, such as methyl or phenyl sulfone, a sulfonamide, an aldehyde, an ketone such as acetyl or benzoyl, an epoxide, such as ethylene oxide, an episulfide, an amide moiety, such as acetamido or benzamido, a primary, secondary, tertiary or quaternary amino or alkylamino or arylamino group, such as methylamino, dimethyl amino, diethylamino or triethylamino, a hydrazino, a sulfonic acid, a carboxyl group, a carboxy ester such as methyl or ethyl ester, a carboxamide, a ureido group, a phosphate group, a nitro group, an azido group, a cyano group, and a cyanate.

Peptides useful in the invention a short amino acid units, preferably a 2 to 10 amino acid unit, comprised of natural or unnatural amino acids, including N-alkyl amino acids, example N-methyl amino acids, and also L-isomers, D-isomers or racemic amino acids thereof. Examples of suitable peptides include dipeptides, tripeptides, tetra peptides and pentapeptides. Preferred peptides include valine-citrulline, ala-phe, gly-gly-gly, ala-leu-ala-leu, ala-leu-ala-leu-β-ala.

Suitable halogens include F, Cl, Br or I

Pharmaceutically acceptable salts are pharmaceutically acceptable organic or inorganic salts of a compound of the invention. Exemplary salts include, but are not limited to, sulfate, lactate, salicylate, acid citrate, tartrate, ascorbate, succinate, maleate, gentisinate, fumarate, gluconate, glucuronate, formate, benzoate, glutamate, methanesulfonate "mesylate", ethanesulfonate, benzenesulfonate, p-toluenesulfonate, salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

Solvates are compounds that further include a stoichiometric or non-stoichiometric amount of solvent such as water, isopropanol, acetone, ethanol, methanol, hexane, heptane, dimethylacetamide, ethyl acetate, acetic acid, ethanolamine, dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound.

Synthesis of Ansamitocin Derivatives

The present invention provides a method of producing ansamitocin derivatives wherein the C3 hydroxyl, the C-14 hydroxymethyl, C-15 hydroxy, or C-20 desmethyl, is converted into an ester, carbamate, carbonate or ether bearing a functional group capable of reaction with a cell binding agent to provide a conjugate. Suitable functional groups are disulfides, thiols, alcohols, carboxyl, carbonyls, amines, hydrazides, maleimides, azides, halogens, sulfonates, such as methanesulfonate, trifluoromethane sulfonate and para-toluene sulfonate, vinylpyridines, vinyl sulfones, vinyl sulfonamides, sulfonic acids, sulfonyl chlorides, reactive carboxy esters, such as N-hydroxy succinimidyl, nitro or dinitrophenyl, pentafluorophenyl, sulfotetrafluorophenyl, phthalimidyl. These functional groups form a link to the cell binding agent via a disulfide bond, thioether bond, peptide bond, amide bond, ester bond or a hydrazone bond.

Figure 4B:
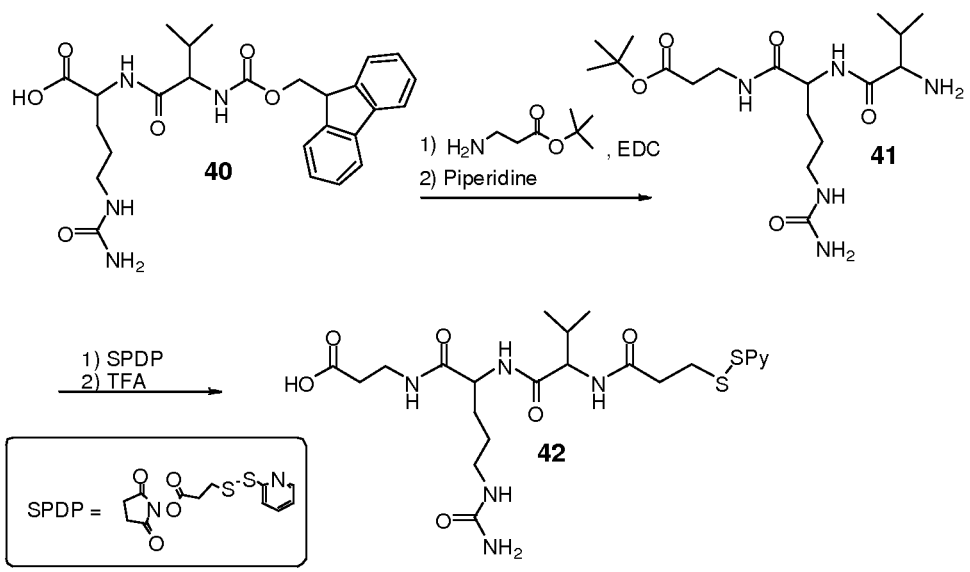
Figure 4C:
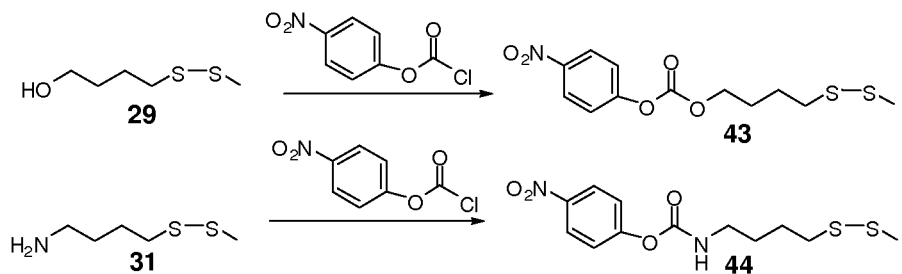

Ansamitocin ester derivatives are prepared by esterification of maytansinol with carboxylic acid compounds that also bear a suitable functional group for linking to cell binding agents. The synthesis of such side chains is shown in FIG. 4. The esterification reaction utilizes a coupling agent known in the art, such as dicyclohexylcarbodiimide (DCC) or 1[(3-dimethylamino)propyl]-3-ethylcarbodiimide (EDC), in the presence of a catalyst such as 1-hydroxybenzotriazole (HOBt), 4,4-dimethylamino pyridine (DMAP) or $ZnCl_2$. The synthesis of ansamitocin esters bearing different linking groups are shown in FIGS. 5-13.

Thiol-containing nsamitocin derivatives 6 (FIG. 5), 55 (FIG. 13a) and 58 (FIG. 13b) bearing esters of various chain length were synthesized as follows. Mercapto-carboxylic acids with varying carbon chain lengths and branching were prepared and converted to the corresponding methyldisulfides. Esterification of maytansinol with these carboxylic acids proceeded smoothly in the presence of DCC/DMAP to provide the methyldithio ansamitocins. Reduction of the disulfide with dithiothreitol (DTT) provided the thiol-containg ansamitocin 6, 55 and 58.

Ansamitocin derivatives 13a,b bearing an N-hydroxysuccinidyl ester or N-hydroxysuccinimidyl ester for linkage to cell binding agents were prepared as shown in FIG. 11. Hexane-1,6-dioic acid was partially protected on one of the two carboxyl groups with TEOC. Esterification of maytansinol provided the ansamitocin ester derivative bearing a protecetd carboxyl group. Deprotection of the TEOC group with tetrabutylammonium fluoride provided carboxyansamitocin derivative 14b. Condensation with N-hydroxysuccinimde or N-hydroxysulfosuccinimde provided the ansamitocin derivatives 13a,b bearing reactive esters for linkage to cell binding agents.

Ansamitocin carbamate derivatives are prepared by reaction of maytansinol with a chloroformate, such as, 4-nitrophenyl chloroformate followed by reaction with an amino compound which also bears a functional group for reaction with a cell binding agent, such as a disulfide moiety. An alternative method is shown in FIG. 12b Ansamitocin carbonate derivatives are prepared by reaction of maytansinol with phosgene followed by reaction with a hydroxy compound which also bears a functional group for reaction with a cell binding agent, such as a disulfide moiety. An alternative method is shown in FIG. 12b.

Ansamitocin ether derivatives are prepared as shown in FIG. 12a. Maytansinol is treated with a base (for suitable bases see U.S. Pat. Nos. 7,598,375 and 7,301,019, expressly incorporated herein by reference), such as sodium hydride, n-butyl lithium, zinc triflate/diisopropylethyl amine or lithium hexamethyldisilazide followed by reaction with a halogen or sulfonate (such as methanesulfonate, trifluoromethane sulfonate or para-toluene sulfonate) containing compound which also bears a functional group for reaction with a cell binding agent.

Additional general methods of preparing esters, carbamates, carbonates and ethers are known in the art (see for example *March's Advanced Organic Chemistry*, Jerry March & Michael B. Smith, Wiley 2007, expressly incorporated herein by reference).

In Vitro Cytotoxicity of Ansamitocin Derivatives

The in vitro cytotoxicity of ansamitocin derivatives of the present invention can be measured by methods previously disclosed (U.S. Pat. No. 7,276,497 and Widdison et al., J. Med. Chem., 49; 4392, 2006, both expressly incorporated herein by reference). For example, cell lines such as the human breast carcinoma line SK-Br-3, or the human epidermoid carcinoma cell line KB, can be used for the assessment of cytotoxicity of these new ansamitocin derivatives. Cells to be evaluated are exposed to the compounds for 72 hours and the surviving fractions of cells measured in direct assays by known methods. $IC_{50}$ values are calculated from the results of the assays.

Cell-Binding Agents

The effectiveness of the ansamitocin derivatives thereof or conjugates thereof of the invention as therapeutic agents depends on the careful selection of an appropriate cell-binding agent. Cell-binding agents may be of any kind presently known, or that become known and include peptides and non-peptides. Generally, these can be antibodies (especially monoclonal antibodies), lymphokines, hormones, growth factors, vitamins, nutrient-transport molecules (such as transferrin), or any other cell-binding molecule or substance.

More specific examples of cell-binding agents that can be used include:
 polyclonal antibodies;
 monoclonal antibodies;
 fragments of antibodies such as Fab, Fab', and F(ab')$_2$, Fv (Parham, *J. Immunol.* 131:2895-2902 (1983); Spring et al. *J. Immunol.* 113:470-478 (1974); Nisonoff et al. *Arch. Biochem. Biophys.* 89:230-244 (1960)); minibodies, diabodies, tribodies, tetrabodies, nanobodies, probodies, domain bodies, unibodies, minibodies and the like (see Kim et al., Mol, Cancer Ther., 7: 2486-2497 (2008), Carter, Nature Revs., 6: 343-357 (2006), R. Kontermann & S. Dubel, 2001 Antibody Engineering, Springer-Verlag, Heidelberg-New York;
 bispecific antibodies (Morrison, S L *Nature biotechnology* 25 (11): 1233-4 (2007));
 ankyrin repeat proteins (DARPins; Zahnd et al., *J. Biol. Chem.*, 281, 46, 35167-35175, (2006); Binz, H. K., Amstutz, P. & Pluckthun, A. (2005) *Nature Biotechnology*, 23, 1257-1268) or ankyrin-like repeats proteins or synthetic peptides described, for example, in U.S. Patent Publication Number 20070238667; U.S. Pat. No. 7,101,675; and WO/2007/147213; WO/2007/062466)
 interferons (e.g. alpha., .beta., .gamma.);
 lymphokines such as IL-2, IL-3, IL-4, IL-6;
 hormones such as insulin, TRH (thyrotropin releasing hormone), MSH (melanocyte-stimulating hormone), steroid hormones, such as androgens and estrogens;
 growth factors and colony-stimulating factors such as EGF, TGF-alpha, FGF, VEGF, G-CSF, M-CSF and GM-CSF (Burgess, *Immunology Today* 5:155-158 (1984));
 transferrin (O'Keefe et al. *J. Biol. Chem.* 260:932-937 (1985)); and vitamins, such as folate.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969, 108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine $IgG_1$ antibody that binds specifically to the CD33 antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine $IgG_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia. Hu-B4 is a resurfaced antibody derived from the murine anti-B4 antibody (Roguska et al., 1994, Proc. Natl. Acad. Sci., 91, pg 969-973). HuN901 is a humanized antibody that binds to the CD56 antigen expressed on small cell lung cancer, multiple myeloma, ovarian cancer and other solid tumors including neuroendocrine cancers (Roguska et al., 1994, Proc. Natl. Acad. Sci., 91, pg 969-973). B38.1 is a chimeric antibody targeting EpCAM. Fully human antibodies such as panitumumab targeting the EGF receptor expressed on several solid tumors may also be used (Van Cutsem et al., J Clin Oncol. 2007; 25(13):1658-1664). Anti-erbB antibodies such as trastuzumab and pertuzumab may also be used (Nahta et al., 2004, *Cancer Research* 64:2343-2346.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, EGFR, tarnsferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80, CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, c-kit, 1GF1R, PSGR, NGEP, PSMA, PSCA, LGR5, B7H4, TAG72 (tumor-associated glycoprotein 72), 5T4 (Bogharert et al., International J. of Oncology 32: 221-234, 2008) and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In another embodiment, the cell-binding agent is huN901, huMy9-6, huB4, huC242, trastuzumab, bivatuzumab, sibrotuzumab, rituximab, CNTO95, huDS6, anti-mesothelin antibodies described in WO 2010/124797 (such as MF-T), anti-cripto antibodies described in US Patent Application Publication 2010/0093980 (such as huB3F6), anti-CD138 antibodies described in US Patent Application Publication 2007/0183971 (such as huB-B4), anti-EGFRvIII antibodies described U.S. Pat. Nos. 7,736,644 and 7,628,986 and US Application Publication Nos. 2010/0111979, 2009/0240038, 2009/0175887, 2009/0156790 and 2009/0155282, humanized EphA2 antibodies described in PCT/IB2010/054417 and PCT/IB2010/054422 (such as 2H11R35R74); anti-CD38 antibodies described in WO2008/047242 (such as hu38SB19), anti-folate receptor antibodies described in U.S. Provisional Application Nos. 61/307,797, 61/346,595 and 61/413,172 and U.S. application Ser. No. 13/033,723. The teachings of all these applications are incorporated herein by reference in its entirety.

Production of Cell Binding Agent Conjugates

The present invention also provides ansamitocin derivative-cell-binding agent conjugates comprising a cell binding agent linked to one or more cytotoxic ansamitocin derivatives via a variety of linkers, including, but not limited to, disulfide linkers, thioether linkers, amide bonded linkers, peptidase-labile linkers, acid-labile linkers, esterase-labile linkers.

The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

Representative cytotoxic conjugates of the invention are antibody/ansamitocin derivative, antibody fragment-ansamitocin derivative, epidermal growth factor (EGF)/ansamitocin derivative, melanocyte stimulating hormone (MSH)/ansamitocin derivative, thyroid stimulating hormone (TSH)/ansamitocin derivative, somatostatin/ansamitocin derivative, folate/ansamitocin derivative, estrogen/ansamitocin derivative, estrogen analogue/ansamitocin derivative, prostate specific membrane antigen (PSMA) inhibitor/ansamitocin derivative, matriptase inhibitor/ansamitocin derivative, designed ankyrin repeat proteins (DARPins)/ansamitocin derivative, androgen/ansamitocin derivative, and androgen analogue/ansamitocin derivative.

The conjugates of the present invention can be prepared according to any known method in the art. See, for example, WO 2009/134977, U.S. Pat. Nos. 7,811,572, 6,441,163, U.S 2006/0182750, and Widdison, W. C. et. al. Semisynthetic maytansine analogues for the targeted treatment of cancer. *J Med Chem* 2006, 49 (14), 4392-4408, In one embodiment, the conjugates of the present invention can be prepared by: a) reacting a cell-binding agent with a bifunctional crosslinking reagent to form a modified cell-binding agent having the linkers covalently bound thereto; b) optionally purifying the modified cell-binding agent; c) conjugating a cytotoxic agent (i.e., ansamitocin derivative described herein, such as compounds of formula VI-IX) to the modified cell-binding agent to form a cell-binding agent-cytotoxic agent conjugate; and d) purifying the cell-binding agent-cytotoxic agent conjugate.

In another embodiment, the conjugates of the present invention can be prepared by reacting a cell-binding agent with a drug-linker compound (e.g., compounds of formula X-XII) having a linking group capable of forming a covalent bond with the cell-binding agent to form a cell-binding agent-cytotoxic agent conjugate. The conjugate can then be purified. The drug-linker compound can be generated in situ and used to react with the antibody without purification.

An ansamitocin derivative bearing a thiol moiety can be coupled to a cell binding agent, such as an Fab unit of an antibody after first reacting the cell binding agent with a bifunctional linker such as commercially available SMCC. For example several lysine residues of an Fab fragment can be reacted with SMCC to give a modified Fab that bears maleimide groups then the thiol containing ansamitocins can be reacted with the modified Fab to give conjugate.

An ansamitocin derivative bearing a maleimide group can be reacted with a cell binding agent that contains one or more thiol moieties. For example an antibody can be reacted with dithiothreitol to reduce several of the antibodies internal disulfide bonds. The dithiothreitol can be removed by size exclusion chromatography then the maleimide-bearing ansamitocin derivative can be coupled to the free thiol groups to give conjugate.

An ansamitocin derivative bearing an activated ester such as an N-hydroxysuccinimide ester can be reacted with a cell binding agent the bears one or more amine moieties. For example a diabody which contains one or more lysine residues can be reacted with an ansamitocin derivative bearing a pentafluorophenyl ester to give conjugate.

The cell-binding agent conjugate prepared by methods described above can be purified by any methods described herein.

Disulfide-containing cytotoxic conjugates are made by reacting a thiol-containing ansamitocin derivative with an appropriately modified cell-binding agent (see FIGS. 14, 25). These conjugates are purified to remove non-linked cytotoxic agent by using gel-filtration, ion exchange chromatography, ceramic hydroxyapatite (CHT) chromatography, hydrophobic interaction chromatography (CHT), tangential flow filtration (TFF), or by HPLC.

A solution of an antibody in aqueous buffer is incubated with a molar excess of an antibody modifying agent such as N-succinimidyl-3-(2-pyridyldithio)propionate (SPDP) or with N-succinimidyl-4-(2-pyridyldithio)butanoate (SPDB) to introduce dithiopyridyl groups. The modified antibody is then reacted with the thiol-containing cytotoxic agent such as compound 17, 18, 19 or 46, to produce a disulfide-linked antibody-ansamitocin derivative conjugate. The cytotoxic-cell binding conjugate is then purified using any of the above mentioned methods. Other cross-linking agents that are used to introduce disulfide groups are known in the art and are disclosed in U.S. Pat. Nos. 6,913,748, 6,716,821 and US Patent Publications 20090274713 and 20100129314.

Alternatively, the antibody is incubated with a molar excess of an antibody modifying agent such as 2-iminothiolane, L-homocysteine thiolactone (or derivatives), or N-Succinimidyl-5-acetylthioacetate (SATA) to introduce sulfhydryl groups. The modified antibody is then reacted with the appropriate disulfide-containing ansamitocin derivative to produce a disulfide-linked antibody-cytotoxic agent conjugate. The antibody-cytotoxic agent conjugate is then purified by gel-filtration or other methods mentioned above.

The number of cytotoxic molecules bound per antibody molecule is determined spectrophotometrically by measuring the ratio of the absorbance at 280 nm and 252 nm. An average of 1-10 cytotoxic molecules per antibody molecule(s) are linked by this method. The preferred average number of linked cytotoxic molecules per antibody molecule is 2-5, and the most preferred is 3-4.5.

Alternatively, conjugates can be prepared wherein the ansamitocin derivative is linked to the cell binding agent via a non-cleavable linker (see FIGS. 15, 16, 26). A solution of an antibody in aqueous buffer is incubated with a molar excess of an antibody-modifying agent such as N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. The modified antibody is then reacted with the thiol-containing ansamitocin derivative to produce a thioether-linked antibody-cytotoxic conjugate. The antibody-cytotoxic conjugate is then purified by gel-filtration or other methods mentioned above or by methods known to one of skill in the art. Other cross-linkers that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, BMPEO, BMPS, GMBS, EMCS. 5-maleimidovaleric acid NHS, HBVS, LC-SMCC, MBS, MPBH, SBAP, SIA, KMUA, SMPB, SMPH, SVSB, DTME, BMB, BMDB, BMH, BMOE, BM(PEO)$_3$, BM(PEO)$_3$, sulfo-SMCC, sulfo-SLAB, sulfo-MBS, sulfo-GMBS, sulfo-EMCS, sulfo-KMUS, and sulfo-SMPB.

Figure 24A:
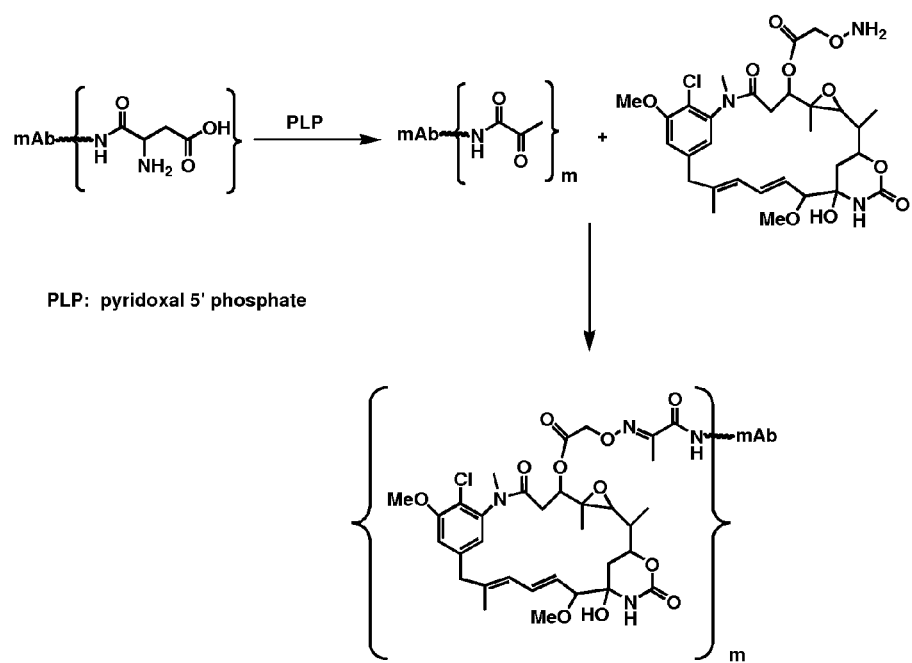
FIG. 24 shows a conjugation procedure for an amide-linked conjugate prepared with compounds of the present invention.
Figure 24B:
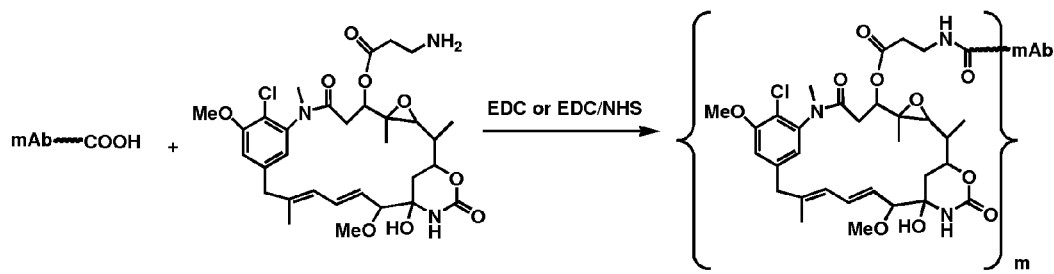

Ansamitocin derivatives bearing an amine-reactive group, such as an N-hydroxy succinimidyl (NHS) ester, are reacted with the cell binding agent to produce direct amide linked conjugates (see FIGS. 20, 24, 27). The antibody-cytotoxic agent conjugate is purified by gel-filtration or other methods mentioned above.

Cell-binding agent-ansamitocin derivative conjugates comprising peptide cleavable linkers are prepared from the corresponding peptide-containing ansamitocin derivatives (see FIGS. 17, 18, 19).

The peptide-containing ansamitocin derivative bearing a terminal N-hydroxysuccinimide ester is reacted directly with the cell binding agent to provide a peptide-cleavable conjugate. The conjugate is purified by gel filtration, dialysis or other methods known in the art. Exemplary peptides include dipeptides, such as valine-citrulline (val-cit), alanine-phenylalanine; tripeptides, such as, gly-gly-gly, gly-val-cit, ala-val-cit; tetrapeptides, such as, leu-leu-leu-leu, ala-lys-ala-lys, ala-leu-ala-leu; pentapeptides or hexapeptides. Other peptides that may be used are disclosed in the art (see US Patent Publication 2008/0050310, 20090047296, 20080280937, 20090203889).

Cell binding agent conjugates of ansamitocin derivatives comprising acid-labile links are prepared as shown in FIGS. 21, 22). Conjugtaes with acid-labile links such as hydrazones are prepared through condensation of an ansamitocin derivative containing an alkyl, aryl ketone with a hydrazide modified cell binding agent. Alternatively, the cell binding agent is modified to introduce a carbonyl moiety as described in the art (see U.S. Pat. Nos. 5,773,001; 5,767,285; 5,877,296), and then reacted with an ansamitocin derivative bearing a hydrazido moiety.

Conjugates of cell-binding agents with ansamitocin derivatives of the invention are evaluated for their ability to suppress proliferation of various unwanted cell lines in vitro. For example, cell lines such as the human colon carcinoma line COLO 205, the human melanoma cell line A-375 and the human myeloid leukemia cell line HL60 can be used for the assessment of cytotoxicity of these conjugates. Cells to be evaluated can be exposed to the compounds for 24 hours, 72 hours or longer and the surviving fractions of cells measured in direct assays by known methods. $IC_{50}$ values can then be calculated from the results of the assays.

The in vivo anti-tumor efficacy of conjugates of cell binding agents with ansamitocin derivatives are evaluated by the methods previously disclosed (U.S. Pat. No. 7,473,796, incorporated herein by reference).

Compositions and Methods of Use

The present invention provides pharmaceutical compositions comprising an effective amount of any of the ansamitocin derivative-cell-binding agent conjugates of the present invention, pharmaceutically acceptable as a salt or solvate thereof, and a pharmaceutically acceptable carrier, diluent or excipient.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the ansamitocin derivative-cell-binding agent conjugates of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

The entire contents of all publications, patents and non-patent references mentioned herein are expressly incorporated herein by reference.

EXAMPLES

The invention will now be illustrated by reference to non-limiting examples. Unless otherwise stated, all percents, ratios, parts, etc. are by weight.

All reagents were purchased from the Aldrich Chemical Co., New Jersey, or other commercial sources. Maytansinol (11) was prepared as described previously (U.S. Pat. No. 6,333,410). Nuclear Magnetic Resonance ($^1$H NMR) spectra were acquired on a Bruker 400 MHz instrument and mass spectra were acquired on a Bruker Daltonics Esquire 3000 instrument using electrospray ionization. In vitro cytotoxicity assays are performed as previously described (see U.S. Pat. No. 7,276,497 and W. C. Widdison et al., *J. Med. Chem.*, 2006, 49, 4392-4408).

The KB (ATCC CCl-17) cell line is of human epithelial origin. The SK-BR-3 (ATCC HTB-30) cell line was established from a human breast adenocarcinoma. The human colon tumor cell lines COLO 205 (ATCC CCL-222) and HT-29 (ATCC HTB 38), the human melanoma cell line A-375 (ATCC CRL 1619), the human Burkitts lymphoma cell line Ramos (ATCC CRL-1596) and the human myeloid leukemia cell line HL-60 (ATCC CCL-240) were all obtained from ATCC, Maryland. Cell lines were grown in Dulbecco's modified Eagles Medium (DMEM, Biowhittaker, Walkersville, Md.) with L-glutamine supplemented with 10% fetal bovine serum (Hyclone, Logan, Utah) and 50 μg/mL gentamycin sulfate (Life Technologies, Rockville, Md.). Cells were maintained at 36-37.5° C. in a humidified atmosphere that contained 6% $CO_2$.

Example 1

In Vitro Cytotoxicity

The cytotoxicity study was performed using a clonogenic assay. The test cell lines (KB and SK-Br-3) were plated into 6-well culture dishes at a constant number of 1000 cells per well. Cells were incubated with varying concentrations (0 to 3 nM) of the various ansamitocins or maytansine for 72 hours. The medium was then aspirated from the plates and replaced with fresh medium. Cultures were allowed to grow, and form colonies, for a total of 7-10 days after plating. The cultures were then fixed and stained with 0.2% crystal violet in 10% formalin/PBS and colonies were counted. Plating efficiency of non-treated cells (medium alone) was determined by dividing the number of colonies counted by the number of cells plated. Surviving fraction of cells exposed to the drugs was determined by dividing the number of colonies in wells that were exposed to the drug by the number of colonies in the control wells.

The results of the in vitro cytotoxicity measurements of various ansamitocins in comparison to maytansine are shown in FIG. 3. The results show that all three ansamitocin esters tested were more potent than maytansine towards both cell lines (KB and SK-Br-3) that were tested. For example, ansmitocin P4', which bears a C3 pentanoyl, and ansamitocin P3 baering an isobutanoyl ester are both 17-fold more potent ($IC_{50}=2\times10^{-12}$ M) than the C3 N-acetyl-N-methylalanyl ester, maytansine ($IC_{50}=3.4\times10^{-11}$ M) towards SK-Br-3 cells). Similarly, the ansamitocin P3, P4 and P4' esters are 3.7 to 6-fold more potent than maytansine towards KB cells.

Example 2

Preparation of Derivatized Carboxylic Acids

Compound 28.

3-mercapto propionic acid was reacted with S-methyl methanethiosulfonate in ethanol to give 28 as described previously (Widdison, W. C., et al., *J Med Chem*, 2006. 4, 4392-408).

Compound 30.

Compound 30 is made by reacting S-methyl methanethiosulfonate with 4-mercapto-1-butanol.

Compound 32.

Compound 32 is made by reacting S-methyl methanethiosulfonate with 1-amino-butan-4-thiol (Reineke, T. M. et. al. *Bioconjugate Chem.*, 2003 14, 247-254).

Compound 34.

The furan-bearing carboxylic acid 34 is prepared as follows. Methyl 5-hydroxymethyl-2-furoate (33) (Moore, J. A et. al., Journal of Polymer Science, Polymer Chemistry Edition (1984), 22(3), 863-4) is reacted with methanesulfonyl chloride followed by reaction with thiourea and hydrolysis to give 33. After which 33 is reacted with methanethiosulfonate.

Compound 37:

Compound 37 is prepared by reacting 2,2'-dithidipyridine with 4-(mercaptomethyl)benzoic acid 36.

Compound 39.

Compound 39 is prepared by reacting 2,2'-dithidipyridine with the thio PEG4 carboxylic acid 38.

Compound 42.

The peptide-bearing carboxylic acid 42 is prepared as follows. The dipeptide FMoc-Val-Cit-OH 40 (Dubowchik G. M. et. al. *Bioconjugate Chem.* 2002, 13, 855-869) is coupled to the t-butyl ester of beta alanine using N-(3-Dimethylaminopropyl)-N'-ethylcarbodiimide hydrochloride (EDC) and N-hydroxybenzotriazole (HOBT) followed by FMoc de-protection with piperidine to give 41. Compound 41 is then reacted with N-Succinimidyl 3-[2-pyridyldithio]-propionate (SPDP) followed by t-butyl ester deprotection with trifluoroacetic acid.

Example 3

Preparation of 4-Nitro-Phenol Carbonates or 4-Nitro-Phenol Carbamates 4-nitrophenylchloroformate is reacted with compound 30 to give the disulfide-bearing carbonate 43.

4-nitrophenylchloroformate is reacted with compound 32 to give the disulfide-bearing carbamate 44.

Preparation of Ansamitocin Derivatives

Example 4

The thiol bearing ansamitocin derivative 6 is prepared by 4,4-dimethylpyridine (DMAP) catalyzed dicyclohexylcarbodiimide (DCC) coupling of maytansinol to 28 followed by disulfide reduction using dithiothreitol.

Example 5

The thiol bearing ansamitocin derivative 19 is prepared by 4,4-dimethylpyridine (DMAP) catalyzed dicyclohexylcarbodiimide (DCC) coupling of maytansinol to 37 followed by disulfide reduction using dithiothreitol.

Example 6

The thiol bearing ansamitocin derivative 23 is prepared by 4,4-dimethylpyridine (DMAP) catalyzed dicyclohexylcarbodiimide (DCC) coupling of maytansinol to 34 followed by disulfide reduction using dithiothreitol.

Example 7

The thiol bearing ansamitocin derivative 18 is prepared by 4,4-dimethylpyridine (DMAP) catalyzed dicyclohexylcarbodiimide (DCC) coupling of maytansinol to 39 followed by disulfide reduction using dithiothreitol.

Example 8

The thiol bearing ansamitocin derivative 17 is prepared by 4,4-dimethylpyridine (DMAP) catalyzed dicyclohexylcarbodiimide (DCC) coupling of maytansinol to 42 followed by disulfide reduction using dithiothreitol.

Example 9

The thiol-bearing ansamitocin derivative 20 is prepared by DMAP catalyzed coupling of maytansinol to 44 followed by disulfide reduction using dithiothreitol.

Example 10

The thiol-bearing ansamitocin derivative 21 is prepared by DMAP catalyzed coupling of maytansinol to 43 followed by disulfide reduction using dithiothreitol.

Example 11

The ansamitocin derivative 9 is prepared by DMAP catalyzed DCC coupling of maytansinol to 3 oxopropionic acid 48 (Yamada, E. M. et. Al. *J. Biol. Chem.* 1959 234, 941-945).

Example 12

The ansamitocin derivative 8 is prepared by DMAP catalyzed DCC coupling of maytansinol to 3-oxobutanoic acid 49.

Example 13

The ansamitocin derivative 15 is prepared by DMAP catalyzed DCC coupling of maytansinol to 50 followed by FMoc deprotection with morpholine.

Example 14

The ansamitocin derivative 16 is prepared by DMAP catalyzed DCC coupling of maytansinol to 51 Fmoc-beta-Alanine followed FMoc deprotection with morpholine.

Example 15

The ansamitocin derivatives 13a,b were prepared as follows (see FIG. 11).

Hexandioic acid-1-[2-trimethylsilyl)ethyl]ester ester of maytansinol (14a)

To a solution of hexandioic acid-1[2-trimethylsilyl)ethyl] ester (523.0 mg, 2.12 mmol), $CH_2Cl_2$ (2 mL) was added dicyclohexylcarbodiimide (438 mg, 2.124 mmol), 4-dimethylaminopyridine (86.0 mg, 0.708 mmol) and maytansinol (200.00 mg, 0.354 mmol) at ambient temperature. After 2 h the reaction was filtered and concentrated in vacuo. The product was isolated by C18 HPLC eluting with a linear gradient of acetonitrile in aqueous 0.1% formic acid. Product containing fractions were combined and concentrated in vacuo to give 32.0 mg (11% yield) of desired product. MS calcd $(M+Na)^+$, 815.3. found, 815.2.

Hexanedioic Acid Ester of Maytansinol (14b)

To an ice/water cooled flask containing a solution of the hexandioic acid-1[2-trimethylsilyl)ethyl]ester ester of maytansinol (30 mg, 0.038 mmol) in THF (378 µL) was added a solution of 1 M tetrabutyl ammonium fluoride in tetrahydrofuran (45.4 µL, 0.045 mmol). The cooling bath was and after 6 h the reaction was quenched with saturated ammonium chloride, extracted with EtOAC washed with brine, dried over anhydrous $Na_2SO_4$ and concentrated in vacuo. The product was isolated by C18 HPLC eluting with a linear gradient of acetonitrile in aqueous 0.1% formic acid. Product containing fractions were combined and concentrated in vacuo to give 5.4 mg (21% yield) of desired product. $^1$H NMR (400 MHz, $CDCl_3$) δ 0.82 (s, 3H), 1.35-1.17 (m, 4H), 1.54-1.39 (m, 2H), 1.61 (d, J=13.7 Hz, 1H), 1.68 (s, 3H), 1.82-1.70 (m, 2H), 2.20 (d, J=11.9 Hz, 2H), 2.36 (d, J=11.1 Hz, 3H), 2.61-2.50 (m, 2H), 2.77-2.63 (m, 2H), 2.91 (d, J=9.7 Hz, 1H), 3.16 (s, 1H), 3.19 (s, 3H), 3.37 (s, 3H), 3.51 (dd, J=17.7, 11.0 Hz, 1H), 3.72 (dd, J=14.1, 7.0 Hz, 1H), 3.99 (s, 3H), 4.29-4.21 (m, 1H), 4.88 (d, J=9.1 Hz, 1H), 5.53 (dd, J=15.5, 8.8 Hz, 1H), 6.16 (d, J=10.6 Hz, 1H), 6.42 (dd, J=15.3, 10.9 Hz, 1H), 6.63 (s, 1H), 6.79 (s, 1H), 6.84 (s, 1H). MS calcd $(M+Na)^+$, 715.3; found, 715.3

N-Hydroxy Succinimide Ester of the Hexanedioic Acid Ester of Maytansinol (13)

To a solution of the hexanedioic acid ester of maytansinol (5 mg, 7.21 µmol) in $CH_2Cl_2$ (1 mL) was added N-hydroxysuccinimide (4.15 mg, 0.036 mmol) and N-(3-dimthylaminopropyl)-N'-ethylcarbodiimide hydrochloride (6.91 mg, 0.036 mmol) at ambient temperature. After 24 h solvent was removed under vacuum and the residue was purified by C18 HPLC eluting with a linear gradient of acetonitrile in aqueous 0.1% formic acid. Product containing fractions were immediately frozen and lyophilized to give 0.91 mg (16% yield) of desired product. MS calcd $(M+Na)^+$, 812.3; found, 812.3

Example 16

Thiol-Containing Ansamitocin 6 was Prepared as Follows (See FIG. 5)

3-(methyldithio)propanoic acid ester of maytansinol (45)

To a solution of 3-(methyldithio)propanoic acid (323.0 mg, 2.12 mmol) in $CH_2Cl_2$ (2 mL) was added dicyclohexylcarbodiimide (438 mg, 2.124 mmol), 4-dimethylaminopyridine (89.3 mg, 0.731 mmol) and maytansinol (197.0 mg, 0.348 mmol) at ambient temperature. After 2 h the reaction was filtered and concentrated in vacuo. Product was purified by C18 HPLC eluting with a linear gradient of acetonitrile in aqueous 0.1% formic acid. Product containing fractions were combined and concentrated in vacuo to give 93.6 mg (38% yield) of desired product. $^1$H NMR (400 MHz, $CDCl_3$) δ 0.85 (s, 3H), 1.24 (d, J=13.7 Hz, 1H), 1.28 (d, J=6.4 Hz, 3H), 1.53-1.41 (m, 1H), 1.63 (d, J=13.6 Hz, 2H), 1.68 (s, 3H), 2.19 (dd, J=13.9, 2.6 Hz, 1H), 2.43-2.40 (m, 1H), 2.44 (m, 2H), 2.52 (dd, J=13.9, 12.0 Hz, 1H), 2.87-2.77 (m, 2H), 2.89 (dd, J=8.5, 4.9 Hz, 1H), 3.02-2.94 (m, 3H), 3.18 (s, 3H), 3.36 (s, 3H), 3.52 (d, J=8.9 Hz, 1H), 3.56 (d, J=12.9 Hz, 1H), 3.99 (s, 3H), 4.24 (t, J=11.3 Hz, 1H), 4.96 (dd, J=11.9, 2.7 Hz, 1H), 5.61 (dd, J=15.4, 8.9 Hz, 1H), 6.27 (d, J=11.0 Hz, 1H), 6.34 (s, 1H), 6.45 (dd, J=15.4, 11.1 Hz, 1H), 6.80 (d, J=1.7 Hz, 1H), 6.84 (d, J=1.7 Hz, 1H). $^{13}$C NMR (101 MHz, $CDCl_3$) δ 12.08, 14.51, 15.76, 22.16, 22.72, 24.70, 31.25, 33.41, 34.24, 35.68, 38.34, 47.15, 56.58, 56.72, 60.34, 66.18, 74.47, 81.09, 88.08, 113.02, 119.44, 122.28, 124.49, 128.09, 132.47, 140.09, 141.58, 142.51, 149.10, 152.32, 168.52, 170.51. MS calcd $(M+Na)^+$, 721.2; found, 721.2.

3-thiopropanoic acid ester of maytansinol (6)

To a solution of the 3-(methyldithio)propanoic acid ester of maytansinol (45 mg, 0.064 mmol) in 1,2-Dimethoxyethane (3 mL) was added a solution of D,L-dithiothreitol (49.6 mg, 0.322 mmol) in 100 mM potassium phosphate, 2 mM EDTA, pH 7.5 buffer (3.00 mL) at ambient temperature. After 1 h the reaction volume was reduced in vacuo to approximately ½ its original volume and the product was isolated C18 HPLC eluting with a linear gradient of acetonitrile in aqueous 0.1% formic acid. The product containing fraction was immediately frozen and lyophilized to give 4.0 mg (9.5% yield) of desired product 6. MS calcd (M+Na)$^+$, 675.2; found, 675.2.

Example 16

Thiol-Containing Ansamitocin 55 was Prepared as Follows (See FIG. 13a)

6-(methyldithio)hexanoic acid (53)

To an ice/water bath cooled flask containing a solution of 6-mercaptohexanoic acid (500.0 mg, 3.37 mmol) de ionized water (2 mL) was added a solution of S-Methyl methanethiosulfonate (468 mg, 3.71 mmol) in ethanol (1 mL). After 16 hr the reaction was diluted with saturated sodium chloride (400 mL) and extracted with ethyl ether (3×150 mL). The combined extracts were washed with saturated NaCl (100 mL), dried over anhydrous $Na_2SO_4$ and concentrated in vacuo. The product was purified by silica chromatography eluting with ethyl acetate/hexanes/acetic acid (40:58:2). Product containing fractions were combined and concentrated in vacuo to give 482 mg (73% yield) of the desired product. MS calcd (M+Na)$^+$, 217.3; found, 217.3

6-(methyldithio)hexanoic acid ester of maytansinol (54)

To a solution of 6-(methyldithio)hexanoic acid (413.0 mg, 2.12 mmol) in $CH_2Cl_2$ (2 mL) was added dicyclohexylcarbodiimide (438 mg, 2.124 mmol) 4-dimethylaminopyridine (86.0 mg, 0.708 mmol) and maytansinol (200.00 mg, 0.354 mmol) at ambient temperature. After 2 h the reaction was filtered and concentrated in vacuo. The product was isolated by C18 HPLC eluting with a linear gradient of acetonitrile in aqueous 0.1% formic acid. Product containing fractions were combined and concentrated in vacuo to give 36.7 mg (14% yield) of desired product. MS calcd (M+Na)$^+$, 763.3; found, 763.3.

6-mercaptohexanoic acid ester of maytansinol (55)

To a solution of the 6-(methyldithio)hexanoic acid ester of maytansinol (30.0 mg, 0.040 mmol) in 1,2-Dimethoxyethane (3 mL) was added a solution of D, L-dithiothreitol (31.2 mg, 0.202 mmol) in 100 mM potassium phosphate, 2 mM EDTA, pH 7.5 buffer (3.00 mL) at ambient temperature. After 4 h the reaction volume was concentrated to approximately ⅔ volume in vacuo and the product was isolated by semi-preparative C18 HPLC eluting with a linear gradient of acetonitrile in aqueous 0.1% formic acid. The product fractions were frozen immediately after collection and lyophilized to give 12.55 mg (44% yield) of desired product 55. MS calcd (M+Na)$^+$, 717.3; found, 717.3.

Example 17

Thiol-Containing Ansamitocin 58 was Prepared as Follows (See FIG. 13b)

2-(methyldithio)propanoic acid (56)

To a solution of 2-mercaptopropanoic acid (2.0 mL, 22.55 mmol) in water (50.0 mL) was added sodium carbonate (4.77 g, 45.00 mmol) in portions while avoiding excessive froathing. After which, a solution of S-Methyl methanethiosulfonate (2.77 mL, 29.3 mmol) in ethanol (50.0 mL) was slowly added at ambient temperature. After 2 h the reaction volume was reduced to approximately one half its original volume in vacuo then acidified to pH ~2 using 1 M HCl and extracted with ethyl acetate (2×250 mL). The organic extracts were combined, washed with brine and concentrated in vacuo to give a crude oil which was purified by silica chromatography eluting with a mixture of hexanes:ethyl acetate:acetic acid (50:49:1). Product containing fractions were combined and concentrated in vacuo to give 2.3 g (67% yield) of desired product. $^1$H NMR ($CDCl_3$) δ 1.520 (3H, d, J=7.2 Hz), 2.446 (3H, s) and 3.559 (1H, m) ppm.

2-(methyldithio)propanoic acid ester of maytansinol (57)

To a solution of 2-(methyldithio)propanoic acid (303.3 mg, 1.992 mmol) in $CH_2Cl_2$ (2 mL) was added dicyclohexylcarbodiimide (438 mg, 2.124 mmol) 4-dimethylaminopyridine (86 mg, 0.708 mmol) and maytansinol (200.0 mg, 0.354 mmol). After 1 h ethyl acetate (20 mL) was added and the mixture was filtered, washed sequentially with saturated sodium bicarbonate (10 mL) and brine (5 mL) then dried over anhydrous $Na_2SO_4$ and concentrated in vacuo. The product was isolated by C18 HPLC eluting with a linear gradient of acetonitrile in aqueous 0.1% formic acid. Product containing fractions were collected, combined and concentrated in vacuo to give 8.53 mg (3.3% yield) of desired product. $^1$H NMR ($CDCl_3$, ref. 7.26 ppm) δ 0.821 (3H, s), 1.288 (3H, d, J=6.4 Hz), 1.455 (1H, m), 1.650 (1H, d J=4 Hz), 1.679 (3H, d, J=3.2 Hz), 1.693 (3H, s), 1.782 (1H, d, J=7.2 Hz), 2.245 (1H, dd, J=11.6, J=2.4 Hz), 2.494 (3H, s), 2.573 (1H, dd, J=11.6, J=2 Hz), 2.877 (1H, m), 3.186 (3H, s), 3.359 (3H, s), 3.511 (3H, m), 3.645 (1H, m), 3.987 (3H, s), 4.265 (1H, m), 4.914 (1H, dd, J=9.2, J=3.2 Hz), 5.539 (1H, dd, J=11.6, J=6.4 Hz), 6.158 (1H, d, J=11.2), 6.308 (1H, s), 6.422 (1H, dd, J=10.8, J=4.4 Hz), 6.834 (1H, s) and 6.905 (1H, d, J=1.6 Hz). MS calcd (M+Na)$^+$, 721.2; found, 721.2. MS calcd (M+Cl)$^-$, 733.2; found, 735.1.

2-(thio)propanoic acid ester of maytansinol (58)

To a solution of the 2-(methyldithio)propanoic acid ester of maytansinol (8 mg, 0.011 mmol) in 1,2-Dimethoxyethane (1 mL) was added a solution of D,L-dithiothreitol (5.29 mg, 0.034 mmol) in 100 mM potassium phosphate, 2 mM EDTA pH 7.5 buffer (1.000 mL) at ambient temperature. After 90 min the reaction volume was reduced to dryness in vacuo and purified by C18 HPLC eluting with a linear gradient of acetonitrile in aqueous 0.1% formic acid. The product containing fractions were immediately frozen and lyophilized to give 1.6 mg (18% yield) of desired product. MS calcd (M+Na)$^+$, 675.2; found, 676.2. MS calcd (M−H)$^-$, 651.1; found, 651.2.

Example 18

The ansamitocin derivative 13a is prepared by DCC coupling of 37 to N-hydroxysuccinimide.

Example 19

The ansamitocin 13b is prepared by DCC coupling of 37 to sulfo-N-hydroxysuccinimide.

Example 20

The ansamitocin derivative 22 is prepared as follows. The hydroxyl moiety of 30 is reacted with methanesulfonyl chloride to give the mesylate 52. A solution of maytansinol in tetrahydrofuran is deprotonated with butyl lithium at reduced temperature and canulated into a solution of 52 to form an ether bond and then the disulfide moiety is cleaved with DTT.

Example 21

Conjugation of Antibodies to Sulfhydryl-Bearing Ansamitocin Derivatives by Disulfide Linkers Antibody is conjugated to several molecules of a sulfhydryl-bearing ansamitocin derivative of the present invention by a previously described method (W. C. Widdison et al., *J. Med. Chem.*, 2006, 49, 4392-4408) which is described herein. A humanized antibody is first modified with a heterobifunctional linker (SPDB, SPP, SPDP) containing both an amine-reactive N-hydroxysuccinimide group (NHS group) and a thiol-reactive 2-pyridyldithio group (—SSPy group) to incorporate several molecules (e.g. 1 to 10) of the linker per molecule of antibody. After this, the ansamitocin derivative bearing a reactive thiol group is added to the linker-modified antibody to conjugate the ansamitocin derivative to antibody by disulfide bonds.

In a specific example, a humanized antibody at a concentration of 5-10 mg/ml is modified using 3 to 15-fold molar excess of heterobifunctional linker, such as SPDB, SPP and SPDP, in aqueous buffer at pH 6.5-8 for 0.25-3 h at ambient temperature and purified by gel filtration (using, for example, Sephadex G25 chromatography) to obtain antibody modified with an average 3-15 linker groups per antibody molecule. The linked groups are estimated by measuring the release of 2-thiopyridone based on its absorbance at 343 nm ($\epsilon_{343\,nm}$=8080 M$^{-1}$ cm$^{-1}$) upon addition of excess 1,4-dithiothreitol (DTT) reagent to a small aliquot of the linker-modified antibody sample. After measuring the number of linked reactive groups on the antibody, the linker-modified antibody is conjugated with an excess of the thiol-bearing ansamitocin derivative (typically 1.0-2.5-fold molar excess of the thiol-bearing ansamitocin derivative per reactive linker group) at an approximate antibody concentration of 2.5 mg/mL at pH 6.5-8 for a reaction time of 2-24 hours. The antibody-ansamitocin derivative conjugate is purified by gel filtration or dialysis to remove unreacted ansamitocin derivative. The number of linked ansamitocin derivatives per antibody molecule in the purified conjugate is determined from absorbance measurements at 252 nm and 280 nm and using the extinction coefficients for the ansamitocin derivative and antibody at 252 nm and 280 nm (FIG. 13, m=1 to 10).

Example 22

Conjugation of Antibody with Several Sulfhydryl-Bearing Ansamitocin Derivative Molecules Linked Per Antibody Molecule by Non-Cleavable Thioether Linkers Thioether-linked antibody-ansamitocin derivative conjugates can be prepared in a two-step process. A humanized antibody is modified with a heterobifunctional crosslinker bearing an amine-reactive N-hydroxysuccinimide group (NHS group) and a thiol-reactive maleimido, vinylpyridine, vinyl sulfone, vinyl sulfonamide or a haloacetyl-based group to incorporate several molecules of the linker in the antibody molecule. Crosslinking reagents comprising a maleimido-based moiety include N-succinimidyl 4-(maleimidomethyl) cyclohexanecarboxylate (SMCC), N-succinimidyl-4-(N-maleimidomethyl)-cyclohexane-1-carboxy-(6-amidocaproate), which is a "long chain" analogue of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Thiol reactive compounds which contain a vinylpyridine are described (Friedman M. et. Al. *Int. J. Peptide Protein Res.* 1974, 6, 183-185; Mak A. et. Al. Anal. Biochem. 1978, 84, 432-440). Thiol reactive compounds which contain a vinyl sulfone moiety have been described (Masri M. S. J. Protein Chem. 1988, 7, 49-54; Morpurgo, M. et. Al. Bioconjugate Chem. 1996, 7, 363-368) Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP).

The antibody is modified with an excess of heterobifunctional crosslinker at 5-10 mg/mL in aqueous buffer, pH 6.5-8, for 0.25-3 h at ambient temperature followed by purification by G25 chromatography. The number of linked maleimide or haloacetyl groups on the modified antibody is determined using a small aliquot of the linker-modified antibody and adding a known excess of thiol (such as 2-mercaptoethanol) over the maleimide or haloacetyl concentration. The thiol will react with the introduced maleimide or haloacetyl groups on the modified antibody and the excess thiol is measured by Ellman's assay using DTNB reagent (extinction coefficient of TNB thiolate at 412 nm=14150 M$^{-1}$ cm$^{-1}$; Riddles, P. W. et al., *Methods Enzymol.*, 1983, 91, 49-60; Singh, R., *Bioconjugate Chem.*, 1994, 5, 348-351). After measuring the number of linked reactive groups on the antibody, the linker-modified antibody is conjugated with an excess of the thiol-bearing ansamitocin derivative (1.0-2.5-fold molar excess of the thiol-bearing ansamitocin derivative per reactive linker group) at an approximate antibody concentration of 2.5 mg/mL at pH 6.5-8 for a reaction time of 2-24 hours. The non-cleavable antibody-ansamitocin derivative conjugate is purified by gel filtration or dialysis to remove any unreacted ansamitocin derivative. The number of non-cleavable ansamitocin-derivative molecules linked per antibody molecule in the purified conjugate is determined from absorbance measurements at 252 nm and 280 nm and using the extinction coefficients for the ansamitocin derivative and antibody at 252 nm and 280 nm (FIG. 14, 15, m=1 to 10).

Example 23

Conjugation of Antibody with Several Amine-Reactive Ansamitocin Derivative Molecules Linked Per Antibody Molecule An antibody-ansamitocin derivative conjugate can be prepared in a one-step process by modification of lysine residues on a humanized antibody with an amine-reactive ansamitocin derivative of the present invention. An ansamitocin derivative bearing an amine-reactive group such as an N-hydroxysuccinimide group (NHS group) is prepared as described in the present specification. A titration of antibody with several excesses of amine-reactive ansamitocin derivative is performed initially to determine the desired ansamitocin derivative to antibody ratio, typically this range is 6-10-fold molar excess for humanized antibody.

In a one-step process, a humanized antibody is reacted with an excess of the ansamitocin derivative bearing an amine-reactive NHS group at a concentration of 5-10 mg/mL in an aqueous buffer, pH 6.0-8.0, at ambient temperature for 1-24 h. The antibody-ansamitocin derivative conjugate is purified by gel chromatography followed by dialysis. The number of ansamitocin derivative molecules linked per antibody molecule in the final conjugate is determined by measuring the absorbance of the conjugate at 252 and 280 nm and using the extinction coefficients for the ansamitocin derivative and antibody at these two wavelengths (FIG. 19, m=1 to 10).

Example 24

Conjugation of Antibody with Several Ansamitocin Derivative Molecules Linked Per Antibody Molecule Using Acid-Labile Linkers In a two-step process to conjugate antibody with several molecules of a carbonyl-bearing ansamitocin derivative of the present invention, a humanized antibody is first modified with an excess of a commercially available heterobifunctional linker containing both an amine-reactive N-hydroxysuccinimide group (NHS group) and a carbonyl-reactive hydrazine group to incorporate several molecules of the linker in the antibody molecule. Examples of such commercially available crosslinkers include Succinimidyl 6-hydrazinonicotinamide acetone hydrazone (SANH), Succinimidyl 4-Hydrazidoterephthalate hydrochloride (SHTH) and Succinimidyl hydrazinium nicotinate hydrochloride (SHNH). The modified antibody is then reacted with an excess of the ketone or aldehyde-bearing ansamitocin derivative to conjugate the ansamitocin derivative to antibody via an acid-labile linkage.

Conjugates bearing an acid-labile linkage can also be prepared using a hydrazine-bearing ansamitocin derivative of the present invention. Similar to the two-step process described above, humanized antibody is modified with a commercially available heterobifunctional crosslinker bearing an amine-reactive N-hydroxysuccinimide group and a hydrazine-reactive carbonyl group. Examples of such crosslinkers include Succinimidyl-p-formyl benzoate (SFB) and Succinimidyl-p-formylphenoxyacetate (SFPA). The linker-modified antibody is then reacted with an excess of the hydrazide-bearing ansamitocin derivative to give an antibody-ansamitocin derivative conjugate linked via an acid-labile linkage (FIGS. 20-22, m=1 to 10).

Example 25

Amine-Reactive Ansamitocin Derivative 13a was Prepared as Follows (see FIG. 11)

Hexandioic acid-1-[trimethylsilyl)ethyl]ester of maytansinol (14a)

A reaction flask was charged with 6-oxo-6-(2-(trimethylsilyl)ethoxy)hexanoic acid (523 mg, 2.124 mmol), N,N'-dicyclohexylcarbodiimide (438 mg, 2.124 mmol) and methylene chloride (2.5 mL). 4-dimethylaminopyridine (86 mg, 0.708 mmol) was added to the stirring solution followed by the addition of maytansinol (200 mg, 0.354 mmol). The reaction stirred for 4 h at room temperature. After proceeding for 4 h, the crude reaction mixture was centrifuged and concentrated in vacuo. The resulting crude oil was purified by semi-preparative C18 HPLC to give 32 mg of 14a in 11.4% yield. HRMS (M+Na)$^+$ found: 815.3299. calculated: 815.3312 $^1$H NMR (400 MHz, CDCl$_3$) δ 6.84 (s, 1H), 6.77 (s, 1H), 6.43 (dd, J=15.3, 11.0 Hz, 1H), 6.32 (s, 1H), 6.17 (d, J=10.9 Hz, 1H), 5.52 (dd, J=15.4, 8.9 Hz, 1H), 4.89 (dd, J=11.9, 2.8 Hz, 1H), 4.24 (t, J=10.5 Hz, 1H), 4.15 (m, 2H), 3.99 (s, 3H), 3.52 (m, 2H), 3.37 (s, 3H), 3.22 (s, 2H), 3.17 (m, 1H), 3.16 (s, 3H), 2.87 (d, J=9.7 Hz, 1H), 2.49 (m, 2H), 2.34 (m, 2H), 2.18 (dd, J=13.9, 2.7 Hz, 1H), 2.00 (s, 3H), 1.68 (s, 3H), 1.63 (d, J=13.6 Hz, 1H), 1.46 (m, 1H), 1.27 (d, J=6.3 Hz, 3H), 1.22 (m, 1H), 0.97 (m, 2H), 0.83 (s, 3H), 0.03 (s, 9H).

Hexanedioic Acid Ester of Maytansinol (14b)

The trimethylsilyl-protected ansamitocin derivative 14a (30 mg, 0.038 mmol) was dissolved in tetrahydrofuran (0.38 mL) and cooled to 0° C. Once cooled, the reaction was treated with 1 M tetrabutylammonium fluoride in tetrahydrofuran (0.045 mL, 0.045 mmol). The cooling bath was removed and the reaction was warmed to room temperature and stirred for 6 h. The reaction was then quenched with saturated ammonium chloride, extracted into ethyl acetate, washed with brine, dried over anhydrous sodium sulfate and concentrated in vacuo. The crude product was purified by semi-preparative C18 HPLC to give 5.4 mg of the desired carboxylic acid ansamitocin derivative 14b in 20.6% yield. HRMS (M+Na)$^+$ found: 715.2593. calculated: 715.2604 $^1$H NMR (400 MHz, CDCl$_3$) δ 6.84 (s, 1H), 6.79 (s, 1H), 6.63 (s, 1H), 6.42 (dd, J=15.3, 10.9 Hz, 1H), 6.16 (d, J=10.6 Hz, 1H), 5.53 (dd, J=15.5, 8.8 Hz, 1H), 4.88 (d, J=9.1 Hz, 1H), 4.26 (t, J=10.9 Hz, 1H), 3.99 (s, 3H), 3.72 (m, 2H), 3.51 (m, 1H), 3.37 (s, 3H), 3.19 (s, 3H), 2.91 (d, J=9.7 Hz, 1H), 2.71 (m, 1H), 2.53 (m, 1H), 2.41 (m, 3H), 2.20 (d, 1H), 2.01 (s, 3H), 1.73 (m, 2H), 1.68 (s, 3H), 1.61 (d, J=13.7 Hz, 1H), 1.46 (m, 1H), 1.26 (m, 3H), 0.82 (s, 3H).

N-Hydroxysuccinimide Ester of the Hexanedioic Acid Ester of Maytansinol (13a)

A reaction flask was charged with 14b (5 mg, 0.007 mmol) and methylene chloride (1 mL). Sequentially, N-hydroxysuccinimide (4.15 mg, 0.036 mmol) and 1-ethyl-3-(3-dimethylaminopropyl)carbodiimide (6.91 mg, 0.036 mmol) were added to the stirring reaction mixture. The reaction proceeded overnight at room temperature. Following completion, the reaction volume was reduced in vacuo and the product was purified by semi-preparative C18 HPLC. Product containing fraction were collected, frozen and lyophilized to give 0.91 mg of the desired ansamitocin derivative bearing an N-hydroxysuccinimidyl ester group, 13a, in 15.9% yield. HRMS (M+Na)$^+$ found: 812.2763. calculated: 812.2768.

Example 26

Thiol-Containing Ansamitocin Derivative 6 was Prepared as Follows (see FIG. 5)

3-(methyldithio)propanoic acid ester of maytansinol (45)

A reaction flask was charged with 3-mercaptopropionic acid (28, 318 mg, 2.088 mmol), N,N'-dicyclohexylcarbodiimide (431 mg, 2.088 mmol) and methylene chloride (2.0 mL). The solution was stirred as 4-dimethylaminopyridine (85 mg, 0.696 mmol) and maytansinol (197 mg, 0.348 mmol) were sequentially added. The reaction was stirred for 2 h at room temperature. After 2 h, the reaction was filtered to remove precipitate and concentrated in vacuo. The product was isolated by semi-preparative C18 HPLC. Product containing fractions were combined and concentrated to dryness to give 93 mg (38.4%) of compound 45. HRMS (M+Na)$^+$ found: 763.2448. calculated: 763.2460. $^1$H NMR (400 MHz, CDCl$_3$) δ 6.84 (s, 1H), 6.82 (s, 1H), 6.45 (dd, J=15.4, 11.1 Hz, 1H), 6.32 (s, 1H), 6.19 (d, J=11.0 Hz, 1H), 5.54 (dd, J=15.4, 8.8 Hz, 1H), 4.98 (dd, J=11.9, 2.6 Hz, 1H), 4.23 (t, J=11.2 Hz, 1H), 3.99 (s, 3H), 3.52 (t, J=12.1 Hz, 2H), 3.37 (s, 3H), 3.20 (m, 2H), 3.16 (s, 3H), 2.89 (m, 2H), 2.83 (d, J=9.7 Hz, 1H), 2.70 (m, 2H), 2.52 (m, 1H), 2.20 (dd, J=13.9, 2.4 Hz, 1H), 1.72 (m, 1H), 1.68 (s, 3H), 1.62 (d, J=13.5 Hz, 2H), 1.48 (m, 1H), 1.28 (d, J=6.3 Hz, 3H), 1.23 (d, J=13.5 Hz, 1H), 0.84 (s, 3H).
$^{13}$C NMR (101 MHz, CDCl$_3$) δ 170.65, 168.66, 152.46, 149.47, 142.65, 140.20, 128.24, 124.63, 122.42, 119.58, 113.16, 88.22, 81.24, 74.46, 66.32, 60.48, 56.86, 56.73, 47.29, 38.48, 35.83, 34.38, 33.55, 32.93, 31.39, 24.86, 22.87, 22.31, 15.90, 14.76, 14.65, 12.22.

3-thiopropanoic acid ester of maytansinol (6)

In a 10 mL round bottom flask equipped with a stir bar, a solution of 45 (45 mg, 0.064 mmol) in 1,2-dimethoxyethane (3 mL) was prepared. D,L-dithiothreitol (49.6 mg, 0.322 mmol) in phosphate buffer pH 7.5 (3 mL, 100 mM potassium phosphate, 2 mM EDTA) was then added. The reaction flask was equipped with a septum and the reaction proceeded at room temperature with stirring under an argon atmosphere until completion. The reaction volume was reduced in vacuo and the product was isolated by semi-preparative C18 purification. Product containing fractions were frozen following the compounds elution and lyophilized to give 4 mg (9.5% yield) of compound 6 as a white solid. HRMS (M+Na)$^+$ found: 675.2092. calculated: 675.2114 $^1$H NMR (400 MHz, CDCl$_3$) δ 6.84 (s, 1H), 6.77 (s, 1H), 6.43 (dd, J=15.3, 11.0 Hz, 1H), 6.32 (s, 1H), 6.17 (d, J=10.9 Hz, 1H), 5.52 (dd, J=15.4, 8.9 Hz, 1H), 4.89 (dd, J=11.9, 2.8 Hz, 1H), 4.24 (t, J=10.5 Hz, 1H), 4.15 (m, 2H), 3.99 (s, 3H), 3.52 (dd, J=16.5, 11.0 Hz, 1H), 3.37 (s, 3H), 3.20 (m, 2H), 3.16 (s, 3H), 2.87 (d, J=9.7 Hz, 1H), 2.51 (m, 1H), 2.34 (m, 2H), 2.18 (dd, J=13.9, 2.7 Hz, 1H), 1.68 (s, 3H), 1.63 (d, J=13.6 Hz, 1H), 1.46 (m, 1H), 1.27 (d, J=6.3 Hz, 2H), 1.22 (m, 1H), 0.97 (m, 1H), 0.83 (s, 3H).
$^{13}$C NMR (101 MHz, CDCl$_3$) δ 170.35, 168.71, 156.18, 152.32, 142.66, 140.37, 140.14, 132.55, 128.14, 124.48, 122.33, 119.61, 113.15, 88.26, 81.21, 77.30, 74.42, 66.16, 60.49, 56.88, 56.72, 47.31, 38.67, 38.48, 35.85, 35.81, 32.95, 19.84, 15.93, 14.65, 12.27.

Example 27

Thiol-Containing Ansamitocin 58 was Prepared as Follows (See FIG. 13B)

2-(methyldithio)propanoic acid (56)

A round bottom flask equipped with a stir bar was charged with 2-mercaptopropanoic acid (1.99 mL, 2.39 g, 22.55 mmol) and water (50.0 mL). The solution was stirred as sodium carbonate (4.77 g, 45.00 mmol) was added slowly to the reaction flask. Separately, a solution of methyl methanethiolsulfonate (2.77 mL, 29.3 mmol) was prepared in ethanol (50.0 mL) and added slowly to the stirring reaction solution. The reaction proceeded at room temperature for 2 h under an argon atmosphere. Following reaction completion, the reaction volume was reduced to one half of the original volume in vacuo. The remaining aqueous solution was acidified to pH 2 using 1 M HCl and extracted with ethyl acetate (2×250 mL). The organic extracts were combined, washed with brine and concentrated in vacuo to give a crude oil. The product was purified by silica chromatography eluting with a mixture of hexanes:ethyl acetate: acetic acid (50:49:1). Product containing fractions were combined and concentrated in vacuo to give 2.3 g of purified 56 as a colorless oil in 67% yield. $^1$H NMR (CDCl$_3$) δ 1.520 (3H, d, J=7.2 Hz), 2.446 (3H, s), 3.559 (1H, m).

2-(methyldithio)propanoic acid ester of maytansinol (57)

A round bottom flask was charged with 2-(methyldithio) propanoic acid (56, 303.3 mg, 1.992 mmol), methylene chloride (2 mL) and a stir bar. As the solution stirred, N,N'-dicyclohexylcarbodiimide (438 mg, 2.124 mmol) was added followed by the sequential addition of 4-dimethylaminopyridine (86 mg, 0.708 mmol) and maytansinol (200.0 mg, 0.354 mmol). The flask was equipped with a septum and the reaction proceeded at room temperature with stirring. After 1 h the reaction was diluted with ethyl acetate (20 mL), filtered, washed sequentially with a saturated sodium bicarbonate solution (10 mL), and brine (5 mL), dried over anhydrous sodium sulfate and concentrated in vacuo. The product was isolated by semi-preparative C18 HPLC eluting with a linear gradient of acetonitrile in aqueous 0.1% formic acid. Product containing fractions were collected, combined and concentrated in vacuo to give 8.53 mg of compound 57 in 3.3% yield. HRMS (M+Na)$^+$ found: 721.1998. calculated: 721.1991 $^1$H NMR (400 MHz, CDCl$_3$) δ 6.91 (d, J=1.4 Hz, 1H), 6.83 (s, 1H), 6.42 (dd, J=15.4, 11.0 Hz, 1H), 6.31 (s, 1H), 6.16 (d, J=10.9 Hz, 1H), 5.54 (dd, J=15.5, 9.0 Hz, 1H), 4.91 (dd, J=12.0, 3.0 Hz, 1H), 4.26 (t, J=11.0 Hz, 1H), 3.99 (s, 3H), 3.65 (dd, J=14.5, 7.2 Hz, 1H), 3.51 (dd, J=10.6, 7.9 Hz, 1H), 3.36 (d, J=3.6 Hz, 3H), 3.19 (s, 3H), 2.86 (m, 1H), 2.57 (dd, J=14.1, 12.0 Hz, 1H), 2.49 (s, 3H), 2.24 (m, 1H), 1.89 (m, 1H), 1.78 (d, J=7.1 Hz, 1H), 1.69 (s, 3H), 1.68 (d, J=3.1 Hz, 3H), 1.65 (d, J=4.1 Hz, 1H), 1.47 (m, 1H), 1.29 (d, J=6.2 Hz, 3H), 1.25 (s, 1H), 0.82 (s, 3H).

2-(thio)propanoic acid ester of maytansinol (58)

A round bottom flask was charged with 57 (8 mg, 0.011 mmol), 1,2-dimethoxyethane (1 mL) and equipped with a stir bar. Separately, a solution of D,L-dithiothreitol (5.29 mg, 0.034 mmol) was prepared in phosphate buffer pH 7.5 (3 mL, 100 mM potassium phosphate, 2 mM EDTA) and added to the reaction flask. The reaction proceeded with stirring at room temperature and under an argon atmosphere until completion. Upon completion (90 min.) the reaction mixture was evaporated to dryness in vacuo and purified by semi-preparative C18 HPLC. The product was collected, frozen and lyophilized to give 1.6 mg of compound 58 isolated with 97.1% purity in 18.2% yield. MS calculated (M+Na)$^+$, 675.2; found, 676.2, MS calculated (M–H)$^-$, 651.1; found, 651.2.

Example 28

Thiol-Containing Ansamitocin 55 was Prepared as Follows (See FIG. 13A)

6-(methyldisulfanyl)hexanoic acid (53)

A reaction flask was cooled in an ice bath and charged with 6-mercaptohexanoic acid (500 mg, 3.37 mmol) and water (2 mL). The solution was stirred as methyl methanethiolsulfonate (468 mg, 3.71 mmol) dissolved in ethanol (1 mL) was added. The reaction was stirred overnight at room temperature under an argon atmosphere. The reaction mixture was then diluted with saturated sodium chloride (400 mL) and extracted into ether (3×150 mL). The combined extracts were washed with the sodium chloride solution, dried over anhydrous sodium sulfate and concentrated in vacuo. The product was isolated via silica flash chromatography eluting with a 1:0.9:0.1 mixture of hexanes:ethyl acetate:acetic acid to give 482 mg (73.5% yield) of compound 53. $^1$H NMR (CDCl$_3$, ref. 7.26 ppm) δ 1.473 (2H, m), 1.702 (4H, m), 2.359 (2H, t), 2.405 (3H, s), 2.708 (2H, t).

6-(methyldithio)hexanoic acid ester of maytansinol (54)

A reaction flask was charged with 6-(methyldisulfanyl)hexanoic acid (53, 413 mg, 2.124 mmol) and methylene chloride (2.0 mL). The stirring solution was sequentially treated with N,N'-dicylcohexylcarbodiimide (438 mg, 2.124 mmol), 4-dimethylaminopyridine (86 mg, 0.708 mmol) and maytansinol (200 mg, 0.354 mmol). The reaction proceeded overnight at room temperature with stirring. The reaction mixture was filtered, concentrated in vacuo and purified by semi-preparative C18 HPLC to give 36.7 mg of 54 in 13.9% yield. HRMS (M+Na)$^+$ found: 763.2448. calculated: 763.2460 $^1$H NMR (400 MHz, CDCl$_3$) δ 6.83 (s, 1H), 6.77 (s, 1H), 6.44 (m, 1H), 6.39 (s, 1H), 6.15 (d, J=11.2 Hz, 1H), 5.49 (m, 1H), 4.89 (dd, J=11.8, 2.6 Hz, 1H), 4.24 (t, J=10.5 Hz, 1H), 3.98 (s, 3H), 3.51 (m, 1H), 3.36 (s, 3H), 3.20 (d, 1H), 3.17 (s, 3H), 2.87 (m, 1H), 2.69 (m, 2H), 2.50 (m, 2H), 2.42 (s, 3H), 2.39 (s, 1H), 2.39 (s, 1H), 2.34 (m, 1H), 2.17 (d, 1H), 2.00 (s, 3H), 1.72 (m, 6H), 1.45 (m, 2H), 1.27 (d, J=6.3 Hz, 3H), 0.82 (s, 3H). $^{13}$C NMR (101 MHz, CDCl$_3$) δ 172.04, 168.97, 159.49, 156.21, 152.51, 151.65, 142.70, 140.17, 132.50, 128.19, 124.60, 122.23, 113.13, 88.32, 81.14, 74.47, 66.44, 60.49, 56.72, 47.35, 44.03, 38.60, 38.03, 35.76, 34.05, 32.91, 28.93, 27.90, 25.37, 24.36, 23.30, 22.30, 15.92, 14.67, 12.23.

6-mercaptohexanoic acid ester of maytansinol (55)

The disulfide-bearing ansamitocin derivative 54 (30.0 mg, 0.040 mmol) was dissolved in 1,2-dimethoxyethane (3 mL) in a 10 mL round bottom flask equipped with a stir bar. D,L-dithiothreitol (31.2 mg, 0.202 mmol) was added in phosphate buffer pH 7.5 (3 mL, 100 mM potassium phosphate, 2 mM EDTA). The reaction flask was equipped with a septum and the reaction proceeded at room temperature with stirring under an argon atmosphere for 3.5 h. The product was isolated by semi-preparative C18 HPLC purification. The product was frozen following elution and lyophilized to give 12.5 mg (44.6% yield) of 55. HRMS (M+Na)$^+$ found: 717.2563. calculated: 717.2583 $^1$H NMR (400 MHz, CDCl$_3$) δ 6.84 (d, J=1.5 Hz, 1H), 6.77 (d, J=1.5 Hz, 1H), 6.44 (dd, J=15.4, 11.0 Hz, 1H), 6.34 (s, 1H), 6.16 (d, J=11.2 Hz, 1H), 5.49 (dd, J=15.4, 8.9 Hz, 1H), 4.89 (dd, J=11.9, 2.8 Hz, 1H), 4.25 (t, J=10.5 Hz, 1H), 3.99 (s, 3H), 3.72 (q, J=7.0 Hz, 1H), 3.51 (m, 1H), 3.37 (s, 3H), 3.21 (d, J=12.8 Hz, 1H), 3.17 (s, 3H), 2.88 (m, 1H), 2.52 (m, 6H), 2.35 (m, 1H), 2.19 (dd, J=13.7, 2.7 Hz, 1H), 1.66 (d, J=7.3 Hz, 3H), 1.61 (m, 2H), 1.46 (m, 4H), 1.36 (m, 1H), 1.26 (m, 3H), 0.83 (s, 3H). $^{13}$C NMR (101 MHz, CDCl$_3$) δ 172.04, 168.82, 156.22, 152.41, 142.72, 140.19, 132.51, 128.17, 124.58, 122.22, 119.67, 113.12, 88.34, 81.14, 74.45, 66.47, 60.46, 56.73, 47.37, 44.03, 38.61, 35.75, 34.07, 33.66, 32.91, 29.85, 29.43, 28.70, 28.32, 27.81, 24.41, 15.92, 14.67, 12.23.

Example 29

Figure 6A:
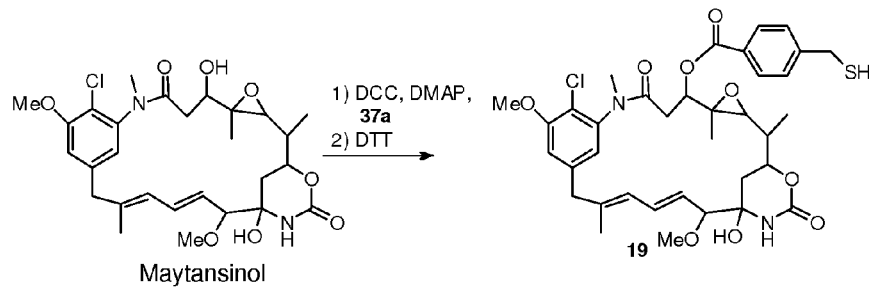
FIG. 6 shows the synthesis of thiol-containing ansamitocin derivatives bearing aromatic or heterocyclic side chains.
Figure 6B:
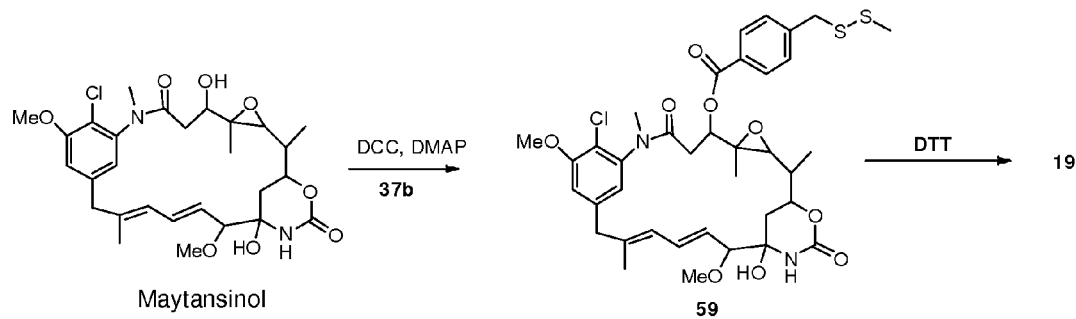
Figure 6C:
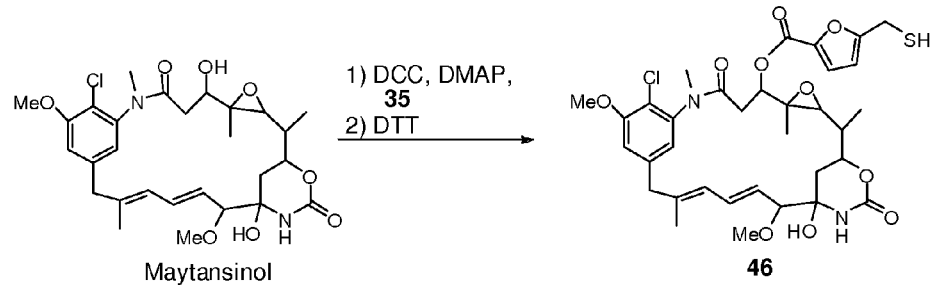

Thiol-Containing Ansamitocin Derivative 19 was Prepared as Follows (see FIG. 6B)

4-((methyldisulfanyl)methyl)benzoic acid (37b)

4-(mercaptomethyl)benzoic acid (36, 500 mg, 2.97 mmol) was dissolved in water (10 mL) and cooled in an ice bath. The cooled solution stirred as methyl methanethiolsulfonate (413 mg, 3.27 mmol) dissolved in ethanol (5.00 mL) was added. Following addition, the cooling bath was removed and the reaction was stirred overnight at room temperature. After proceeding overnight, the reaction was diluted with saturated sodium chloride and extracted with ether. The combined extracts were washed with sodium chloride, dried over anhydrous sodium sulfate and concentrated in vacuo. The product was isolated using silica flash chromatography eluting with a gradient of 40-60% ethyl acetate in hexanes containing 1% acetic acid over 20 min. to give 482 mg of the desired product, 4-((methyldisulfanyl)methyl)benzoic acid (37b), in 73.5% yield. $^1$H NMR (CDCl$_3$) δ 2.121 (3H, s), 3.938 (2H, s), 7.457 (2H, d, J=8.4 Hz), 8.068 (2H, d, J=8 Hz).

4-((methyldisulfanyl)methyl)benzoic acid ester of maytansinol (59)

A solution of 4-((methyldisulfanyl)methyl)benzoic acid (37b, 228 mg, 1.062 mmol) in methylene chloride (2.0 mL) was sequentially treated with N,N'-dicyclohexylcarbodiimide (219 mg, 1.062 mmol), 4-dimethylaminopyridine (43.2 mg, 0.354 mmol) and maytansinol (100 mg, 0.177 mmol). The reaction proceeded with stirring for 72 h after which the reaction mixture was filtered, concentrated in vacuo and purified by semi-preparative C18 HPLC to give 3.4 mg of compound 59 (2.5% yield). HRMS (M+Na)$^+$ found: 783.2155. calculated: 783.2147 $^1$H NMR (400 MHz, CDCl$_3$) δ 8.03 (d, J=8.2 Hz, 2H), 7.49 (d, J=8.2 Hz, 2H), 7.05 (d, J=1.5 Hz, 1H), 6.85 (d, J=1.5 Hz, 1H), 6.28 (dd, J=15.4, 10.9 Hz, 1H), 6.12 (s, 1H), 5.88 (d, J=10.8 Hz, 1H), 5.02 (dd, J=12.0, 3.3 Hz, 1H), 4.78 (dd, J=15.4, 9.1 Hz, 1H), 4.27 (t, J=10.4 Hz, 1H), 4.00 (s, 3H), 3.97 (s, 2H), 3.48 (d, J=12.9 Hz, 1H), 3.34 (d, J=9.1 Hz, 1H), 3.23 (s, 3H), 3.19 (s, 3H), 3.14 (d, J=9.6 Hz, 1H), 2.75 (t, J=13.2 Hz, 1H), 2.33 (dd, J=14.3, 3.2 Hz, 1H), 2.23 (s, 3H), 1.66 (s, 3H), 1.59 (d, J=13.3 Hz, 1H), 1.53-1.36 (m, 1H), 1.31 (d, J=6.3 Hz, 3H), 1.14 (t, J=12.9 Hz, 2H), 0.84 (s, 3H).

4-mercaptomethyl benzoic acid ester of maytansinol (19)

A 10 mL round bottom flask was charged with 59 (3 mg, 0.004 mmol), 1,2-dimethoxyethane (3 mL) and a stir bar. Separately, a solution of D,L-dithiothreitol (3.04 mg, 0.020 mmol) in phosphate buffer pH 7.5 (3 mL, 100 mM potassium phosphate, 2 mM EDTA) was prepared and added to the reaction flask. The reaction flask was equipped with a septum and the reaction proceeded at room temperature with stirring under an argon atmosphere for 3.5 h. The reaction volume was then concentrated in vacuo and the product was isolated by semi-preparative C18 purification. Product containing fractions were frozen following elution and lyophilized to give 1.4 mg of compound 19 as a white solid (35.5% yield). HRMS (M+Na)$^+$ found: 737.2269, calc.: 737.2270

Example 30

Pegylated, Thiol-Reactive Ansamitocin 60 was Prepared as Follows (See FIG. 7B)

PEG$_4$-SPDP Ester of Maytansinol (60)

A 10 mL round bottom flask was charged with SPDP-dPEG$_4$-acid (Quanta Biodesign, Ltd., Cat. #10373, 100 mg, 0.216 mmol) and methylene chloride (2 mL). The flask was equipped with a stir bar and the solution stirred as N,N'- dicylohexylcarbodiimide (134 mg, 0.648 mmol) was added. Maytansinol (61.0 mg, 0.108 mmol) and 4-dimethylaminopyridine (26.4 mg, 0.216 mmol) were then sequentially added. The flask was equipped with a septum and the reaction proceeded at room temperature with stirring. After 2.5 h the crude reaction mixture was filtered, concentrated in vacuo and purified by semi-preparative C18 HPLC. Product containing fractions were combined and concentrated in vacuo to give 30 mg of compound 60 as a clear oil in 27% yield. MS calculated $(M+Na)^+$, 1031.3; found, 1031.3; MS calculated $(M+Cl)^-$, 1043.3; found, 1043.2 $^1$H NMR (400 MHz, CDCl$_3$) δ 8.43 (d, J=4.1 Hz, 1H), 7.67 (m, 2H), 7.08 (m, 1H), 6.82 (s, 1H), 6.76 (d, J=1.3 Hz, 1H), 6.65 (s, 1H), 6.42 (dd, J=15.4, 11.0 Hz, 1H), 6.20 (d, J=11.0 Hz, 1H), 5.61 (dd, J=15.5, 8.9 Hz, 1H), 4.93 (dd, J=11.8, 2.5 Hz, 1H), 4.55 (s, 1H), 4.24 (t, J=11.2 Hz, 1H), 3.97 (s, 3H), 3.87 (m, 1H), 3.63 (m, 8H), 3.50 (m, 3H), 3.32 (s, 3H), 3.15 (s, 3H), 3.07 (m, 2H), 2.81 (d, J=9.5 Hz, 2H), 2.70 (m, 1H), 2.62 (m, 2H), 2.48 (m, 1H), 2.16 (dd, J=13.9, 2.4 Hz, 1H), 1.91 (m, 1H), 1.69 (m, 2H), 1.65 (s, 3H), 1.59 (m, 2H), 1.47 (m, 1H), 1.32 (m, 2H), 1.26 (d, J=6.4 Hz, 3H), 1.10 (m, 4H), 0.84 (s, 3H). $^{13}$C NMR (101 MHz, CDCl$_3$) δ 171.03, 170.01, 168.76, 160.03, 156.94, 156.09, 152.88, 149.71, 142.59, 140.33, 139.72, 137.28, 132.21, 128.87, 124.74, 122.27, 120.91, 119.91, 119.46, 113.15, 88.79, 80.87, 74.44, 70.92, 70.57, 70.47, 70.34, 70.13, 69.91, 66.38, 66.17, 60.60, 56.80, 56.69, 49.24, 47.20, 39.41, 38.39, 35.72, 35.55, 34.62, 34.08, 25.76, 25.08, 15.82, 14.68, 12.19.

Example 31

Ansamitocin Derivatives 64a and 64b were Prepared as Follows (See FIG. 13C)

3,7-dimethyloxepan-2-one (61)

A 250 mL round bottom flask was charged with 2,6-dimethylcyclohexanone (2.162 mL, 2.0 g, 15.85 mmol) and 126 mL of a 1:1 methanol/water mixture. The solution stirred as magnesium monoperoxyphthalate hexahydrate (MMPP, 15.68 g, 31.7 mmol) and sodium bicarbonate (2.66 g, 31.7 mmol) were added. The reaction proceeded overnight at room temperature with stirring. The following day the crude product was extracted into ethyl acetate, washed sequentially with saturated sodium bicarbonate, brine and dried over anhydrous sodium sulfate before concentrating in vacuo to give 1.07 g (47.5% yield) of 3,7-dimethyloxepan-2-one (61) as a clear, colorless oil.

6-mercapto-2-methylheptanoic acid (62)

A 10 mL round bottom flask equipped with a stir bar was charged with 3,7-dimethyloxepan-2-one (61, 0.729 g, 5.13 mmol), hydroiodic acid (2.029 ml, 15.38 mmol) and thiourea (2.73 g, 35.91 mmol). The flask was equipped with a water cooled water condenser, placed under a nitrogen atmosphere and heated to reflux. The reaction proceeded at reflux overnight. A sodium hydroxide (3.69 g, 92 mmol) solution in water (5 mL) was then added to the reaction flask. The reaction was refluxed overnight. The reaction mixture was removed from heat, cooled to room temperature and the flask contents were transferred to a separatory funnel. The aqueous layer was extracted with ethyl acetate and the extract was set to the side. The aqueous layer was acidified with HCl to pH 2 and extracted with ethyl acetate (2×100 mL) and methylene chloride (1×100 mL). The organic extracts were combined, washed with 30 mL of brine, dried over anhydrous sodium sulfate and concentrated in vacuo to give 823 mg of crude 6-mercapto-2-methylheptanoic acid (62, 92% yield) as a light brown oil.

2-methyl-6-(methyldisulfanyl)heptanoic acid (63)

A 100 mL round bottom flask was charged with crude 6-mercapto-2-methylheptanoic acid (62, 832.3 mg, 4.72 mmol) and water (30 mL). Sodium carbonate (1.001 g, 9.44 mmol) was added to the stirring solution. Separately, a solution of methyl methanthiolsulfonate (0.668 mL, 7.08 mmol) was prepared in ethanol (30 mL) and added slowly to the stirring reaction mixture. Following complete addition, the reaction flask was equipped with a septum and placed under an argon atmosphere. The reaction mixture stirred at room temperature for 3 h.

After 3 h the reaction volume was reduced by half in vacuo. The remaining aqueous phase was transferred to a separatory funnel and extracted twice with ethyl acetate (2×40 mL). The organic extracts were set to the side as the aqueous phase was acidified to pH 2 with concentrated HCl. Following acidification, the aqueous phase was extracted with ethyl acetate (3×70 mL). The organic extracts were combined and the product was back extracted into saturated sodium bicarbonate (3×100 mL). The aqueous extracts were combined and acidified to pH 2 with concentrated HCl. The acidified aqueous phase was then transferred to a separatory funnel and the product was extracted into ethyl acetate (3×100 mL). The organic extracts were combined, washed with 50 mL brine, dried over anhydrous sodium sulfate and concentrated in vacuo to give a crude yellow oil. The product was purified by silica gel chromatography eluting with a mixture of 66:33:1 Hexanes:Ethyl acetate: acetic acid. The product containing fractions were combined and concentrated in vacuo to give 292 mg of compound 63 in 28% yield. $^1$H NMR (CDCl$_3$) δ 1.189 (3H, d, J=7.2 Hz), 1.317 (3H, d J=6.4 Hz), 1.442-1.706 (6H, m), 2.392 (3H, s), 2.475 (1H, m), 2.840 (1H, m).

2-methyl-6-(methyldisulfanyl)heptanoic acid ester of maytansinol (64a and 64b)

A 10 mL round bottom flask was charged with maytansinol (29.6 mg, 0.052 mmol), methylene chloride (3 mL) and a stir bar. The solution was stirred as 2-methyl-6-(methyldisulfanyl)heptanoic acid (63, 69.9 mg, 0.314 mmol) was added, followed by the sequential addition of N,N'-dicyclohexylcarbodiimide (64.8 mg, 0.314 mmol) and 4-dimethylaminopyridine (12.8 mg, 0.105 mmol). The reaction flask was equipped with a septum and the reaction proceeded at room temperature for 4 h. The crude reaction mixture was transferred to a separatory funnel and diluted with ethyl acetate. The organic phase was washed with two portions of saturated sodium bicarbonate, once with brine and concentrated in vacuo to give a crude yellow oil. The product was purified by semi-preparative C18 HPLC. Two peaks corresponding to the racemates of the product were collected separately and concentrated in vacuo to give a combined total of 4.7 mg of the desired compound (64a: 2.1 mg and 64b: 2.6 mg). MS $(M+Na)^+$ found 64a: 791.0. calculated: 791.3. $(M+Cl)^-$ found 64a: 802.9. calculated: 803.2. MS $(M+Na)^+$ found 64b: 791.1. calculated: 791.3; $(M+Cl)^-$ found 64b: 802.9. calculated: 803.2.

Example 32

Ansamitocin Derivative 66 was Prepared as Follows (See FIG. 10B)

Dimethylamino Butyric Acid Ester of Maytansinol (66)

A reaction flask was charged with 4-(dimethylamino)-butyric acid HCl (93.5 mg, 0.558 mmol), N,N-diisopropylethylamine (15.45 µL, 0.088 mmol) and methylene chloride (0.2 mL). N,N'-dicyclohexylcarbodiimide (110 mg, 0.531 mmol), 4-dimethylaminopyridine (21.62 mg, 0.177 mmol) and maytansinol (50 mg, 0.088 mmol) were then sequentially added. The reaction flask was equipped with a septum and the reaction proceeded at room temperature with stirring for 72 h. The crude reaction mixture was filtered, concentrated in vacuo and purified by semi-preparative C18 HPLC. Product containing fractions were collected, combined and concentrated in vacuo to give 8.2 mg (13.7% yield) of compound 66. MS calculated $(M+H)^+$; 678.3; found, 678.2.

Example 23

In Vitro Activity of Ansamitocin Derivatives

FIGS. 28-30 show the cytotoxic activities of various ansamitocin derivatives of the present invention against the KB, COLO 205 and COLO 205-MDR cell lines. The disulfide-bearing ansamitocin derivatives 45, 54, 57, 59, 64a and 64b were potent with $IC_{50}$ values ranging between 0.27 nM to 4 nM against the KB cell line (FIG. 28a-d). When tested against the human colon carcinoma cell line COLO 205, the disulfide-bearing ansamitocin derivatives 54 and 59 showed similar potencies with measured $IC_{50}$ values of 0.31 nM and 0.53 nM, respectively.

The synthetic precursors of compound 13a, the amine-reactive linkable ansamitocin derivative, were evaluated against the KB, COLO 205 and COLO 205-MDR cell lines. The activity of the TMS-protected precursor, 14a, against the three cell lines ranged between 0.40 nM, against COLO 205 cells, to 4.8 nM against the COLO 205 MDR cell line. Following removal of the TMS protecting group, the ansamitocin derivative bearing a terminal carboxylic acid, 14b, was isolated and evaluated in vitro against the KB cell line. A 15-fold reduction in activity was observed for 14b when compared to the TMS-protected precursor against the KB cell line. The decrease in potency is most likely due to the poorer cellular permeability of the charged ansamitocin carboxylate. However, delivery inside the cell can be achieved by conjugation to a cell binding agent, such as a monoclonal antibody, to enhance potency.

The dimethylamino butyric acid ansamitocin derivative, 66, was the least potent of the tested compounds across the three cell lines. The measured $IC_{50}$ for this compound against the non-MDR cell lines was 11-12 nM and >20 nM against the COLO 205 MDR cell line (FIG. 30).

Example 34

Conjugation of Antibody to a Sulfhydryl-Bearing Ansamitocin Derivative by Disulfide Linkers

A solution of the sulfhydryl-bearing ansamitocin derivative 55 (8.4 mM stock, w/v) was prepared in DMA. The stock solution was diluted in ethanol and the absorbance was measured at 280 nm against a reagent blank of ethanol and DMA. The concentration of stock 55 was calculated by using an extinction coefficient of 5,456 $M^{-1}$ at 280 nm which is the experimentally determined extinction coefficient of maytansinoids at this wavelength.

The anti-EpCam antibody (5 mg/mL) in pH 7.5 20 mM sodium phosphate, 150 mM sodium chloride buffer containing DMA (5%, v/v) was reacted with a 8-fold molar excess of SPP (10 mM in DMA) for 3 hours at room temperature. The modified antibody was then diluted to 2.5 mg/mL with pH 6.5 20 mM sodium phosphate, 50 mM sodium chloride, 2 mM EDTA buffer and treated with a 2-fold molar excess of 55 per molar excess of SPP used in the modification reaction. The conjugation reaction was carried out in pH 6.5 buffer with DMA (7.5%, v/v) for 20 hours at room temperature. The conjugate was then purified over a NAP-25 (Sephadex G25) column equilibrated in a buffer consisting of 10 mM Histidine, 250 mM Glycine, 1% sucrose, pH 5.5, dialyzed and filtered. Following dialysis, the conjugate had 3.8 ansamitocin molecules linked per antibody molecule. The number of ansamitocin molecules per antibody molecule in the final conjugate was determined using the measured absorbance of the conjugate at 252 and 280 nm and using known extinction coefficients for maytansinoids and antibody at these two wavelengths. SEC HPLC was performed on the conjugate to show that it was 86% monomeric following conjugation.

Example 34

Conjugation of Antibody with an Amine-Reactive Ansamitocin Derivative

A 5 mM stock (w/v) of the amine-reactive ansamitocin derivative 13a was prepared in DMA. The stock solution was diluted in ethanol and the absorbance was measured at 280 nm against a reagent blank of ethanol and DMA. The concentration of stock 13a was calculated by using an extinction coefficient of 5,456 $M^{-1}$ at 280 nm which is the experimentally determined extinction coefficient of maytansinoids at the wavelength.

The anti-EpCam antibody was conjugated with a 12-fold molar excess of 13a at 2.5 mg/mL in pH 7.5 20 mM sodium phosphate, 150 mM sodium chloride buffer with DMA (10%, v/v) for 4.5 h at room temperature. The conjugate was then purified over a NAP-10 (Sephadex G25) column equilibrated in a buffer consisting 10 mM Histadine, 250 mM Glycine, 1% sucrose, pH 5.5, dialyzed and filtered. Following dialysis, the conjugate had 3.3 ansamitocin molecules linked per antibody molecule and no detectable free drug in the conjugate. The number of ansamitocin molecules per antibody molecule in the final conjugate was determined using the measured absorbance of the conjugate at 252 and 280 nm and using known extinction coefficients for maytansinoids and antibody at these two wavelengths (FIG. 20). SEC HPLC was performed on the conjugate to show that it was 91% monomeric following conjugation.

Example 35

In Vitro Cytotoxicity of Conjugates Prepared with Ansamitocin Derivatives and Maytansinoids

Conjugates targeting the EpCam antigen prepared with the linkable ansamitocin derivatives, 55 and 13a, were evaluated in vitro for potency against the EpCam expressing cell line COLO 205. The disulfide-linked mAb-SPP-55 conjugate was potent and specific with a measured activity of 0.23 nM (FIG. 31). The non-cleavable ansamitocin conjugate, mAb-13a, was slightly more active than the disulfide conjugate with an IC$_{50}$ value of 0.14 nM (FIG. 31). Both conjugates tested were specific against the targeted cell line indicated by the loss of activity when the conjugates were tested against COLO 205 cells that were pre-treated with an excess of the unconjugated anti-EpCam antibody prior to incubation with the anti-Ep-Cam mAb-ansamitocin conjugates (FIG. 31).

What is claimed is:

1. A cell binding agent conjugate, or a pharmaceutically acceptable salt thereof, wherein the conjugate is represented by the following formula:

(MayO-A-Y-M'-BFCG)$_m$-CB;

wherein:
MayO is represented by the formula:

wherein:
X'$_4$=X'$_5$ or OX'$_5$, and
X', X'$_1$, X'$_2$, X'$_3$, and X'$_5$ are the same or different and are selected from the group consisting of: R, C(=O)R, C(=O)NR$_2$, and C(=O)OR, wherein: each R is independently selected from the group consisting of: H, substituted or unsubstituted linear, branched, or cyclic alkyl, alkenyl or alkynyl, and substituted or unsubstituted aryl;
Q is O or S; provided that at least one of X', X'$_1$, X'$_2$, X'$_3$, X'$_5$ represents a covalent bond between MayO and A or AY;
A is an optional group selected from the group consisting of: C=O, C(=O)NR', and C(=O)O, R' is selected from the group consisting of: H, substituted or unsubstituted linear, branched, or cyclic alkyl, alkenyl or alkynyl, and substituted or unsubstituted aryl;
Y is represented by formula —[Ar"]$_{0-1}$—(CR$^1$R$^2$)$_x$—B—W-D-(CR$^1$R$^2$)$_w$—;
wherein:
Ar" is phenyl, —CH$_2$-phenyl, heterocyclyl, or —CH$_2$-heterocyclyl, optionally substituted with one to four groups selected from the group consisting of: alkyl, alkoxyl, halo, haloalkyl, alkoxy-haloalkyl, nitrile and nitro;
each R$^1$ and R$^2$ is independently hydrogen or C$_{1-4}$alkyl;
B is NR", O or absent;
W is an amino acid or a peptide comprising 2 to 8 amino acids, (OCH$_2$CH$_2$)$_n$ or absent;
D is CO, NR" or absent;
R" is selected from the group consisting of: H, substituted or unsubstituted linear, branched, or cyclic alkyl, alkenyl or alkynyl, and substituted or unsubstituted aryl;
x is an integer from 1 to 10;
w is 0 or an integer from 1 to 10; and,
n is an integer from 1 to 200;
BFCG is absent, or the residue of a bifunctional crosslinking reagent comprising two linking groups, wherein one of the linking groups has reacted with M', and the other linking group has reacted with the cell binding agent (CB) and is linked to the CB through a thioether or an amide moiety;
M' is the residue of a linking group that together with one of the reacted linking groups of BFCG forms a thioether or a disulfide;
m is an integer from 1 to 20; and,
CB represents the cell binding agent;
provided that the conjugate does not comprise a N-methylalanine or N-methylcysteine moiety represented by the following formula:

directly connected to MayO—.

2. The cell binding agent conjugate of claim 1, wherein Y is represented by one of the following formula:

-continued

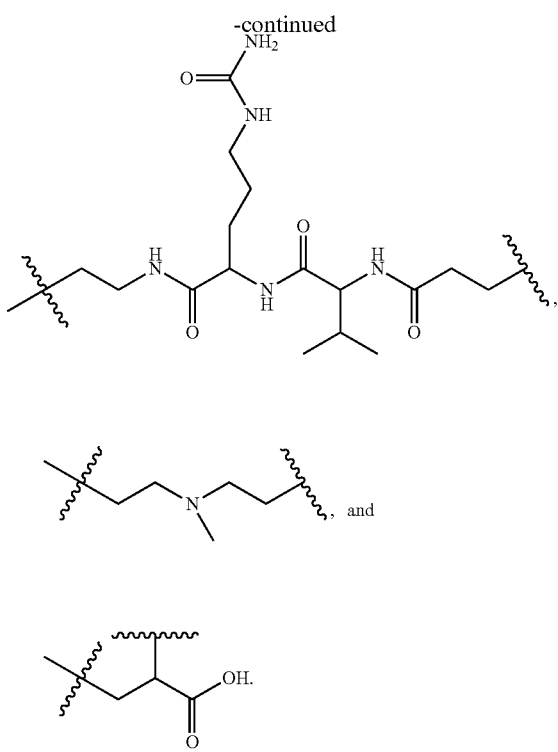

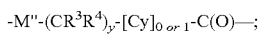

3. The cell binding agent conjugate of claim 1, wherein —BFCG- is represented by formula:

-M''-(CR³R⁴)y-[Cy]₀ or 1-C(O)—;

wherein:
M'' is

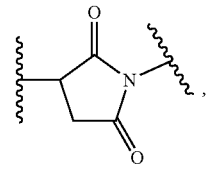

each R³ and R⁴ is independently hydrogen, methyl or —SO₃⁻M⁺, wherein: M⁺ is H⁺ or a pharmaceutically acceptable cation;
Cy is a cycloalkyl or a phenyl optionally substituted with one to four groups selected from the group consisting of: alkyl, alkoxyl, halo, haloalkyl, alkoxy haloalkyl, nitrile and nitro; and
y is 0 or an integer from 1 to 10.

4. The cell binding agent conjugate of claim 1, wherein —BFCG- is represented by formula:

—S—(CR³R⁴)y'—C(O)—;

wherein:
each R³ and R⁴ is independently hydrogen, methyl or —SO₃⁻M⁺, wherein: M⁺ is H⁺ or a pharmaceutically acceptable cation; and,
y' is an integer from 1 to 10.

5. The cell binding agent conjugate of claim 1, wherein BFCG comprises a self-immolative moiety.

6. The cell binding agent conjugate of claim 1, wherein the BFCG is selected from the group consisting of:

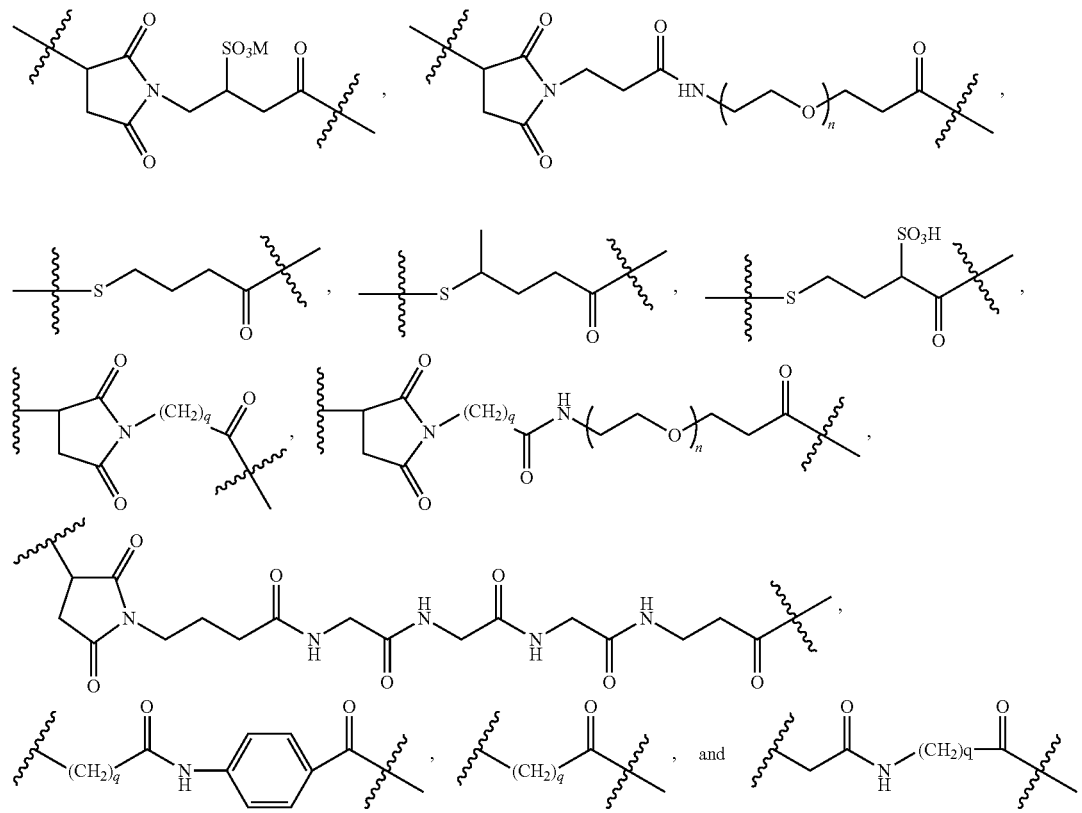

wherein:

q is an integer from 1 to 5;

n is an integer from 1 to 20; and

M is H+ or a pharmaceutically acceptable cation.

7. The cell binding agent conjugate of claim 1, wherein the cell-binding agent binds to target cells selected from the group consisting of: tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, STEAP, TENB2, MUC16, IRTA1, IRTA2, IRTA3, IRTA4, IRTA5, c-MET, 5T4, or Her-2 antigens; Her-3 antigens or cells expressing insulin growth factor receptor, epidermal growth factor receptor, or folate receptor.

8. The cell binding agent conjugate of claim 1, wherein the cell-binding agent is an antibody, a single chain antibody, an antibody fragment that specifically binds to the target cell, a monoclonal antibody, a single chain monoclonal antibody, or a monoclonal antibody fragment that specifically binds the target cell, a chimeric antibody, a chimeric antibody fragment that specifically binds to the target cell, a domain antibody, a domain antibody fragment that specifically binds to the target cell, a diabody, a nanobody, a probody, a Darpin, a lymphokine, a hormone, a vitamin, a growth factor, a colony stimulating factor, or a nutrient-transport molecule.

9. A pharmaceutical composition comprising the conjugate of claim 1 and a pharmaceutically acceptable carrier.

10. A compound or a pharmaceutically acceptable salt thereof, wherein the compound comprises a derivatized maytansinol or maytansinol analog residue and a linking group L that can form a chemical bond to a cell binding agent or a bifunctional crosslinking reagent, wherein the compound is represented by formula:

MayO-A-Y-L;

wherein:

MayO is represented by the formula:

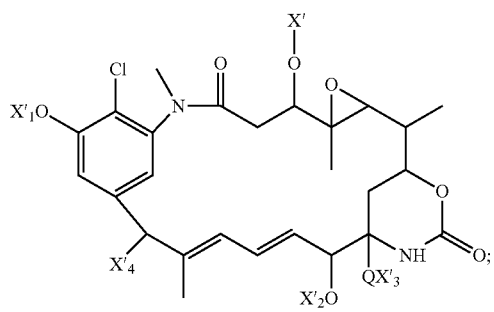

wherein:

$X'_4=X'_5$ or $OX'_5$, and $X'$, $X'_1$, $X'_2$, $X'_3$, and $X'_5$ are the same or different and are selected from the group consisting of: R, C(=O)R, C(=O)NR$_2$, and C(=O)OR, wherein: each R is independently selected from the group consisting of: H, substituted or unsubstituted linear, branched, or cyclic alkyl, alkenyl or alkynyl, and substituted or unsubstituted aryl;

Q is O or S; provided that at least one of X', $X'_1$, $X'_2$, $X'_3$, $X'_5$ represents a covalent bond between MayO and A or AY;

A is an optional group selected from the group consisting of: C=O, C(=O)NR', and C(=O)O; and R' is selected from the group consisting of: H, substituted or unsubstituted linear, branched, or cyclic alkyl, alkenyl or alkynyl, and substituted or unsubstituted aryl;

Y is represented by formula -[Ar"]$_{0-1}$—(CR$^1$R$^2$)$_x$—B—W-D-(CR$^1$R$^2$)$_w$—;

wherein:

Ar" is phenyl, —CH$_2$-phenyl, heterocyclyl, or —CH$_2$-heterocyclyl, optionally substituted with one to four groups selected from the group consisting of: alkyl, alkoxyl, halo, haloalkyl, alkoxy-haloalkyl, nitrile and nitro;

each R$^1$ and R$^2$ is independently hydrogen or C$_{1-4}$alkyl;

B is NR", O or absent;

W is an amino acid or a peptide comprising 2 to 8 amino acids, (OCH$_2$CH$_2$)$_n$ or absent;

D is CO, NR" or absent;

R" is selected from the group consisting of: H, substituted or unsubstituted linear, branched, or cyclic alkyl, alkenyl or alkynyl, and substituted or unsubstituted aryl;

x is an integer from 1 to 10;

w is 0 or an integer from 1 to 10; and, n is an integer from 1 to 200;

L is represented by a structural formula selected from: a maleimide, a haloacetamido, —SH, —SSR$_d$, —CH$_2$SH, —CH(Me)SH, —C(Me)$_2$SH, —COOH, and —COE, wherein COE represents a reactive ester, R$_d$ is an optionally substituted phenyl or an optionally substituted pyridyl and R is H or an alkyl;

provided the compound does not comprise a N-methyl alanine or N-methylcysteine moiety represented by the following formula:

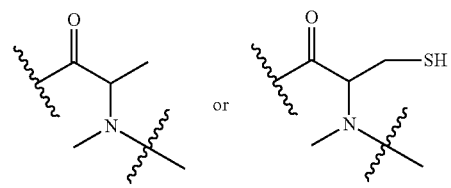

directly connected to MayO—.

11. A compound comprising a bifunctional crosslinking reagent linked to a derivatized maytansinol or maytansinol analog residue, wherein the compound is represented by the formula:

MayO-A-Y-M'-BFCG'-Z';

or a pharmaceutically acceptable salt thereof, wherein:
MayO is represented by the formula:

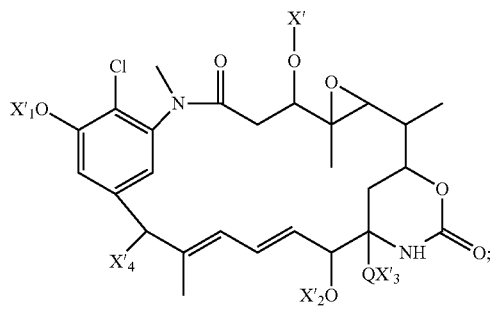

wherein:
$X'_4 = X'_5$ or $OX'_S$, and
$X'$, $X'_1$, $X'_2$, $X'_3$, and $X'_5$ are the same or different and are selected from the group consisting of: R, C(=O)R, C(=O)NR$_2$, and C(=O)OR, wherein: each R is independently selected from the group consisting of: H, substituted or unsubstituted linear, branched, or cyclic alkyl, alkenyl or alkynyl, and substituted or unsubstituted aryl;
Q is O or S; provided that at least one of $X'$, $X'_1$, $X'_2$, $X'_3$, $X'_5$ represents a covalent bond between MayO and A or AY;
A is an optional group selected from the group consisting of: C=O, C(=O)NR', and C(=O)O; R' is selected from the group consisting of: H, substituted or unsubstituted linear, branched, or cyclic alkyl, alkenyl or alkynyl, and substituted or unsubstituted aryl;
Y is represented by formula -[Ar"]$_{0-1}$—(CR$^1$R$^2$)$_x$—B—W-D-(CR$^1$R$^2$)$_w$—;
wherein:
Ar" is phenyl, —CH$_2$-phenyl, heterocyclyl, or —CH$_2$-heterocyclyl, optionally substituted with one to four groups selected from the group consisting of: alkyl, alkoxyl, halo, haloalkyl, alkoxy-haloalkyl, nitrile and nitro;
each R$^1$ and R$^2$ is independently hydrogen or C$_{1-4}$alkyl;
B is NR", O or absent;
W is an amino acid or a peptide comprising 2 to 8 amino acids, (OCH$_2$CH$_2$)$_n$, or absent;
D is CO, NR" or absent;
R" is selected from the group consisting of: H, substituted or unsubstituted linear, branched, or cyclic alkyl, alkenyl or alkynyl, and substituted or unsubstituted aryl;
x is an integer from 1 to 10;
w is 0 or an integer from 1 to 10; and,
n is an integer from 1 to 200;
BFCG'-Z' is the residue of a bifunctional crosslinking reagent comprising two linking groups, wherein one of the linking groups is represented by Z' and the other has reacted with M';
Z' is a linking group that can be linked to a cell binding agent via a thioether or an amide;
M' is the residue of a linking group that together with one of the reacted group of BFCG' forms a thioether or a disulfide;
provided that the compound does not comprise a N-methylalanine or N-methylcysteine moiety represented by the following formula:

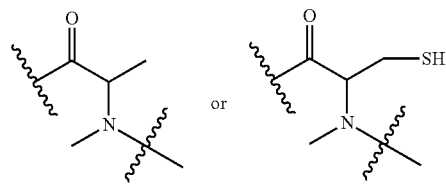

directly connected to MayO—.

* * * * *